US012558408B2

(12) United States Patent (10) Patent No.: US 12,558,408 B2
King et al. (45) Date of Patent: Feb. 24, 2026

(54) INTRATUMORALLY INJECTED YEAST VACCINE

(71) Applicant: ImmunityBio, Inc., Culver City, CA (US)

(72) Inventors: Thomas H. King, Culver City, CA (US); Zhimin Guo, Culver City, CA (US); Courtney Fleenor, Culver City, CA (US); Melanie Hermreck, Culver City, CA (US)

(73) Assignee: ImmunityBio, Inc., San Diego, CA (US)

( * ) Notice: Subject to any disclaimer, the term of this patent is extended or adjusted under 35 U.S.C. 154(b) by 280 days.

(21) Appl. No.: 18/179,907

(22) Filed: Mar. 7, 2023

(65) Prior Publication Data

US 2023/0285528 A1 Sep. 14, 2023

Related U.S. Application Data

(60) Provisional application No. 63/317,628, filed on Mar. 8, 2022.

(51) Int. Cl.
| | |
|---|---|
| *A61K 39/00* | (2006.01) |
| *A61P 35/04* | (2006.01) |
| *C07K 16/24* | (2006.01) |
| *C07K 16/28* | (2006.01) |

(52) U.S. Cl.
CPC ........ *A61K 39/00114* (2018.08); *A61P 35/04* (2018.01); *C07K 16/244* (2013.01); *C07K 16/2818* (2013.01); *C07K 16/2827* (2013.01); *C07K 16/2875* (2013.01); *C07K 16/2878* (2013.01); *A61K 2039/505* (2013.01); *A61K 2039/545* (2013.01)

(58) Field of Classification Search
None
See application file for complete search history.

(56) References Cited

U.S. PATENT DOCUMENTS

| | | |
|---|---|---|
| 2018/0214525 A1 | 8/2018 | King et al. |
| 2020/0171137 A1 | 6/2020 | Soon-Shiong et al. |

FOREIGN PATENT DOCUMENTS

| | | |
|---|---|---|
| WO | WO 2012/019127 | 2/2012 |
| WO | WO 2014/144885 | 9/2014 |
| WO | WO 2018/102613 | 6/2018 |

OTHER PUBLICATIONS

International Search Report and Written Opinion for International (PCT) Patent Application No. PCT/US2023/063876, dated Jun. 6, 2023 10 pages.

*Primary Examiner* — Gary B Nickol
*Assistant Examiner* — Cheom-Gil Cheong
(74) *Attorney, Agent, or Firm* — Sheridan Ross P.C.

(57) ABSTRACT

Disclosed herein are compositions and methods for treating solid tumors with yeast-based formulations.

16 Claims, 67 Drawing Sheets

PBS

CpG+aOX40

PTK170+aOX40

PTK170+aOX40+aCTLA4

Treated Tumor

* Stats to PBS control group

^ Stats comparing PTK170+αOX40 to PTK170+ αOX40+ αCTLA4

Yeast are needed for best effect

B16F10 tumor model
i.t. injection 5YU Y-neo

PBS treated
25ug aOX40 + aCTLA-4
Y-neo Int + 25ug aOX40 + aCTLA-4
Y-neo Lys + 25ug aOX40 + aCTLA-4

Intact: 8/9 CR
Lysate: 7/8 CR tumor volume (mm³)

Days post treatment errors indicate i.t. injections

Stats: 2way ANOVA w Dunett's multiple comparison
P<0.0001 for intact and lysate groups compared to PBS starting day 8 onwards

Fig. 6C

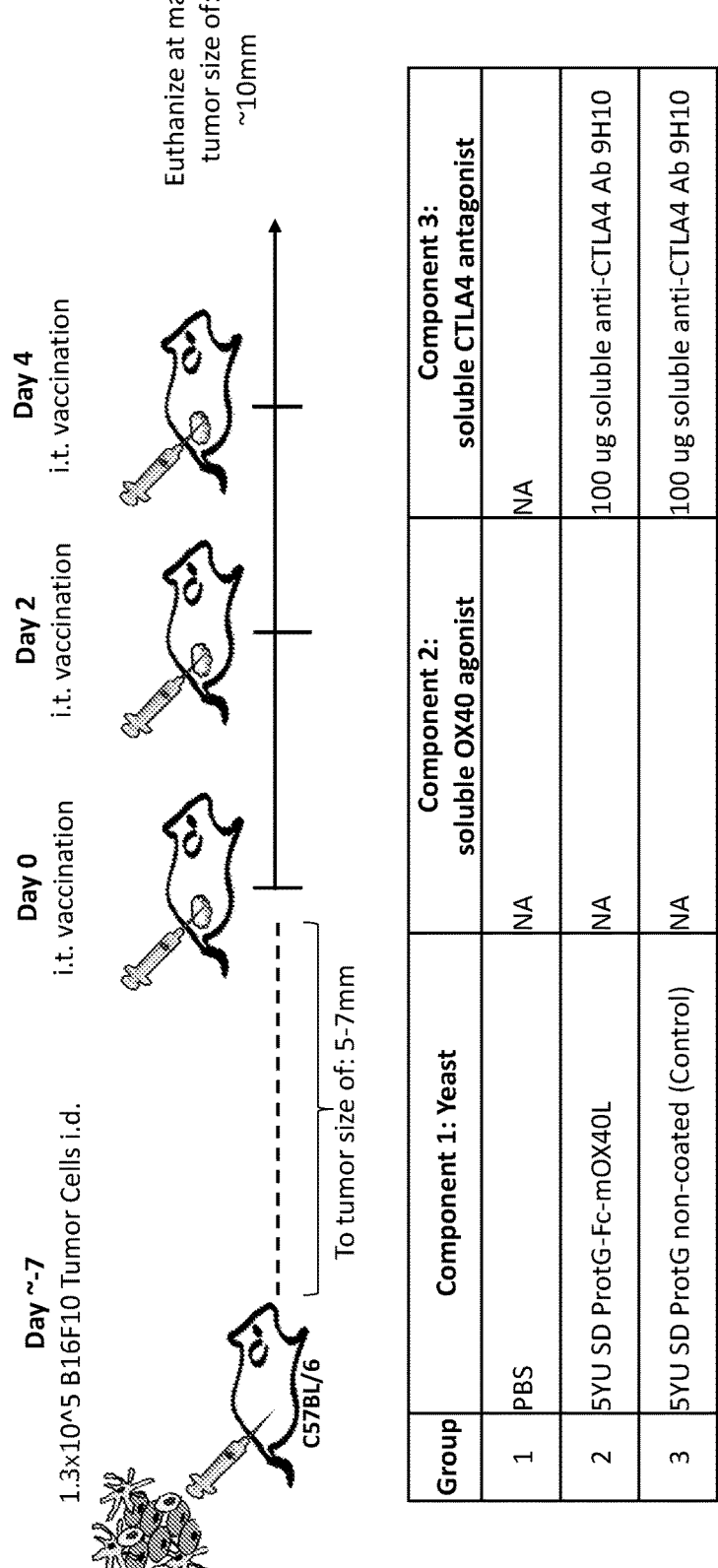

| Group | Component 1: Yeast | Component 2: soluble OX40 agonist | Component 3: soluble CTLA4 antagonist |
|---|---|---|---|
| 1 | PBS | NA | NA |
| 2 | 5YU SD ProtG-Fc-mOX40L | NA | 100 ug soluble anti-CTLA4 Ab 9H10 |
| 3 | 5YU SD ProtG non-coated (Control) | NA | 100 ug soluble anti-CTLA4 Ab 9H10 |
| 4 | 5YU Control (empty vector) Yeast | 258 ng soluble Fc-OX40L (low) | 100 ug soluble anti-CTLA4 Ab 9H10 |
| 5 | 5YU Control (empty vector) Yeast | 29,667 ng Fc-OX40L ("high"; molar equiv. of 100 ug aOX40 Ab in group 6) | 100 ug soluble anti-CTLA4 Ab 9H10 |
| 6 | 5YU Control (empty vector*) Yeast | 100 ug anti-OX40 Ab | 100 ug soluble anti-CTLA4 Ab 9H10 |

* Empty vector yeast is parental strain EBY100 carrying empty plasmid vector pRS424

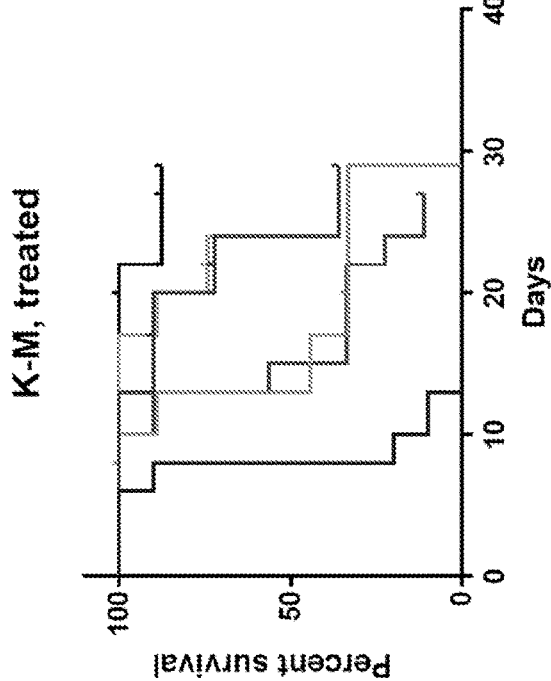
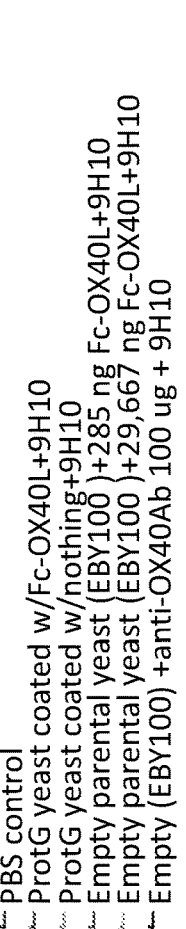
Fig. 6J
K-M, treated
Percent survival
Days
—+— PBS control
—+— ProtG yeast coated w/Fc-OX40L+9H10
—‖‖— ProtG yeast coated w/nothing+9H10
—+— Empty parental yeast (EBY100 )+285 ng Fc-OX40L+9H10
—‖‖— Empty parental yeast (EBY100 )+29,667 ng Fc-OX40L+9H10
—+— Empty (EBY100) +anti-OX40Ab 100 ug + 9H10
**** all treated groups vs PBS
p=0.025: coated with Fc-OX40L vs coated with nothing
*Coated vs free low Fc-OX40L
*free low vs high Untreated tumor-3060 coated with nothing (ctrl) + 9H10

Untreated tumor-3060 coated with mFc-OX40L + 9H10

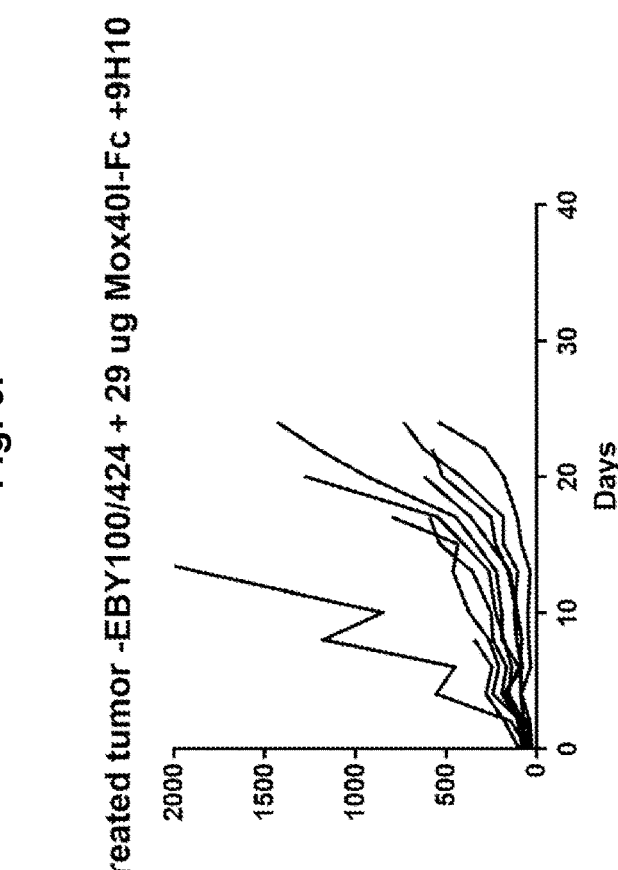
Fig. 6P
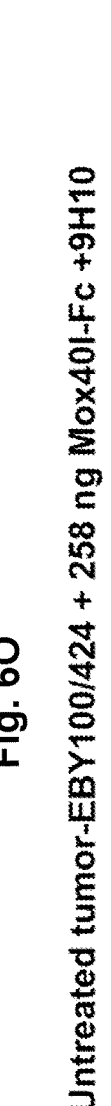
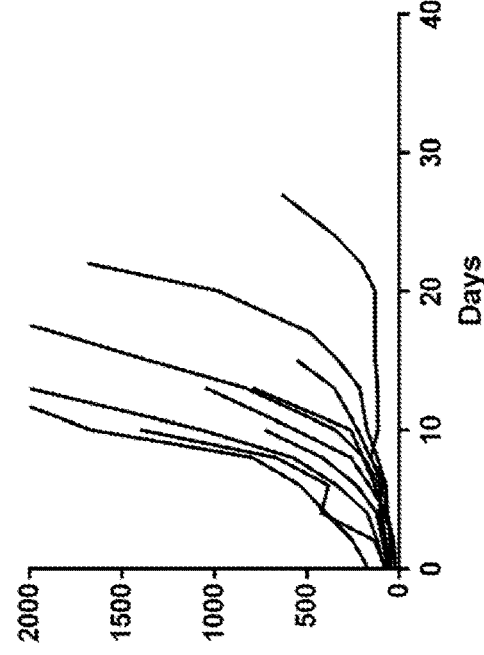
Fig. 6O

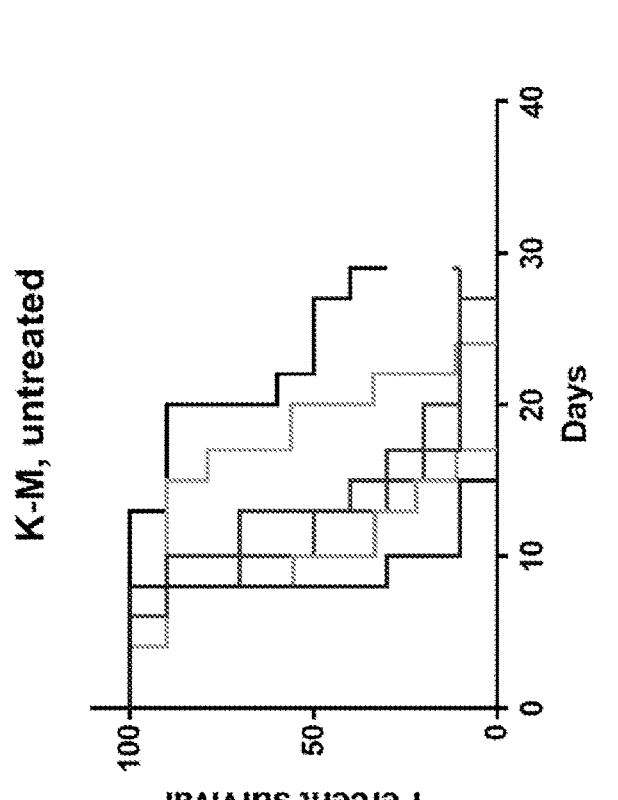
Fig. 6Q
K-M, untreated
Percent survival
Days
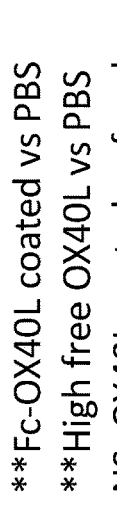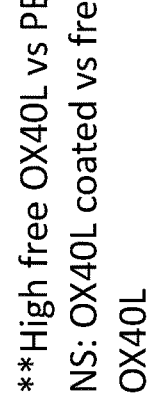
**Fc-OX40L coated vs PBS
**High free OX40L vs PBS
NS: OX40L coated vs free low OX40L
NS: free low vs high
⊢ PBS control
⊢ ProtG yeast coated w/Fc-OX40L+9H10
⊢ ProtG yeast coated w/nothing+9H10
⊢ Empty parental yeast (EBY100)+285 ng Fc-OX40L+9H10
⊢ Empty parental yeast (EBY100)+29,667 ng Fc-OX40L+9H10
⊢ Empty (EBY100)+anti-OX40Ab 100 ug + 9H10

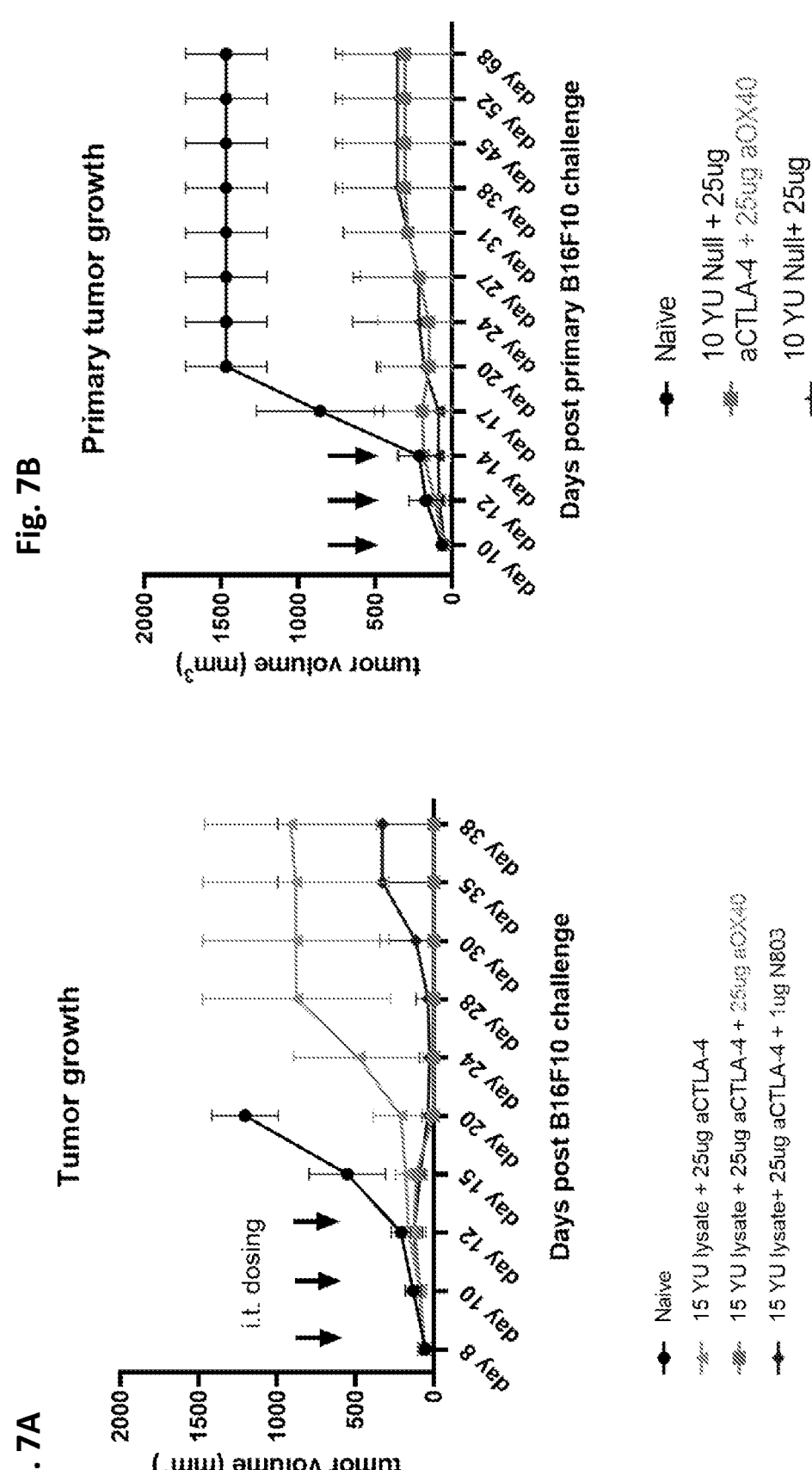

100ug aPDL1/aOX40

Tumor volume (mm³)

Days post enrollment

25ug aPDL1/aOX40

Tumor volume (mm³)

Days post enrollment

100ug aPDL1/aOX40
+5YU yeast pL

25ug aPDL1/aOX40
+5YU yeast pL

100ug aPDL1/aOX40
+ 5YU yeast pL

25ug aPDL1/aOX40
+5YU yeast pL

Fig. 9A

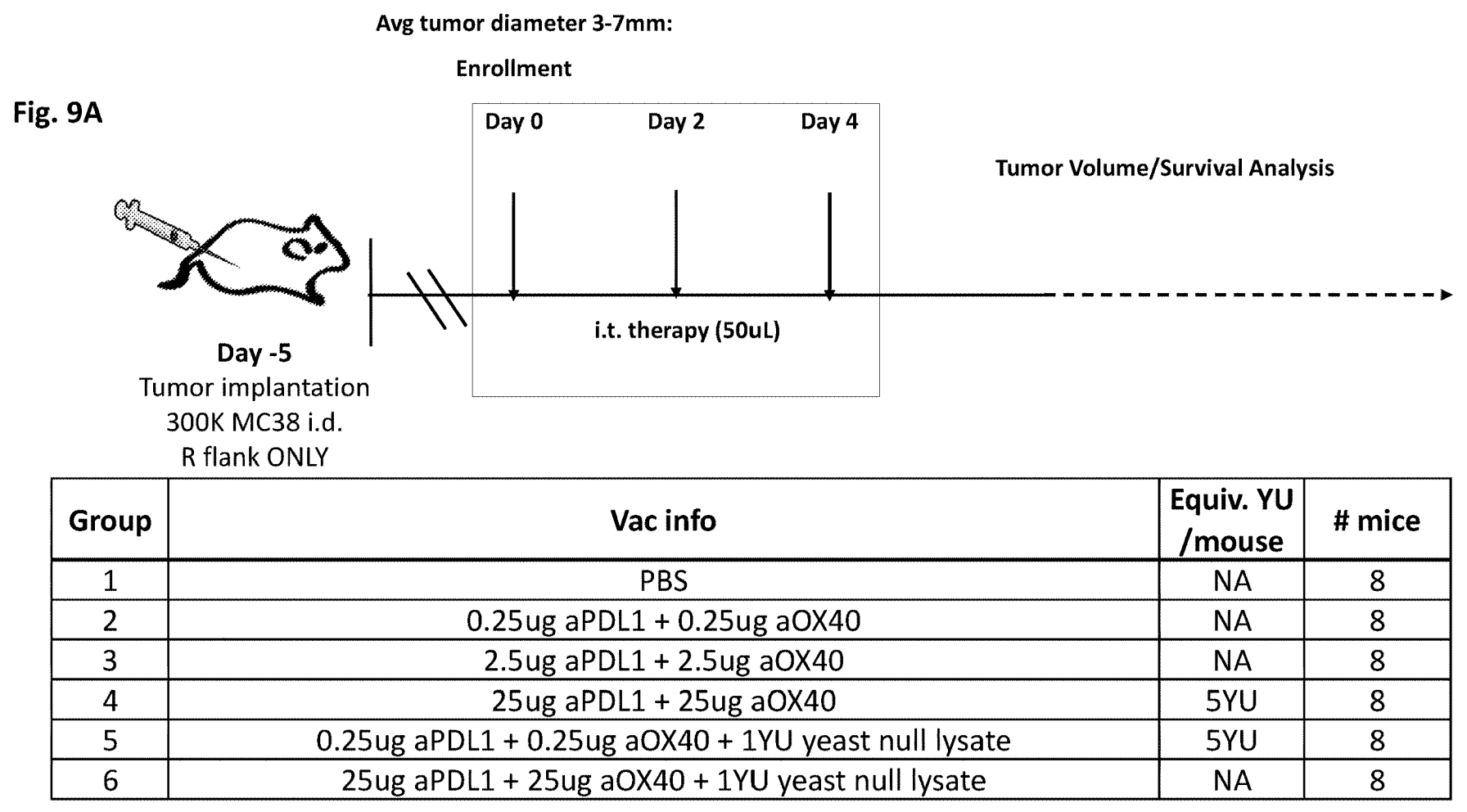

Avg tumor diameter 3-7mm:

Enrollment

Tumor Volume/Survival Analysis

| Day 0 | Day 2 | Day 4 |
| --- | --- | --- | i.t. therapy (50uL)

Day -5
Tumor implantation
300K MC38 i.d.
R flank ONLY

| Group | Vac info | Equiv. YU /mouse | # mice |
| --- | --- | --- | --- |
| 1 | PBS | NA | 8 |
| 2 | 0.25ug aPDL1 + 0.25ug aOX40 | NA | 8 |
| 3 | 2.5ug aPDL1 + 2.5ug aOX40 | NA | 8 |
| 4 | 25ug aPDL1 + 25ug aOX40 | 5YU | 8 |
| 5 | 0.25ug aPDL1 + 0.25ug aOX40 + 1YU yeast null lysate | 5YU | 8 |
| 6 | 25ug aPDL1 + 25ug aOX40 + 1YU yeast null lysate | NA | 8 |

Fig. 10A

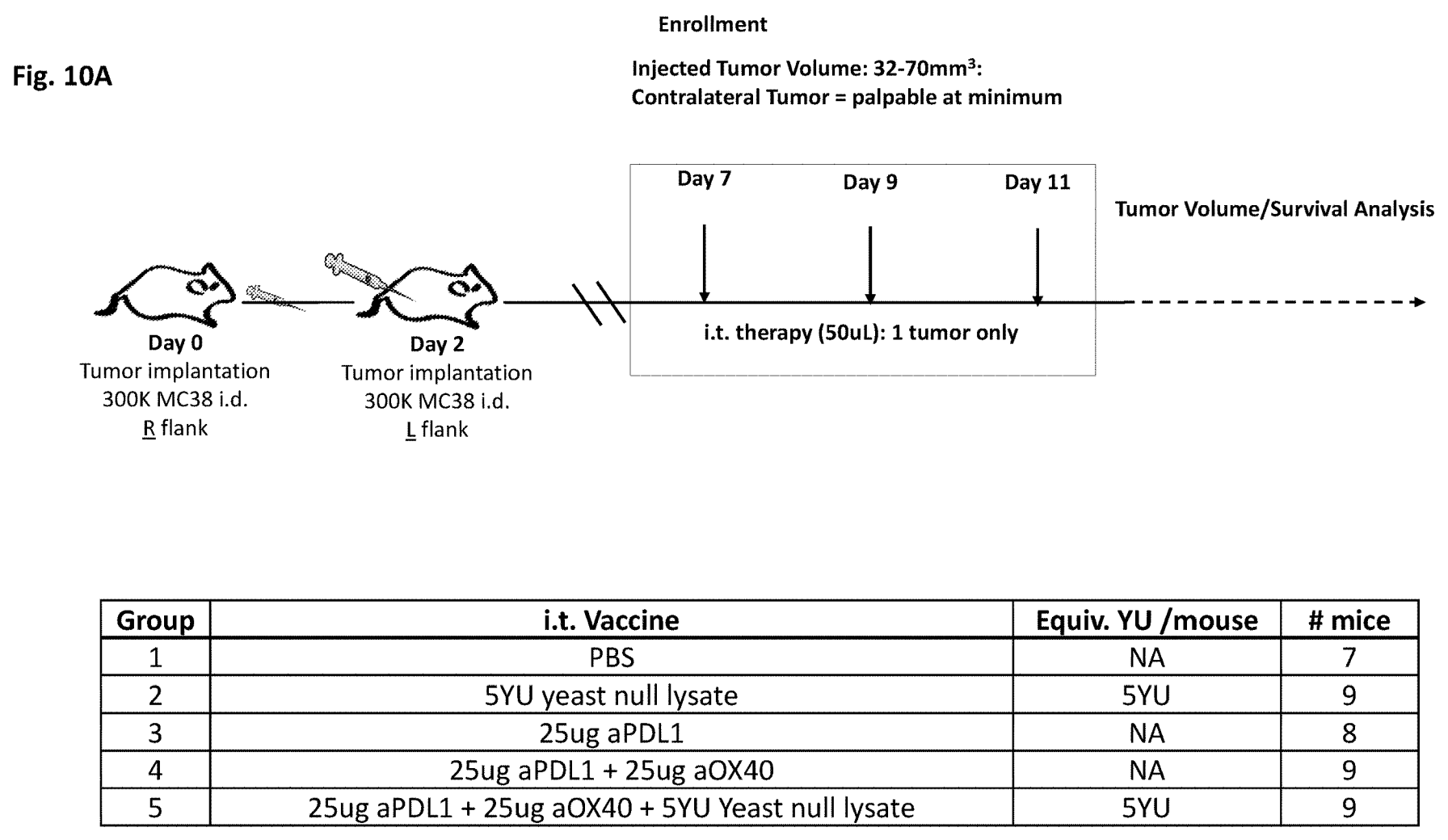

Enrollment

Injected Tumor Volume: 32-70mm³:
Contralateral Tumor = palpable at minimum

Day 0
Tumor implantation
300K MC38 i.d.
R flank

Day 2
Tumor implantation
300K MC38 i.d.
L flank

Day 7    Day 9    Day 11 i.t. therapy (50uL): 1 tumor only

Tumor Volume/Survival Analysis

| Group | i.t. Vaccine | Equiv. YU /mouse | # mice |
|-------|--------------|------------------|--------|
| 1 | PBS | NA | 7 |
| 2 | 5YU yeast null lysate | 5YU | 9 |
| 3 | 25ug aPDL1 | NA | 8 |
| 4 | 25ug aPDL1 + 25ug aOX40 | NA | 9 |
| 5 | 25ug aPDL1 + 25ug aOX40 + 5YU Yeast null lysate | 5YU | 9 |

25ug αPDL1 TREATED

5YU yeast lysate TREATED

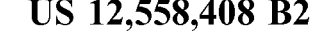
Fig. 10F
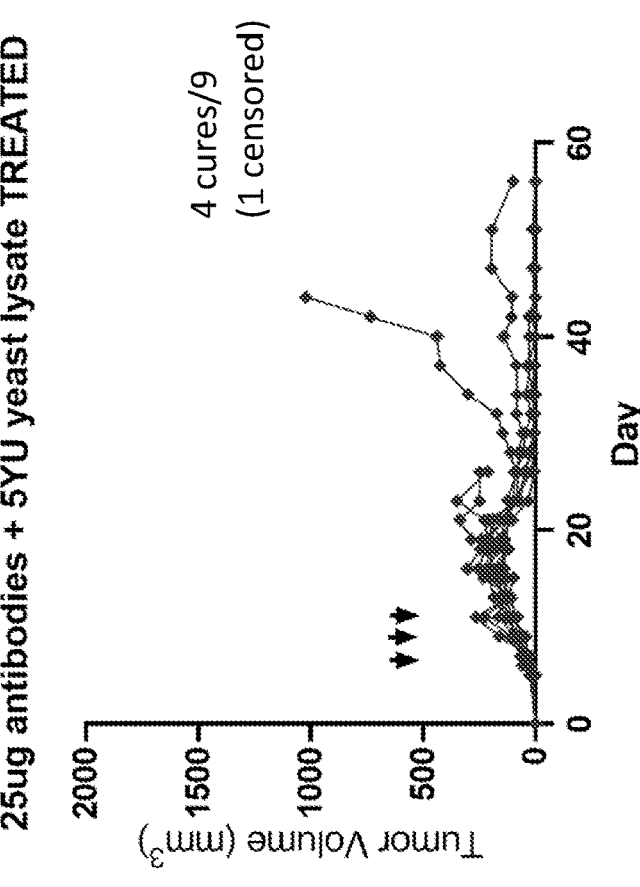
Fig. 10E
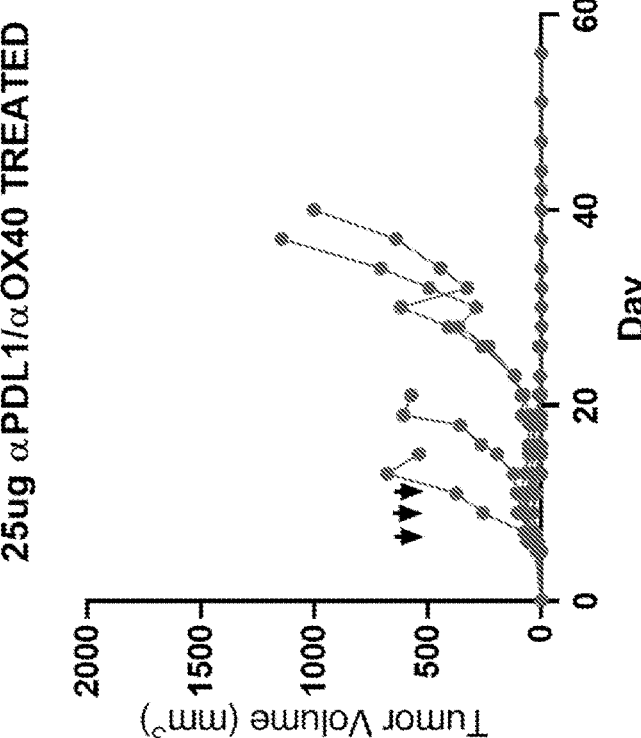

25ug αPDL1 - UNTREATED 2 cures/8

5YU yeast lysate - UNTREATED

Fig. 11B

| Group | n | Treatment | | | | ROUTE |
| | | a-CTLA4-7 | a-PD-L-1 | N-803 | W303α | |
|---|---|---|---|---|---|---|
| 1 | 10 | 0 | 0 | 0 | PBS | IT |
| 2 | 10 | 100 ug | 100ug | 2ug | W303 INT 5 yu | IT |
| 3 | 10 | 50 ug | 50 ug | 2ug | W303 INT 5 yu | IT |
| 4 | 10 | 25 ug | 25 ug | 2ug | W303 INT 5 yu | IT |
| 5 | 10 | 12.5 ug | 12.5 ug | 2ug | W303 INT 5 yu | IT |
| 6 | 10 | 50 ug | 50 ug | 2ug | W303CL 5 yu | IT |
| 7 | 10 | 50 ug | 50 ug | 2ug | W303INT 5 yu | IP for antibodies, sc for yeast and N-803 |

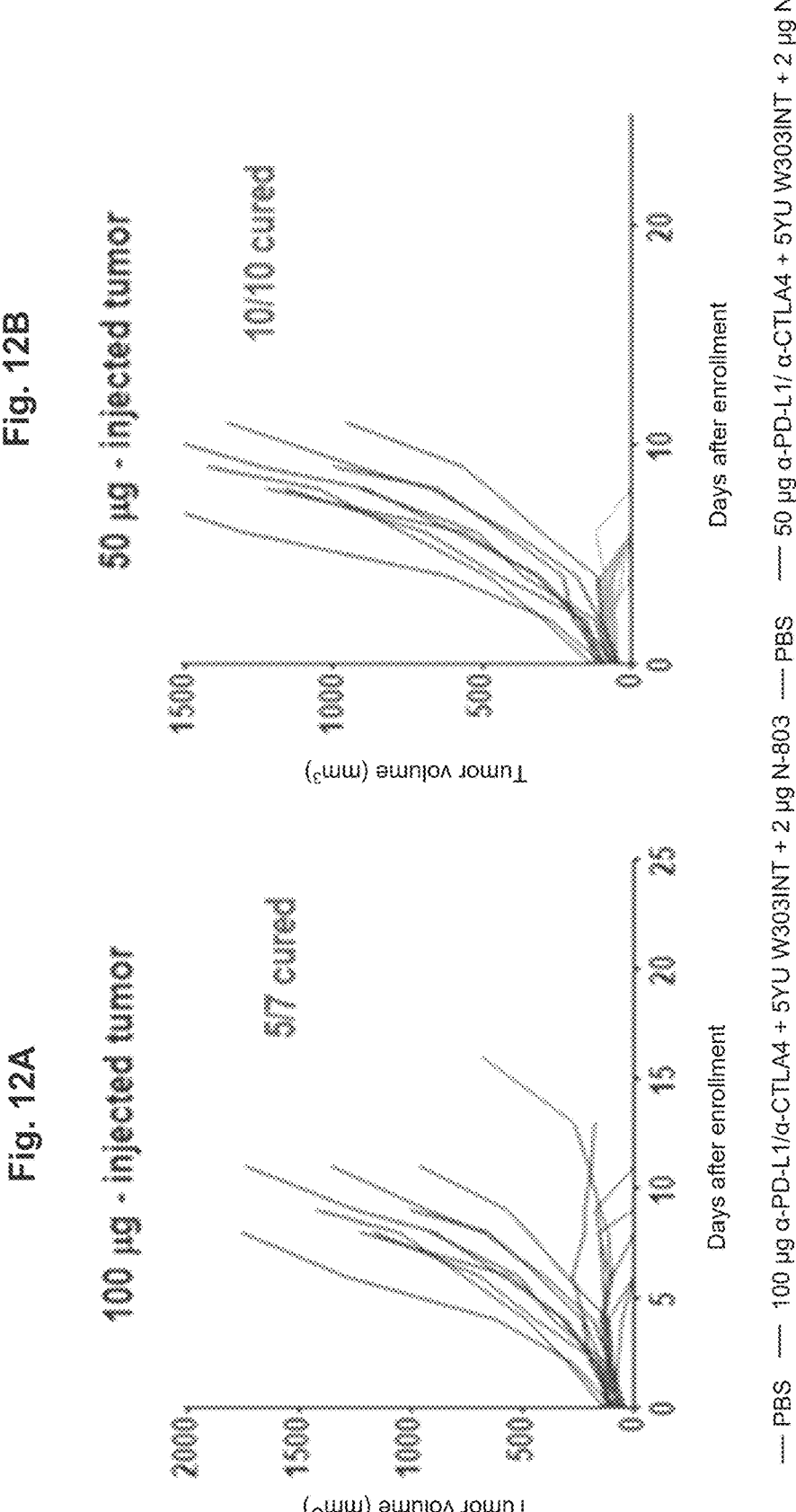

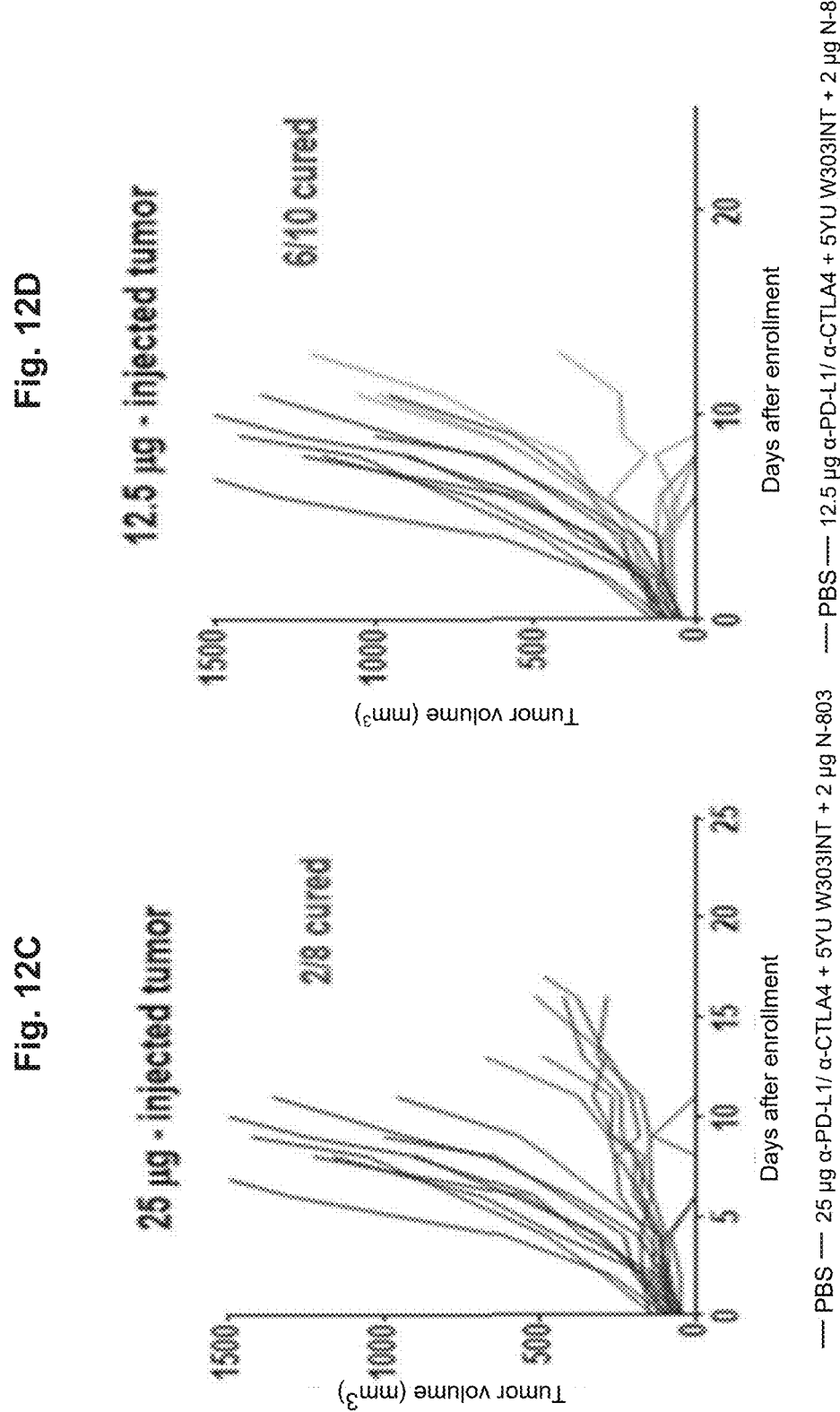

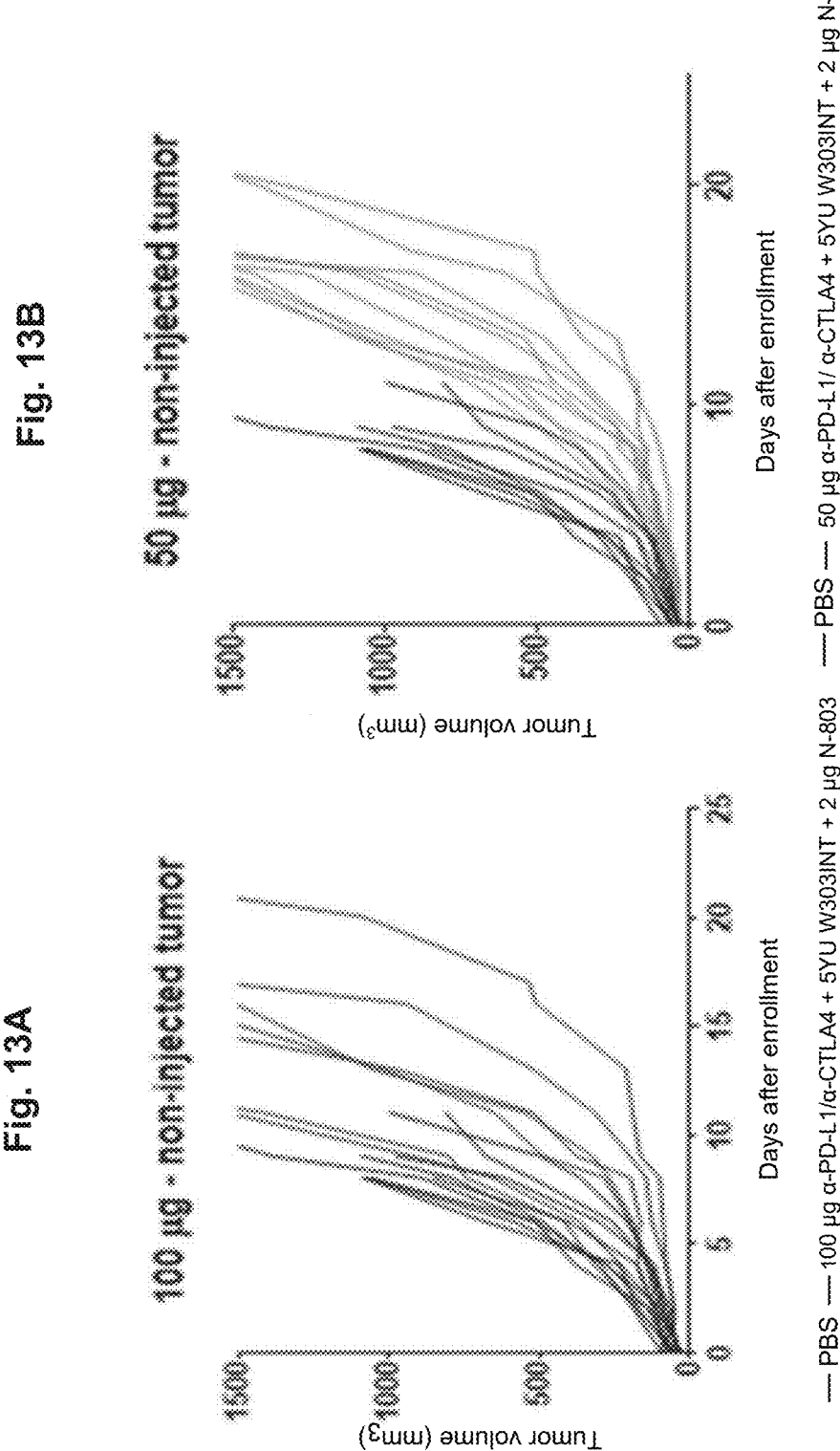

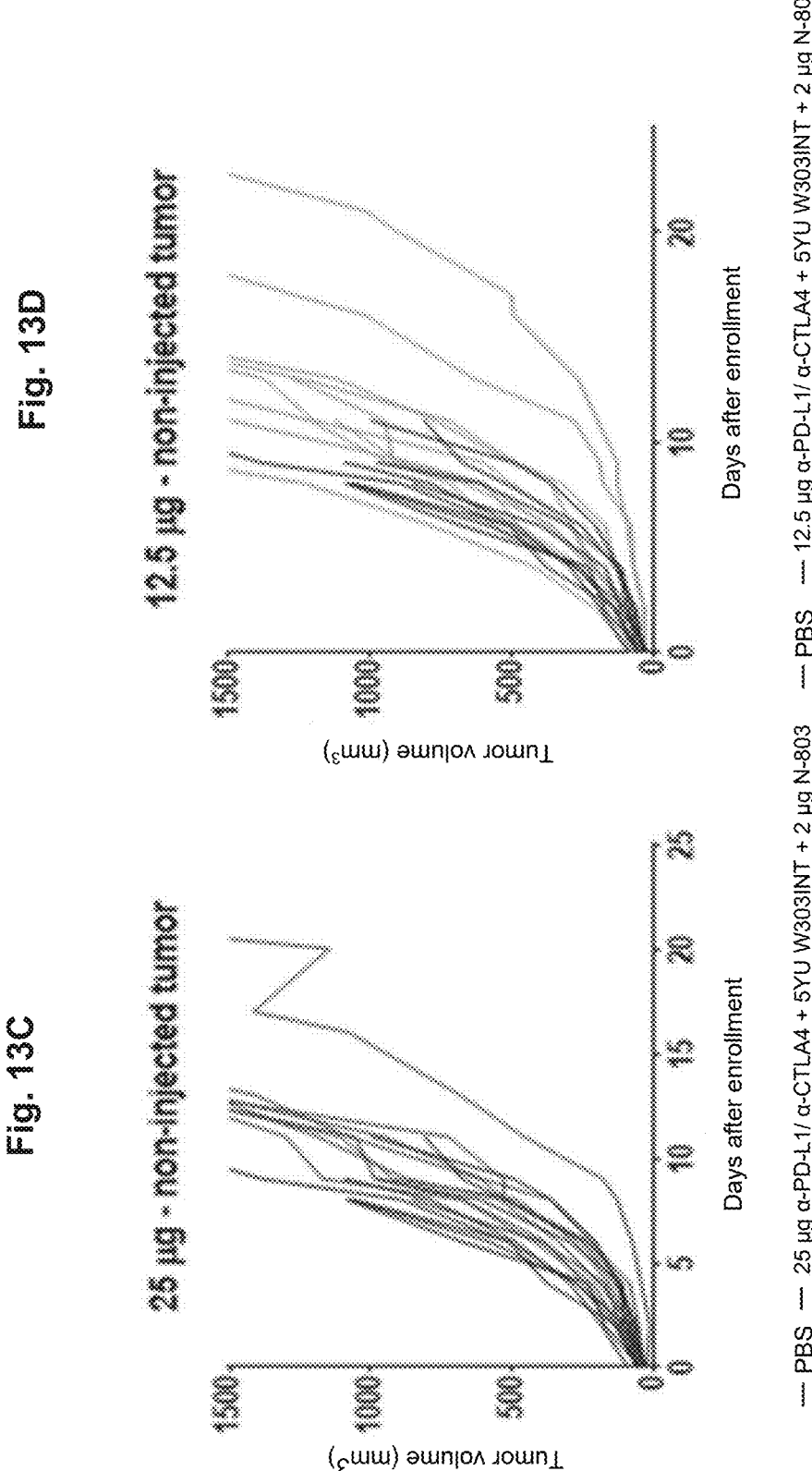

INT vs CL - non-injected tumor

INT vs CL - non-injected tumor

Tumor volume (mm³)

Days after enrollment

— PBS
— 50 μg α-PD-L1/α-CTLA4 + 5YU W303CL+2μg N~803
⋯ 50 μg α-PD-L1/α-CTLA4 + 5YU W303INT+2μg N~803 i.p./s.c. Vs i.t. - non-injected tumor i.p./s.c. Vs i.t. - injected tumor

AS-062:

Avg tumor diameter ~5-7mm: Enrollment

Day -7
Tumor implant-R & L flank
300K MC38 i.d.

Day 0   Day 2   Day 4 i.t. therapy (50uL)
1 tumor

Tumor Volume/Survival Analysis

| Group | Vac info | Equiv. YU /mouse | # mice |
|---|---|---|---|
| 1 | PBS | NA | 10 |
| 2 | 25ug PD-L1 + 2ug N-803 | NA | 10 |
| 3 | 25ug PD-L1 + 2ug N-803 + 5YU INT Yeast | 5YU | 10 |
| 4 | 25ug PD-L1 + 2ug N-803+ 5YU pL Yeast | 5YU | 10 |
| 5 | 25ug PD-L1 + 2ug N-803+ 5YU CL Yeast | 5YU | 10 |
| 6 | 25ug PD-L1 + 2ug N-803+ 2.5YU INT + 2.5YU CL Yeast | 5YU | 10 |

PD-L1 + N803 + 2.5 YU Int yeast + 2.5 YU cleared lysate

Fig. 24E

PD-L1 + N803 + 2.5 YU Int yeast + 2.5 YU cleared lysate

INTRATUMORALLY INJECTED YEAST VACCINE

CROSS-REFERENCE TO RELATED APPLICATIONS

This application claims the benefit of priority under 35 U.S.C. § 119(e) to U.S. Provisional Application Ser. No. 63/317,628, filed Mar. 8, 2022. The entire disclosure of U.S. Provisional Application Ser. No. 63/317,628 is incorporated herein by reference in its entirety.

BACKGROUND

Cancer is a leading cause of death worldwide, and the development of effective therapies for cancer continues to be one of the most active areas of research and clinical development. Although a variety of innovative approaches to treat and prevent cancers have been proposed, many cancers continue to have a high rate of mortality and may be difficult to treat or relatively unresponsive to conventional therapies. Thus, there remains a need for effective cancer therapies.

SUMMARY

One embodiment relates to a composition for injection into a solid tumor, wherein the composition comprises effective amounts of a yeast and/or a lysate thereof, a checkpoint inhibitor selected from the group consisting of an anti-CTLA-4 antibody and an anti-PDL1 antibody, and an immunostimulatory protein selected from the group consisting of an OX40 receptor agonist, a CD40 receptor agonist, and an IL-15 super agonist.

Another embodiment relates to a method of treating a solid tumor, the method comprising intratumoral injection of an effective amount of a composition comprising a yeast and/or a lysate thereof, a checkpoint inhibitor selected from a group consisting of an anti-CTLA-4 antibody and an anti-PDL1 antibody, and an immunostimulatory protein selected from a group consisting of an O×40 receptor agonist, a CD40 receptor agonist, and an IL-15 super agonist.

In one aspect of any of the embodiments, the yeast is *Saccharomyces cerevisiae*.

In still another aspect of any of the embodiments, the yeast is genetically engineered to express a tumor associated antigen, tumor specific antigen, or a neoepitope.

In one aspect of any of the embodiments, the O×40 or CD40 receptor agonist is a monoclonal antibody or a receptor ligand.

In still another aspect of any of the embodiments, the tumor is mucosal, melanoma, lung or colorectal.

In yet another aspect of any of the embodiments, the tumor is metastatic.

In another aspect of any of the embodiments, wherein the yeast are genetically engineered to express protein G on the surface of the yeast.

In another aspect of any of the embodiments, the O×40 or CD40 receptor agonist is an Fc-agonist fusion protein, and wherein the Fc-agonist fusion protein is bound to the yeast prior to administration.

In yet another aspect of any of the embodiments, the yeast is genetically engineered to express the immunostimulatory protein.

In yet another aspect of any of the embodiments, the IL-15 is nogapendekin-alfa-inbakicept (NAI which is also referred to herein as "N-803")

DESCRIPTION OF THE DRAWINGS

FIGS. 1A and 1B shows tumor volume to day 14 post-challenge (p.c.) treated tumor (FIGS. 1A-1D) and untreated tumor (FIGS. 1E-1H).Statistics, one way ANOVA on day 10. FIGS. 1I-1J show a Kaplan-Meier survival analysis to day 28 p.c. Statistics, one way ANOVA (tumor volume) or Log-rank (K-M); *, p<0.001; ** p<0.0001.

FIG. 3A shows tumor growth rates of primary tumor, with complete response rates of 8/9 and 7/8 mice for intact and lysed yeast, respectively. FIG. 3B shows complete responders were re-challenged on day 43 with 130,000 B16F10 tumor cells and growth was monitored for 94 additional days. An additional exploratory group of 5 naive mice was subcutaneously vaccinated with 2.5 YU of intact and 2.5 YU of pressure homogenized pTK170 yeast, with 25 µg of each antibody concurrently delivered intraperitoneally (gray). Statistics by 2 way ANOVA with Dunett's multiple comparison for: FIG. 3A, p<0.0001, intact and lysate groups compared to PBS from day 8 onward; FIG. 3B, intact and lysate group compared to Naive from day 21 onward.

FIG. 5A shows tumor growth rate (volume) through day 52 post treatment. FIG. 5B show Kaplan-Meier survival plot for the same time period.

FIGS. 6A, 6B, 6C, 6D, 6E, 6F, 6G, 6H, 6I, 6J, 6K, 6L, 6M, 6N, 6O, 6P, and 6Q show intratumoral injection of yeast displaying Fc-OX40L. FIGS. 6A-6B: yeast were engineered to express surface displayed protein G, which binds any Fc-containing protein, in this case Fc-OX40L. FIG. 6A, schematic of the strain; FIG. 6B, flow cytometric analysis. FIG. 6C, shows the intratumoral injection regimen and treatment groups. Effects of the treatment on tumor growth and survival for treated (FIGS. 6D-6J) and untreated (FIGS. 6K-6Q) tumors are shown. For both FIGS. 6D-6I and 6K-6P the spider plots show tumor growth for individual mice and Kaplan-Meier curves (FIG. 6J and FIG. 6Q) show survival. Statistics by log-rank, **p<0.01 for indicated comparisons. EBY100, parental yeast strain; 424, empty yeast expression plasmid; Mox40L-Fc, murine OX40L fused to IgG1 Fc.

FIGS. 7A and 7B show N803 can replace αOX40 in the B16F10 intratumoral injection assay. Tumor growth of injected (primary) tumors was monitored for 38 days (FIG. 7A) or 68 days (FIG. 7B).

FIGS. 8A-8E: primary tumor growth was monitored for 42 days. On day 45, complete responders were re-challenged intradermally on the contralateral (left) flank with 300,000 MC38 tumor cells and tumor volume (FIGS. 8F-8J) and survival (FIG. 8K) were monitored for 48 additional days. W303a pL, pressure homogenized yeast null lysate. Arrows indicate i.t. injection.

FIGS. 9A and 9B show titration of anti-PDL1/anti-OX40 antibodies for intratumoral therapy of MC38 tumors. Female C57BL/6 mice were intradermally implanted (see schematic FIG. 9A). Survival was monitored for 48 days, (FIG. 9B). W303a=yeast null; pL=pressure lysate. Statistics: Mantel-Cox test * compared to PBS; A comparison to group with same dose of antibodies but lacking yeast pL. i.t. injection indicated by arrows/

FIGS. 10A, 10B, 10C, 10D, 10E, 10F, 10G, 10H, 10I, 10J, 10K, and 10L. Strong therapeutic effect of αPDL1/αOX40+ Yeast Lysate intratumoral therapy in a bilateral MC38 implantation model. Female C57BL/6 mice were intradermally implanted (see FIG. 10A). Growth impairments for (FIGS. 10B-10F) treated and (FIGS. 10G-10K) untreated tumors are shown, with cure rates indicated. (FIG. 10L) Kaplan-Meier curves showing overall survival to day 58 post challenge (collective data, treated and untreated tumors). Death events (sacrifice) were recorded when a single tumor reached 1000 mm$^3$ or the combined treated and untreated tumor volume reached 1500 mm$^3$. Statistics by Mantel-Cox test for treatment groups relative to PBS: , P<0.01; **, P<0.0001.

FIGS. 11A and 11B: FIG. 11A shows the experimental schematic of an intratumoral (IT) injection assay model for the evaluation of anti-CTLA4 (in FIG. 11B as "a-CTLA4-7"), anti-PD-L 1 (in FIG. 11B as "a-PD-L-1"), N-803 and Yeast (in FIG. 11B "W303a") in a two-tumor IT B16.F10 mouse model. FIG. 11B shows a chart of the amounts of each treatment and route of administration.

FIGS. 12A, 12B, 12C, 12D, 12E, and 12F show injected tumors are eliminated following injection with 50 μg of anti-CTLA4, anti-PD-L1, N-803 and Yeast using the IT assay model disclosed in FIGS. 11A-11B.

FIGS. 13A, 13B, 13C, 13D, 13E, and 13F show that IT injection of anti-CTLA4, anti-PD-L1, N-803 and Yeast delayed tumor growth of non-injected distal tumors using the IT assay model disclosed in FIGS. 11A-11B.

FIGS. 24A, 24B, 24C, 24D, and 24E show the results on the growth delay of non-injected tumors using the assay and formulations shown in FIGS. 22A and 22B.

DETAILED DESCRIPTION

Figures 1A, 1B, 1C, 1D:
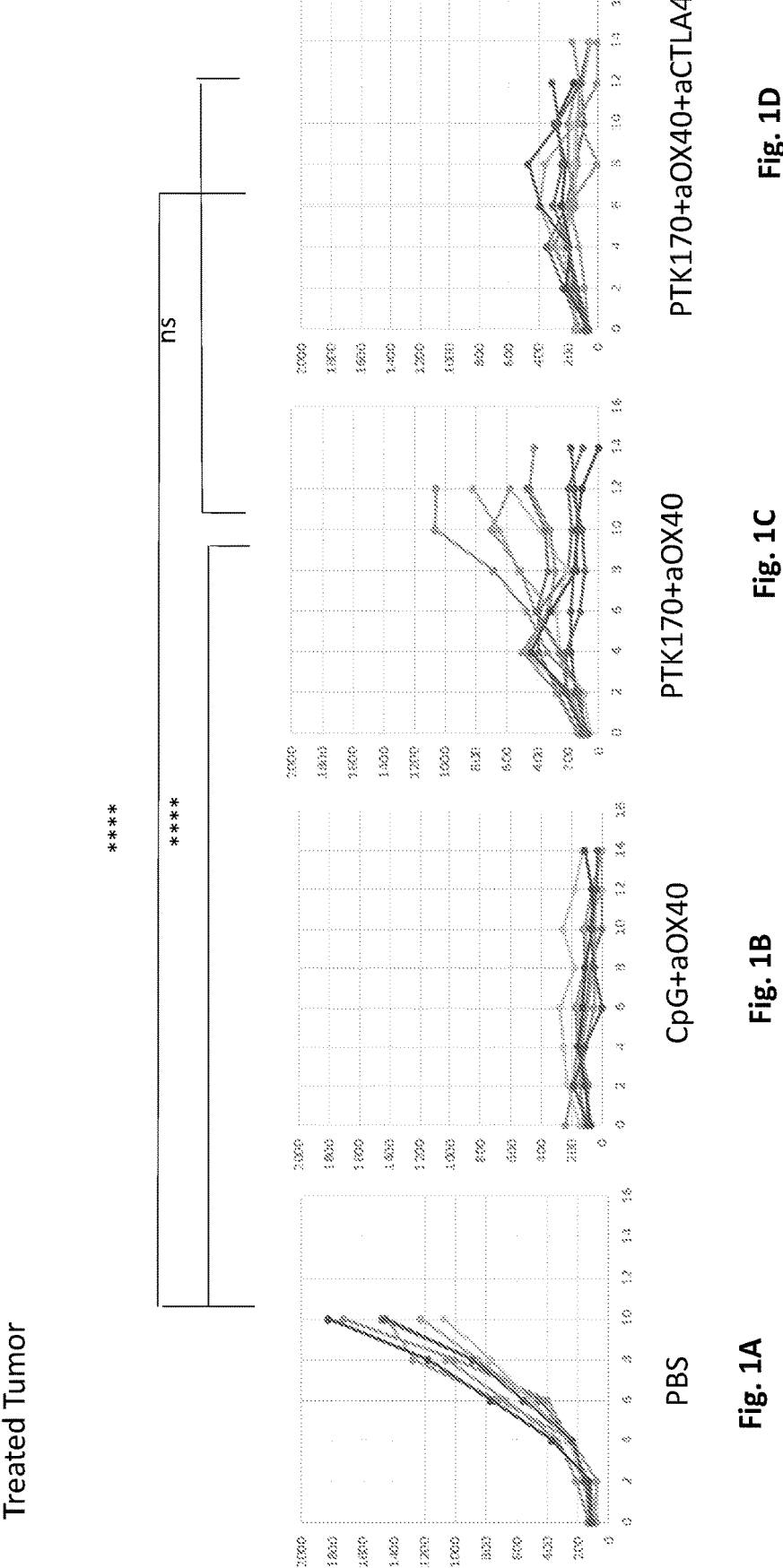
FIGS. 1A, 1B, 1C, 1D, 1E, 1F, 1G, 1H, 1I, and 1J show an anti-CTLA-4 antibody improves the antitumor activity of (yeast+aOX40) therapy.
Figures 1E, 1F, 1G, 1H:
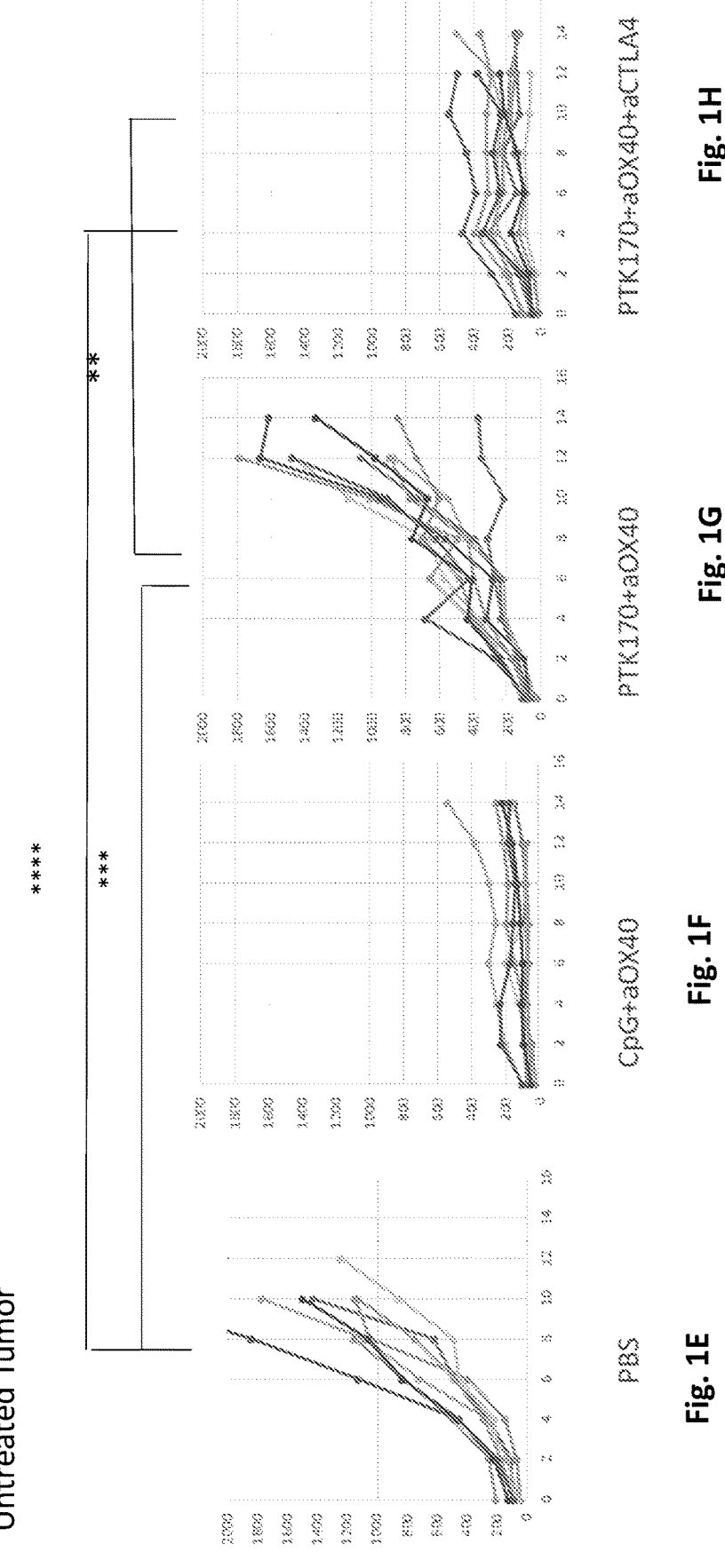
Figures 1I, 1J:
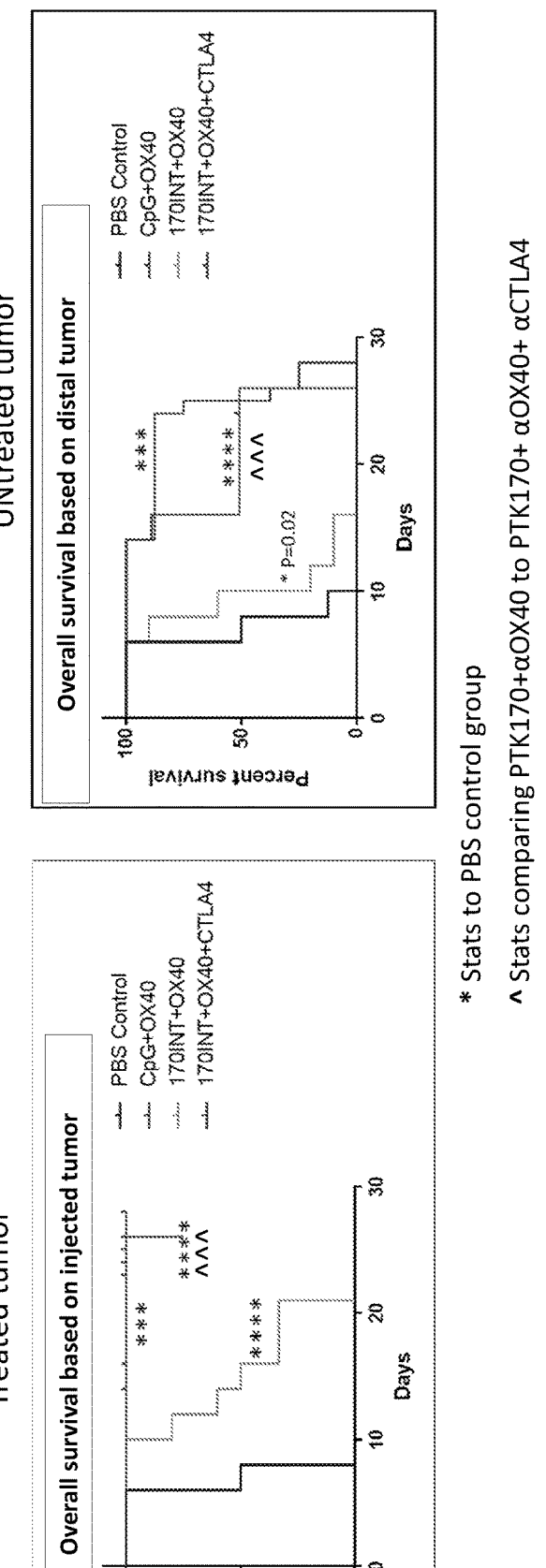

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry are those well-known and commonly used in the art.

All publications, patents, and published patent applications referred to in this application are specifically incorporated by reference herein. In case of conflict, the present specification, including its specific definitions, will control.

Throughout this specification, "comprise" or variations such as "comprises" or "comprising" imply the inclusion of a stated integer (or components) or group of integers (or components), but not the exclusion of any other integer (or component) or group of integers (or components).

The singular forms "a," "an," and "the" include the plurals unless the context clearly dictates otherwise.

"Including" means "including but not limited to." "Including" and "including but not limited to" are used interchangeably.

"Pharmaceutically acceptable carrier" refers to a non-toxic carrier that may be administered to a patient—together with compositions described herein—and which does not destroy the pharmacological activity of the active agents within the composition. "Excipient" refers to an additive in a formulation or composition that is not a pharmaceutically active ingredient.

"Peptide" and "polypeptide" are used synonymously herein to refer to polymers constructed from amino acid residues. "Amino acid residue" as used herein refers to any naturally occurring amino acid (L or D form), non-naturally occurring amino acid, or amino acid mimetic (such as peptide monomer).

"Identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window. The degree of amino acid or nucleic acid sequence identity for purposes of the present disclosure is determined using the BLAST algorithm, described in Altschul et al. (1990) *J Mol. Biol.* 215:403-10. This algorithm identifies high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul et al., (1990)*J Mol. Biol.* 215:403-10). Initial neighborhood word hits act as seeds for initiating searches to find longer HSPs containing them. The word hits are then extended in both directions along each sequence for as far as the cumulative alignment score can be increased. Cumulative scores are calculated for nucleotides sequences using the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For determining the percent identity of an amino acid sequence the BLASTP settings are: word length (W), 3; expectation (E), 10; and the BLOSUM62 scoring matrix. For analysis of nucleic acid sequences, the BLASTN program settings are word length (W), 11; expectation (E), 10; M=5; N=−4; and a comparison of both strands. The TBLASTN program (using a protein sequence to query nucleotide sequence databases) uses a word length (W) of 3, an expectation (E) of 10, and a BLOSUM 62 scoring matrix. (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873-87). The smallest sum probability (P(N)), provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01.

Unless otherwise specified, each embodiment disclosed herein may be used alone or in combination with any one or more other embodiments herein.

Disclosed herein are compositions for injection into a solid tumor as well as methods for treating a solid tumor.

One embodiment relates to a composition for injection into a solid tumor, wherein the composition comprises effective amounts of a yeast and/or a lysate thereof, a checkpoint inhibitor selected from the group consisting of an anti-CTLA-4 antibody and an anti-PDL1 antibody, and an immunostimulatory protein selected from the group consisting of an Ox40 receptor agonist, a CD40 receptor agonist, and an IL-15 super agonist.

One embodiment relates to a method of treating a solid tumor, the method comprising intratumoral injection of an effective amount of a composition comprising a yeast and/or a lysate thereof, a checkpoint inhibitor selected from a group consisting of an anti-CTLA-4 antibody and an anti-PDL1 antibody, and an immunostimulatory protein selected from a group consisting of an Ox40 receptor agonist, a CD40 receptor agonist, and an IL-15 super agonist.

Solid tumors are heterotypic aggregates of many cell types, including cancer cells, cancer stem cells, connective-tissue cells, and immune cells. All of these cells can communicate with one another via specific junctions (tight and gap junction) that maintain and regulate a perfect tumor microenvironment. Several scientific studies have shown that these different genetically designed tumors with acquired resistance could control complex cell-to-cell interactions and aberrant signaling pathways leading to genome instability. Tumor heterogeneity indicates a poor life survival prognosis. Examples of solid tumor cancers include, mucosal, melanoma, lung, colorectal, breast, bladder, and prostate. In one aspect, the tumor is mucosal, melanoma, lung or colorectal. In still another aspect, the tumor is metastatic.

A "TARMOGEN®" (GlobeImmune, Inc., Louisville, Colorado) generally refers to a yeast vehicle expressing one or more heterologous antigens extracellularly (on its surface), intracellularly (internally or cytosolically) or both extracellularly and intracellularly. TARMOGEN®s have been generally described (see, e.g., U.S. Pat. No. 5,830,463). Certain yeast-based immunotherapy compositions, and methods of making and generally using the same, are also described in detail, for example, in U.S. Pat. Nos. 5,830,463, 7,083,787, 7,736,642, Stubbs et al., *Nat. Med.* 7:625-629 (2001), Lu et al., *Cancer Research* 64:5084-5088 (2004), and in Bernstein et al., *Vaccine* 2008 Jan 24; 26(4):509-21, each of which is incorporated herein by reference in its entirety.

Compositions include a yeast, yeast vehicle and/or a yeast lysate. In one aspect, the yeast lysate is prepared from a yeast, wherein the lysate lacks yeast membranes and yeast cell walls. Such a yeast lysate is prepared from yeast that have been lysed, i.e., yeast in which the cell walls and membranes have been disrupted, exposing the yeast cell contents to the rest of the composition. The yeast lysates can be prepared from inactivated, such as heat inactivated, yeast or from live yeast. The yeast can contain a disease-related antigen expressed inside the yeast from a plasmid or from an integrated chromosomal allele. For example, yeast can be lysed by glass bead rupture, such as by mixing with PBS and 500 μL of acid washed 0.2 μm glass beads in a 1.5 mL total volume and vigorously shaking the mixture in a mechanical agitation machine until the cells are ruptured, such as >97% of the cells being ruptured. Alternatively, yeast can be lysed by other methods including high pressure homogenization, ultrasonication, and electrical, physical, chemical and enzymatic techniques. (See e.g. U.S. patent application Ser. No. 17/047,134).

In any of the yeast-based compositions used in the present invention, the following aspects related to the yeast vehicle are included in the invention. According to the present invention, a yeast vehicle is any yeast cell (e.g., a whole or intact cell) or a derivative thereof (see below) that can be used in conjunction with one or more antigens, immunogenic domains thereof or epitopes thereof in a therapeutic composition of the invention. The yeast vehicle can therefore include, but is not limited to, a live intact yeast microorganism (i.e., a yeast cell having all its components including a cell wall), a killed (dead) or inactivated intact yeast microorganism, or derivatives thereof including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle and previously as a subcellular yeast particle), any other yeast particle, or a yeast cell wall preparation.

Yeast spheroplasts are typically produced by enzymatic digestion of the yeast cell wall. Such a method is described, for example, in Franzusoff et al., 1991, Meth. Enzymol. 194, 662-674., incorporated herein by reference in its entirety.

Yeast cytoplasts are typically produced by enucleation of yeast cells. Such a method is described, for example, in Coon, 1978, Natl. Cancer Inst. Monogr. 48, 45-55 incorporated herein by reference in its entirety.

Yeast ghosts are typically produced by resealing a permeabilized or lysed cell and can, but need not, contain at least some of the organelles of that cell. Such a method is described, for example, in Franzusoff et al., 1983, J. Biol. Chem. 258, 3608-3614 and Bussey et al., 1979, Biochim. Biophys. Acta 553, 185-196, each of which is incorporated herein by reference in its entirety.

A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, Meth. Enzymol. 194, 662-674. One may also use fractions of yeast membrane particles that contain yeast membrane portions and, when the antigen or other protein was expressed recombinantly by the yeast prior to preparation of the yeast membrane particles, the antigen or other protein of interest. Antigens or other proteins of interest can be carried inside the membrane, on either surface of the membrane, or combinations thereof (i.e., the protein can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen or other protein of interest on the surface of the membrane or at least partially embedded within the membrane.

An example of a yeast cell wall preparation is isolated yeast cell walls carrying an antigen on its surface or at least partially embedded within the cell wall such that the yeast cell wall preparation, when administered to an animal, stimulates a desired immune response against a disease target.

For composition comprising lysed yeast cells, these compositions may then be further treated to remove yeast membranes and yeast cell walls by any suitable method to produce a yeast lysate lacking yeast membranes and yeast cell walls. For example, yeast membranes and yeast cell walls can be removed from lysed yeast by centrifugation to produce a lysate (supernatant), which is free of cell walls and membranes, such as by centrifugation of lysed yeast for 5 minutes at 16,000 rpm, 25° C. Alternatively, lysates can be cleared of cell wall and membranous debris after rupture by means other than centrifugation. For example, filtration or treatment of cells with conA beads are alternate methods. In an exemplary method, pressure lysate is centrifuged to pellet/remove the insoluble particulates, then the supernatant is filtered for sterilization. When referring to removing yeast membranes and yeast cell walls or reference is made to a lysate lacking yeast membranes and yeast cell walls, it will be recognized that suitable processes for removal of materials may not remove 100% of the yeast membranes and yeast cell walls from a lysate. Thus, in some instances, at least about 80% of the yeast membranes and/or yeast cell walls are removed, at least about 85%, at least about 90%, at least about 91%, at least about 92%, at least about 93%, at least about 94%, at least about 95%, at least about 96%, at least about 97%, at least about 98%, at least about 99%.

Compositions of the present invention, in addition to a yeast lysate lacking yeast membranes and yeast cell walls, comprise at least one antigen (which term includes immunogenic domains of antigens) that is heterologous to the yeast. The heterologous antigen can have been expressed by the yeast, such as prior to lysing the yeast if the yeast vehicle is a yeast lysate or the antigen can have been combined with the yeast either before or after lysing and before or after removal of yeast membranes and yeast cell walls from a lysate. In some embodiments, the antigen is provided as a fusion protein, which can include two or more antigens. An antigen may, in some embodiments, elicit an antigen-specific immune response (e.g., a humoral and/or a cell-mediated immune response) against the same or similar antigens that are encountered by an element of the immune system (e.g., T cells, antibodies). In one aspect, the fusion protein can include two or more immunogenic domains of one or more antigens, or two or more epitopes of one or more antigens. In one aspect, the yeast is genetically engineered to express a tumor associated antigen, tumor specific antigen, or a neoepitope.

The present invention includes the use of at least one "composition" (which phrase may be used interchangeably with "yeast-based immunotherapeutic composition", "yeast-based immunotherapy product", "yeast-based immunotherapeutic composition", "yeast-based composition", "yeast-based immunotherapeutic" or "yeast-based vaccine") which can be a yeast, yeast vehicle, or a yeast lysate that lacks yeast membranes and yeast cell walls, alone or in combination with an intact yeast-based immunotherapeutic composition, such as a TARMOGEN®. Yeast-based immunotherapeutic compositions elicit an immune response sufficient to achieve at least one therapeutic benefit in a subject. More particularly, a yeast-based immunotherapeutic composition is a composition that includes a yeast, yeast vehicle or a yeast lysate component alone or in combination with an intact yeast-based immunotherapeutic composition and can elicit or induce an immune response, such as a cellular immune response, including without limitation a T cell-mediated cellular immune response. In one aspect, the yeast-based immunotherapeutic composition useful in the invention is capable of inducing a CD8+ and/or a CD4+T cell-mediated immune response and in one aspect, a CD8+ and a CD4+T cell-mediated immune response. Optionally, a yeast-based immunotherapeutic composition is capable of eliciting a humoral immune response.

Yeast lysates can be made from intact yeast-based immunotherapy compositions (i.e., TARMOGEN®). In addition, such intact yeast-based immunotherapy compositions can be combined with a yeast lysate-based composition. Such intact yeast-based immunotherapy compositions generally comprise a yeast vehicle (which does not include in this case a yeast lysate) and an antigen heterologous to the yeast.

Such intact yeast-based immunotherapy compositions, and methods of making and generally using the same, are described in detail, for example, in U.S. Pat. Nos. 5,830,463, 7,083,787, 7,465,454, U.S. Patent Publication 2007-0224208, U.S. Patent Publication No. US 2008-0003239, and in Stubbs et al., Nat. Med. 7:625-629 (2001), Lu et al., Cancer Research 64:5084-5088 (2004), and in Bernstein et al., Vaccine 2008 Jan 24;26(4):509-21, each of which is incorporated herein by reference in its entirety. These yeast-based immunotherapeutic products have been shown to elicit immune responses, including cellular and humoral immune responses. Yeast-based immunotherapeutic products are capable of killing target cells expressing a variety of antigens in vivo, in a variety of animal species, and to do so via antigen-specific, CD4+ and CD8+ mediated immune responses. Additional studies have shown that yeast are avidly phagocytosed by and directly activate dendritic cells which then present yeast-associated proteins to CD4+ and CD8+ T cells in a highly efficient manner. See, e.g., Stubbs et al. Nature Med. 5:625-629 (2001) and U.S. Pat. No. 7,083,787.

Any yeast strain can be used to produce a yeast vehicle (either for production of a yeast lysate or to be used in combination with a yeast lysate). In one embodiment, the yeast is *Saccharomyces cerevisiae*. In another embodiment, the yeast is *Pichia Pastoris*.

A yeast vehicle of the present invention is capable of fusing with the cell type to which the yeast vehicle and antigen/agent is being delivered, such as a dendritic cell or macrophage, thereby effecting particularly efficient delivery of the yeast vehicle, and in many embodiments, the antigen(s) or other agent, to the cell type. As used herein, fusion of a yeast vehicle with a targeted cell type refers to the ability of the yeast cell membrane, or particle thereof, to fuse with the membrane of the targeted cell type (e.g., dendritic cell or macrophage), leading to syncytia formation. As used herein, a syncytium is a multinucleate mass of protoplasm produced by the merging of cells. A number of viral surface proteins (including those of immunodeficiency viruses such as HIV, influenza virus, poliovirus and adenovirus) and other fusogens (such as those involved in fusions between eggs and sperm) have been shown to be able to effect fusion between two membranes (i.e., between viral and mammalian cell membranes or between mammalian cell membranes). For example, a yeast vehicle that produces an HIV gp120/gp41 heterologous antigen on its surface is capable of fusing with a CD4+T-lymphocyte. It is noted, however, that incorporation of a targeting moiety into the yeast vehicle, while it may be desirable under some circumstances, is not necessary. In the case of yeast vehicles that express antigens extracellularly, this can be a further advantage of the yeast vehicles of the present invention. In general, yeast vehicles useful in the present invention are readily taken up by dendritic cells (as well as other cells, such as macrophages).

Expression of an antigen or other protein in a yeast or yeast vehicle of the present invention is accomplished using techniques known to those skilled in the art. Briefly, a nucleic acid molecule encoding at least one desired antigen or other protein is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens and/or other proteins can be on one or more expression vectors operatively linked to one or more expression control sequences. Particularly important expression control sequences are those which control transcription initiation, such as promoter and upstream activation sequences. Any suitable yeast promoter can be used in the present invention and a variety of such promoters are known to those skilled in the art.

In another aspect, an antigen and/or other agent is physically attached to the yeast or yeast vehicle. Physical attachment of the antigen and/or other agent to the yeast or yeast vehicle can be accomplished by any method suitable in the art, including covalent and non-covalent association methods which include, but are not limited to, chemically cross-linking the antigen and/or other agent to the outer surface of the yeast vehicle or biologically linking the antigen and/or other agent to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast or yeast vehicle that alters the charge of the lipid bilayer of yeast membrane or the composition of the cell wall so that the outer surface of the yeast is more likely to fuse or bind to antigens and/or other agent having particular charge characteristics. Targeting agents such as antibodies, binding peptides, soluble receptors, and other ligands may also be incorporated into an antigen as a fusion protein or otherwise associated with an antigen for binding of the antigen to the yeast or yeast vehicle.

In one aspect, the compositions disclosed herein comprise checkpoint inhibitors. Preferred checkpoint inhibitors include an anti-CTLA-4 antibody and an anti-PDL1 antibody.

In one aspect, the compositions disclosed herein comprise an immunostimulatory protein. Such proteins include, an OX40 receptor agonist, a CD40 receptor agonist and an IL-15 super agonist.

OX40 is a member of the tumor necrosis factor receptor super family (TN FRSF) and regulates multiple T-cell functions. The cell surface expression of OX40 is upregulated following T-cell activation; upon binding the OX40 ligand (OX40L), it provides costimulatory signals, increasing the activation of CD4$^+$ and CD8$^+$ T effector cells in preclinical studies (Aspeslagh, S, et al. Rationale for anti-OX40 cancer immunotherapy. *Eur J Cancer* 2016; 52:50-66; Jensen, S M., et al., Signaling through OX40 enhances antitumor immunity. Semin Oncol. 2010; 37:524-32; and Piconese S, et al., OX40 triggering blocks suppression by regulatory T cells and facilitates tumor rejection. J Exp med 2008; 205:825-39), OX40 may also inhibit regulatory T-cell—mediated suppression and block the generation of regulatory T cells, leading to enhanced T effector cell activity (Piconese 5, et al., 2008). Agonistic OX40 antibodies can trigger survival and proliferation of tumor antigen specific CD4 T cells.

CD40 (cluster of differentiation 40) is a co-stimulatory protein found on antigen-presenting cells and is required for their activation. CD40L (CD40 ligand) binds to CD40 on antigen presenting cells.

In one aspect, the OX40 or the CD40 receptor agonist is an Fc agonist fusion protein. In a preferred embodiment, the Fc agonist fusion protein is bound to the yeast prior to administration of the composition.

N-803 (also known as ALT-803 or nogapendekin-alfa-inbakicept (NAI)) is an IL-15-based immunostimulatory protein complex comprising two protein subunits of a human IL-15 variant associated with high affinity to a dimeric human IL-15 receptor a (IL-15Rα) sushi domain/human IgG1 Fc fusion protein. The IL-15 variant the mature human IL-15 cytokine sequence (114 amino acids), with an asparagine to aspartate substitution at position 72 (N72D). The human IL-15Ra sushi domain/human Fc fusion protein comprises the sushi domain of the human IL-15 receptor a subunit (IL-15Rα) (amino acids 1-65 of the mature human IL-15Ra protein) linked to the human IgG1 CH2-CH3 region containing the Fc domain (232 amino acids). Except for the N72D substitution, all of the protein sequences are human. N-803 is an IL-15 super agonist.

In one aspect, the yeast are genetically engineered to express protein G on the surface of the yeast. In still another aspect, the yest are genetically engineered to express the immunostimulatory proteins disclosed herein, such as OX40, OX40L, CD40 and CD40L. In yet another aspect, the yeast expressing protein G is bound to an immunostimulatory protein.

According to the methods provided herein, the subject is administered an effective amount(s), pharmaceutically effective amount(s) or therapeutically effective amount(s) of the compositions or component of the compositions provided herein. The terms effective amount(s), therapeutically effective amount(s), pharmaceutically effective amount(s) and effective dosage(s) are used interchangeably. The term effective amount is defined as any amount necessary to produce a desired physiologic response (e.g., reduction of tumor size, elimination of tumor; killing cells, and or preventing the growth of new cells,). Effective amounts and schedules for administering the compositions disclosed herein may be determined empirically by one skilled in the art. The dosage ranges for administration are large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 22nd Edition, Gennaro, Editor (2012), and Pickar, Dosage Calculations (1999)).

With respect to the compositions disclosed herein in general, a suitable single dose is a dose that is capable of effectively providing a composition of the invention to a given tumor in an amount effective to elicit an antigen-specific immune response, when administered one or more times over a suitable time period. For example, in one embodiment, a single dose of a composition of the present invention is from about $1 \times 10^5$ to about $5 \times 10^7$ yeast cell equivalents per kilogram body weight of the organism being administered the composition. In one aspect, a single dose of a yeast vehicle of the present invention is from about 0.1 Y.U. ($1 \times 10^6$ cells) to about 200 Y.U. ($2 \times 10^9$ cells) per dose (i.e., per organism), including any interim dose, in increments of $0.1 \times 10^6$ cells (i.e., $1.1 \times 10^6$, $1.2 \times 10^6$, $1.3 \times 10^6$ . . . ). In one aspect, doses include doses between 1 Y.U and 80 Y.U. and in one aspect, between 5 Y.U. and 40 Y.U. In one embodiment, the doses are administered via intratumoral injection 3 times, every 2 days.

"Boosters" or "boosts" of the compositions disclosed herein can be administered.

The terms subject, patient, individual, etc. are not intended to be limiting and can be generally interchanged. As used throughout, a subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient, individual and subject may be used interchangeably and these terms are not intended to be limiting. That is, an individual described as a patient does not necessarily have a given disease, but may be merely seeking medical advice. The terms patient or subject include human and veterinary subjects.

Reference herein to "therapeutic" is to be considered in their broadest contexts. "Therapeutic" does not necessarily imply that a mammal is treated until total recovery. As used herein, "treat," "treating," and similar words mean stabilizing and/or reducing the symptoms of a disease or condition. In some aspects, the compositions disclosed herein can cure a medical condition or disease, which is separate from treating.

Routes and frequency of administration of the therapeutic compositions described herein, as well as dosage, will vary from individual to individual, and from disease to disease, and may be readily established using standard techniques. Preferably, the compositions may be administered by intratumor injection.

Compositions suitable for intratumor injectable use include sterile aqueous solutions (where water soluble) and sterile powders for the extemporaneous preparation of sterile injectable solutions. The carrier can be a solvent or dispersion medium containing, for example, water, ethanol, polyol (for example, glycerol, propylene glycol and liquid polyethylene glycol, and the like), suitable mixtures thereof and vegetable oils. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by, for example, filter sterilization or sterilization by other appropriate means. Dispersions may be prepared by incorporating the various sterilized active ingredients into a sterile vehicle which contains the basic dispersion medium and the required other ingredients from those enumerated above. In the case of sterile powders for the preparation of sterile injectable solutions, a preferred method of preparation includes vacuum drying and the freeze-drying technique which yield a powder of the active ingredient plus any additional desired ingredient from a previously sterile-filtered solution.

In conjunction with any of the foregoing methods, the compositions can be administered in combination with another drug. In each case, the composition can be administered prior to, at the same time as, or after the administration of the other drug. In accordance with the methods described herein, more than one compound or composition may be co-administered with one or more other compounds, such as known chemotherapies and an anti-inflammatory drugs (such as betamethasone, non-steroid anti-inflammatory drugs (NSAIDs), acetaminophen, ibuprofen, naproxen), and/or other suitable drugs. The provided methods may be further combined with other tumor therapies such as radiotherapy, surgery, hormone therapy and/or immunotherapy. Thus, the provided methods can further include administering one or more additional therapeutic agents to the subject. Suitable additional therapeutic agents include, but are not limited to, analgesics, anesthetics, analeptics, corticosteroids, anticholinergic agents, anticholinesterases, anticonvulsants, antineoplastic agents, allosteric inhibitors, anabolic steroids, antirheumatic agents, psychotherapeutic agents, neural blocking agents, anti-inflammatory agents, antihelmintics, antibiotics, anticoagulants, antifungals, antihistamines, antimuscarinic agents, antimycobacterial agents, antiprotozoal agents, antiviral agents, dopaminergics, hematological agents, immunological agents, muscarinics, protease inhibitors, vitamins, growth factors, and hormones. The choice of agent and dosage can be determined readily by one of skill in the art based on the given disease being treated. Optionally, the additional therapeutic agent is octreotide acetate, interferon, pembrolizumab, glucopyranosyl lipid A, carboplatin, etoposide, or any combination thereof.

"Co-administered" conveys simultaneous administration in the same formulation or in two different formulations via the same or different routes or sequential administration by the same or different routes. "Sequential" administration conveys a time difference of seconds, minutes, hours, or days between the administration of the two or more separate compounds In some embodiments, it may be beneficial to include one or more excipients in a composition. One of skill in the art would appreciate that the choice of any one excipient may influence the choice of any other excipient. For example, the choice of a particular excipient may preclude the use of one or more additional excipients because the combination of excipients would produce undesirable effects. One of skill in the art would be able to determine empirically which excipients, if any, to include in the formulations or compositions disclosed herein. Excipients may include, but are not limited to, co-solvents, solubilizing agents, buffers, pH adjusting agents, bulking agents, surfactants, encapsulating agents, tonicity-adjusting agents, stabilizing agents, protectants, and viscosity modifiers. In some embodiments, it may be beneficial to include a pharmaceutically acceptable carrier.

In some embodiments, it may be beneficial to include a solubilizing agent. Solubilizing agents may be useful for increasing the solubility of any of the components of the formulation or composition, including a peptide disclosed herein or an excipient. The solubilizing agents described herein are not intended to constitute an exhaustive list, but are provided merely as exemplary solubilizing agents that may be used. In certain embodiments, solubilizing agents include, but are not limited to, ethyl alcohol, tert-butyl alcohol, polyethylene glycol, glycerol, methylparaben, propylparaben, polyethylene glycol, polyvinyl pyrrolidone, and any pharmaceutically acceptable salts and/or combinations thereof.

The pH may be any pH that provides desirable properties for the composition. Desirable properties may include, for example, peptide stability, increased peptide retention as compared to compositions at other pHs, and improved filtration efficiency.

In some embodiments, it may be beneficial to include a tonicity-adjusting agent. The tonicity of a liquid composition is an important consideration when administering the composition to a patient, for example, by parenteral administration. Tonicity-adjusting agents, thus, may be used to help make a composition suitable for administration. Tonicity-adjusting agents are well known in the art. Accordingly, the tonicity-adjusting agents described herein are not intended to constitute an exhaustive list but are provided merely as exemplary tonicity-adjusting agents that may be used. Tonicity-adjusting agents may be ionic or non-ionic and include, but are not limited to, inorganic salts, amino acids, carbohydrates, sugars, sugar alcohols, and carbohydrates. Exemplary inorganic salts may include sodium chloride, potassium chloride, sodium sulfate, and potassium sulfate. An exemplary amino acid is glycine. Exemplary sugars may include sugar alcohols such as glycerol, propylene glycol, glucose, sucrose, lactose, and mannitol.

In some embodiments, it may be beneficial to include a stabilizing agent. Stabilizing agents help increase the stability of peptides in compositions of the invention.

In some embodiments, it may be beneficial to include a protectant. Protectants are agents that protect a pharmaceutically active ingredient (e.g., a peptide as disclosed herein) from an undesirable condition (e.g., instability caused by freezing or lyophilization, or oxidation). Protectants can include, for example, cryoprotectants, lyoprotectants, and antioxidants. Cryoprotectants are useful in preventing loss of potency of an active pharmaceutical ingredient (e.g., a peptide as disclosed herein) when a formulation is exposed to a temperature below its freezing point. For example, a cryoprotectant could be included in a reconstituted lyophilized formulation so that the formulation could be frozen before dilution for intravenous (IV) administration. Cryoprotectants are well known in the art. Accordingly, the cryoprotectants described herein are not intended to constitute an exhaustive list, but are provided merely as exemplary cryoprotectants that may be used. Cryoprotectants include, but are not limited to, solvents, surfactants, encapsulating agents, stabilizing agents, viscosity modifiers, and combinations thereof. Cryoprotectants may include, for example, disaccharides (e.g., sucrose, lactose, maltose, and trehalose), polyols (e.g., glycerol, mannitol, sorbitol, and dulcitol), glycols (e.g., ethylene glycol, polyethylene glycol, propylene glycol).

Lyoprotectants are useful in stabilizing the components of a lyophilized formulation or composition. For example, a peptide as disclosed herein could be lyophilized with a lyoprotectant prior to reconstitution. Lyoprotectants are well known in the art. Accordingly, the lyoprotectants described herein are not intended to constitute an exhaustive list, but are provided merely as exemplary lyoprotectants that may be used. Lyoprotectacts include, but are not limited to, solvents, surfactants, encapsulating agents, stabilizing agents, viscosity modifiers, and combinations thereof. Exemplary lyoprotectants may be, for example, sugars and polyols, trehalose, sucrose, dextran, and hydroxypropyl-beta-cyclodextrin are non-limiting examples of lyoprotectants.

Antioxidants are useful in preventing oxidation of the components of a composition. Oxidation may result in aggregation of a drug product or other detrimental effects to the purity of the drug product or its potency. Antioxidants are well known in the art. Accordingly, the antioxidants described herein are not intended to constitute an exhaustive list but are provided merely as exemplary antioxidants that may be used. Antioxidants may be, for example, sodium ascorbate, citrate, thiols, metabisulfite, and combinations thereof.

The invention also includes a kit comprising any of the compositions described herein, or any of the individual components of the compositions described herein. Reagents may be present in free form or immobilized to a substrate such as a plastic dish, microarray plate, a test tube, a test rod and so on. The kit can also include suitable reagents for the detection of the reagent and/or for the labeling of positive or negative controls, wash solutions, dilution buffers and the like. The kit can also include a set of written instructions for using the kit and interpreting the results. Kits may be prepared and used for any clinical, research or diagnostic method of the invention.

Variations, modifications, and other implementations of what is described herein will occur to those of ordinary skill without departing from the spirit and the scope of the present disclosure. Accordingly, the ensuing claims not to be limited only to the preceding illustrative description.

Each of the embodiments described herein may be combined individually or in combination with one or more other embodiments of the invention.

Those skilled in the art will recognize or be able to ascertain using no more than routine experimentation, numerous equivalents to the compounds, compositions, and methods of use thereof described herein. Such equivalents are considered to be within the scope of the compositions and methods disclosed herein.

The contents of all references, patents and published patent applications cited throughout this application, as well as their associated figures are hereby incorporated by reference in their entirety.

EXAMPLES

The following examples are put forth to provide those of ordinary skill in the art with a complete disclosure and description of how to make and use the embodiments and are not intended to limit the scope of what the inventors regard as their invention nor are they intended to represent that the experiments below are all or the only experiments performed.

Example 1

This example demonstrates that an anti-CTLA4 antibody improves the antitumor activity of yeast plus anti-OX40 therapy. Using a B 16F10 model system, female C57BL/6 mice were intradermally implanted with B16F10 with 130,000 B16F10 melanoma tumor cells on the left and right flanks. When the tumors were 5-7 mm in diameter the mice were treated via intratumoral injection 3 times into the tumors (every other day) with 100 micrograms each of $\alpha$OX40 (also referred to as anti-OX40) agonistic antibody (serves as an immune agonist and activates T cells) and $\alpha$CTLA4 (also referred as anti-CTLA4) antibody (serves as an immune checkpoint inhibitor and blocks immune suppressive responses) plus 5 YU of intact yeast expressing B 16F10 neoepitopes (PTK170-a TARMOGEN® that expresses neo epitopes and also serves as a TLR agonist). 100 µg of the TLR9 agonist CpG was used as a positive control treatment. Tumor growth of treated and untreated (distal) tumors was monitored for 28 days using digital calipers. (FIGS. 1A-1B) shows tumor volume to day 14 post-challenge (p.c.); (FIG. 1C) shows a Kaplan-Meier survival analysis to day 28 p.c. Statistics, one way ANOVA (tumor volume) or Log-rank (K-M); *, p<0.001; ** p<0.0001.

Example 2

Figure 2B:
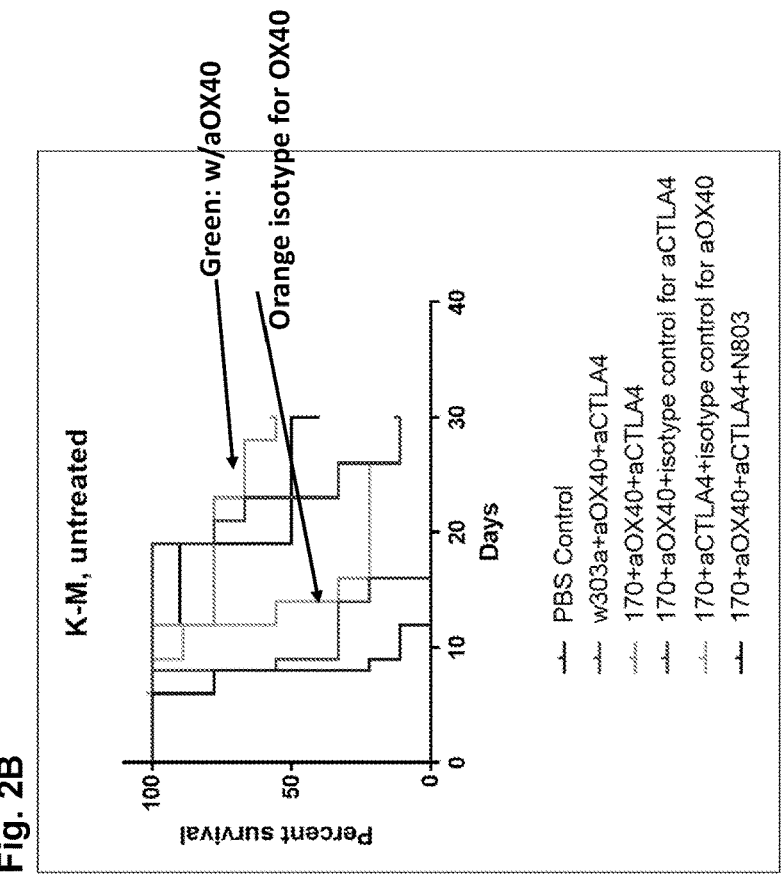
FIGS. 2A and 2B show isotype control antibodies are less effective than anti-CTLA4 and anti-OX40 in the bilateral tumor model. K-M survival curves are shown for treated (FIG. 2A) and untreated tumors (FIG. 2B). Statistics for FIG. 2A: Log-rank analysis of each group against PBS; *** p<0.001. "170" is intact yeast expressing the a B16F10 "polytope", but the polytope has only one real epitope (p11) and is not needed for the effect.
Figure 2A:
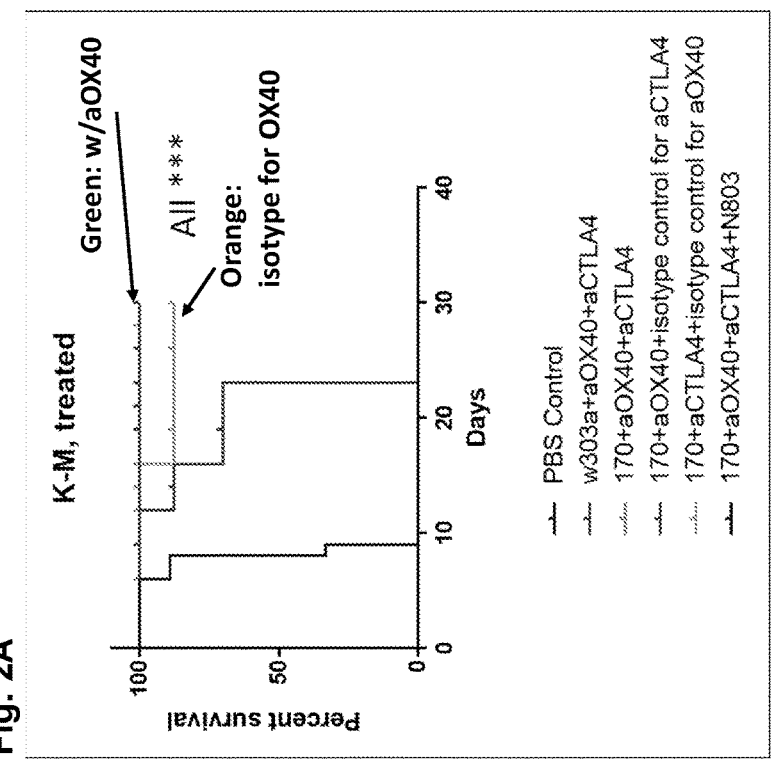

This example shows that isotype control antibodies are less effective than anti-CTLA4 and anti-OX40 in the bilateral tumor model. Female C57BL/6 mice were implanted with B16F10 as in Example 1 for FIGS. 1A-1BH. Tumor treatments were indicated and included 100 µg of isotype control antibodies for anti-OX40 antibody or anti-CTLA4 antibodies (rat anti mouse IgG1k, and syrian hamster IgG, respectively), and yeast were pressure homogenized ("pressure lysate, pL"). w303a, yeast null pL; 170, pTK170 pL; N803, human IL-15 superagonist, 1 K-M survival curves are shown for treated (FIG. 2A) and untreated tumors (FIG. 2B). Statistics for FIG. 2A: Log-rank analysis of each group against PBS; *** p<0.001.

Example 3

Figure 3A:
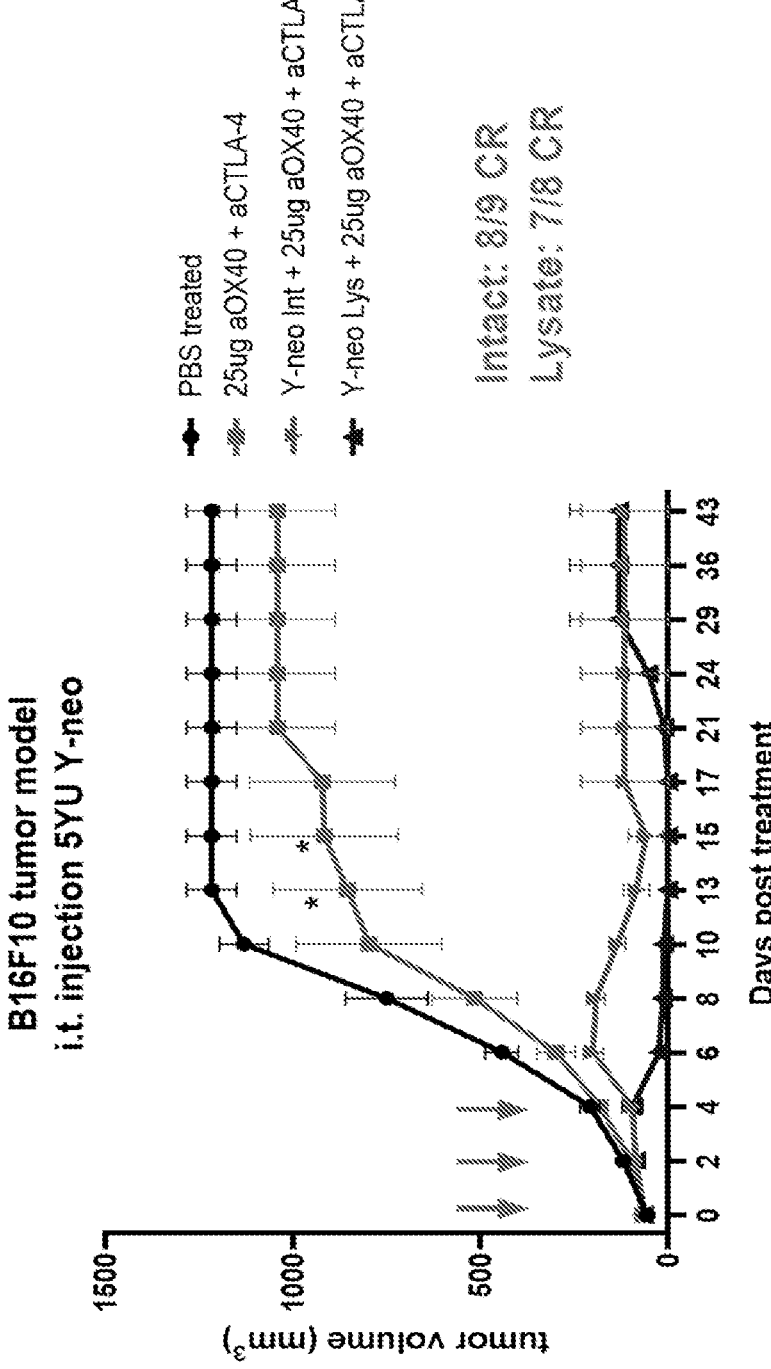
FIGS. 3A and 3B show intratumoral (IT) injection of intact or lysed neoepitope yeast plus αCTLA4/αOX40 eradicates B16F10 tumors and confers tumor protection upon tumor re-challenge.
Figure 3B:
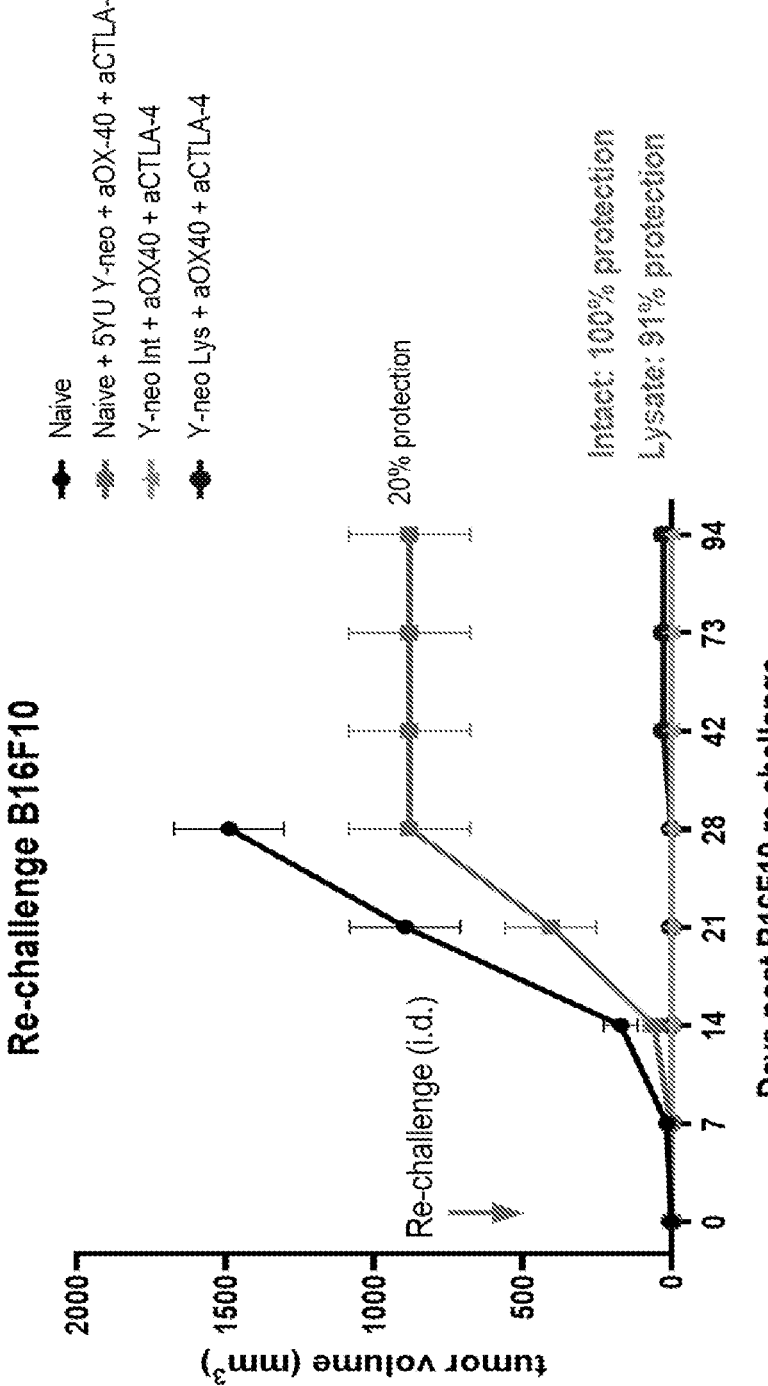

This example shows intratumoral injection of intact or lysed neoepitope yeast plus $\alpha$CTLA4/$\alpha$OX40 eradicates B16F10 tumors and confers tumor protection upon tumor re-challenge. Female C57BL/6 mice were implanted with B16F10 cells and treated with triple therapy as described in Example 1 for FIGS. 1A-1H except that antibody amounts were lowered to 25 µg each and were mixed with 5 YU of intact (Int) or pressure homogenized (Lys) yeast. FIG. 3A shows tumor growth rates of primary tumor, with complete response rates of 8/9 and 7/8 mice for intact and lysed yeast, respectively. FIG. 3B shows complete responders were re-challenged on day 43 with 130,000 B16F10 tumor cells and growth was monitored for 94 additional days. An additional exploratory group of 5 naive mice was subcutaneously vaccinated with 2.5 YU of intact and 2.5 YU of pressure homogenized pTK170 yeast, with 25 µg of each antibody concurrently delivered intraperitoneally (gray). Statistics by 2 way ANOVA with Dunett's multiple comparison for: FIG. 3A, p<0.0001, intact and lysate groups compared to PBS from day 8 onward; FIG. 3B, intact and lysate group compared to Naive from day 21 onward.

Example 4

Figure 4A:
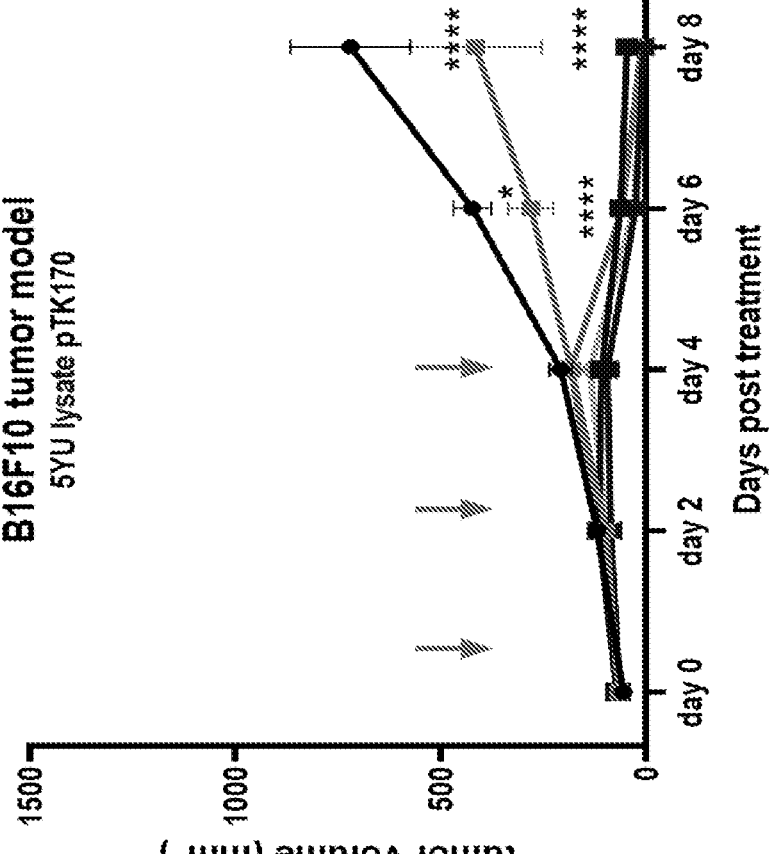
FIGS. 4A and 4B show the effect of αOX40 and αCTLA4 antibody dose on antitumor activity in the B16F10 triple therapy model. Growth rates of primary tumor through (FIG. 4A) day 8 and (FIG. 4B) day 17 post treatment are shown. Statistics by two way ANOVA with Dunett's multiple comparison compared to PBS; significance applies to all lysate cohorts. *, p<0.001; **, p<0.0001.
Figure 4B:
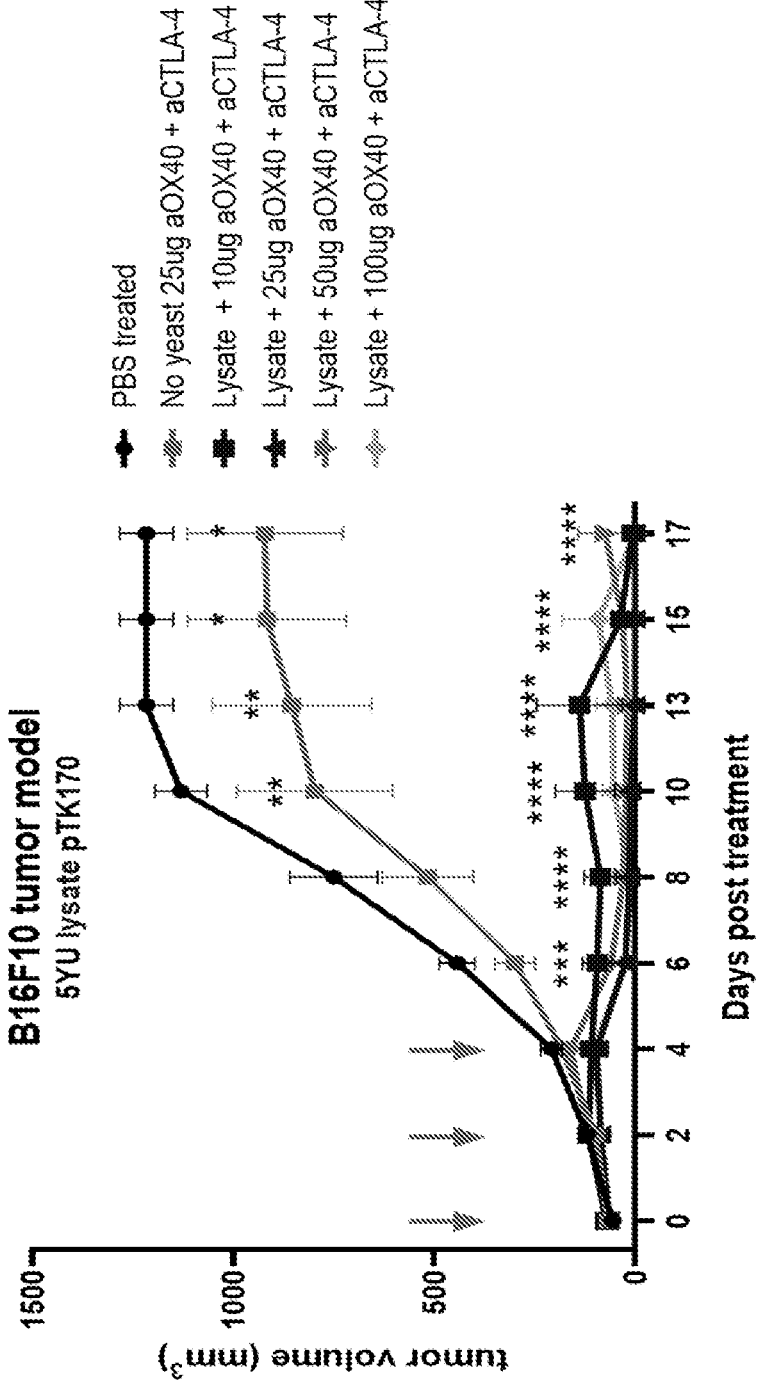

This example shows the effect of $\alpha$OX40 and $\alpha$CTLA4 antibody dose on antitumor activity in the B16F10 triple therapy model. Female C57BL/6 mice were implanted with B16F10 cells and treated with triple therapy as described in Example 1 for FIG. 1A-1H except that varying $\alpha$OX40 and $\alpha$CTLA4 antibody amounts were tested from 10 to 100 µg each as indicated. Antibodies were mixed with 5 YU of pressure homogenized yeast (Lysate). Growth rates of primary tumor through (FIG. 4A) day 8 and (FIG. 4B) day 17 post treatment are shown. Statistics by two way ANOVA with Dunett's multiple comparison compared to PBS; significance applies to all lysate cohorts. *, p<0.001; **, p<0.0001.

Example 5

Figures 5A, 5B:
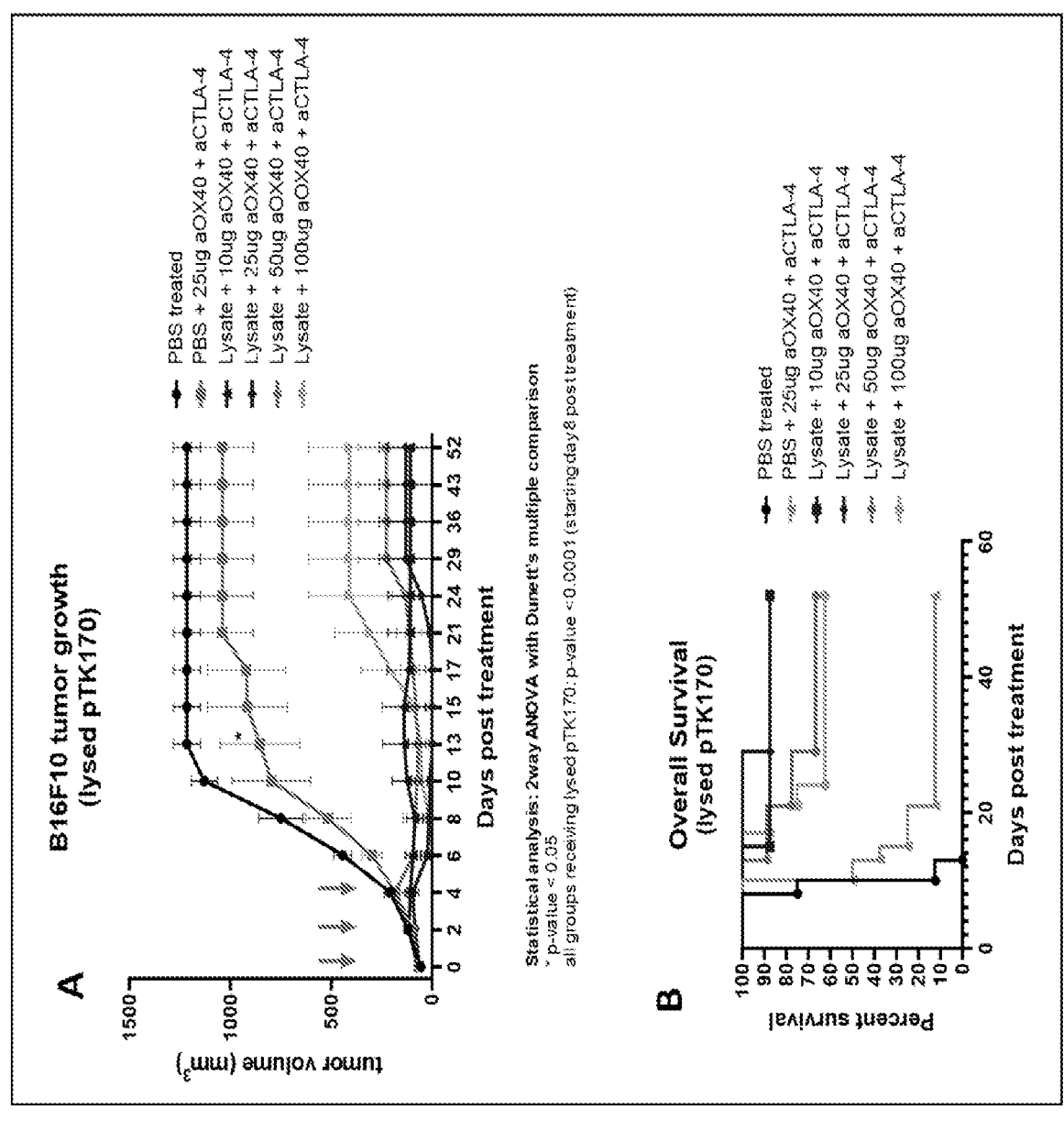
FIGS. 5A and 5B show the effect of αOX40 and αCTLA4 antibody dose on antitumor activity in the B16F10 triple therapy model.

This example shows the effect of $\alpha$OX40 and $\alpha$CTLA4 antibody dose on antitumor activity in the B16F10 triple therapy model. Female C57BL/6 mice were implanted with B16F10 cells and treated with triple therapy as described in Example 1 for FIGS. 1A-1H except that varying $\alpha$OX40 and αCTLA4 antibody amounts were tested from 10 μg to 100 μg as indicated. Antibodies were mixed with 5 YU of pressure homogenized yeast (Lysate). FIG. 5A shows tumor growth rate (volume) through day 52 post treatment; FIG. 5B shows Kaplan-Meier survival plot for the same time period. As can be seen a very low dose of anti-O40 was needed to get long term protection. There is no need to have a systemic dose of anti-Ox40 to get activity.

Example 6

Figure 6A:
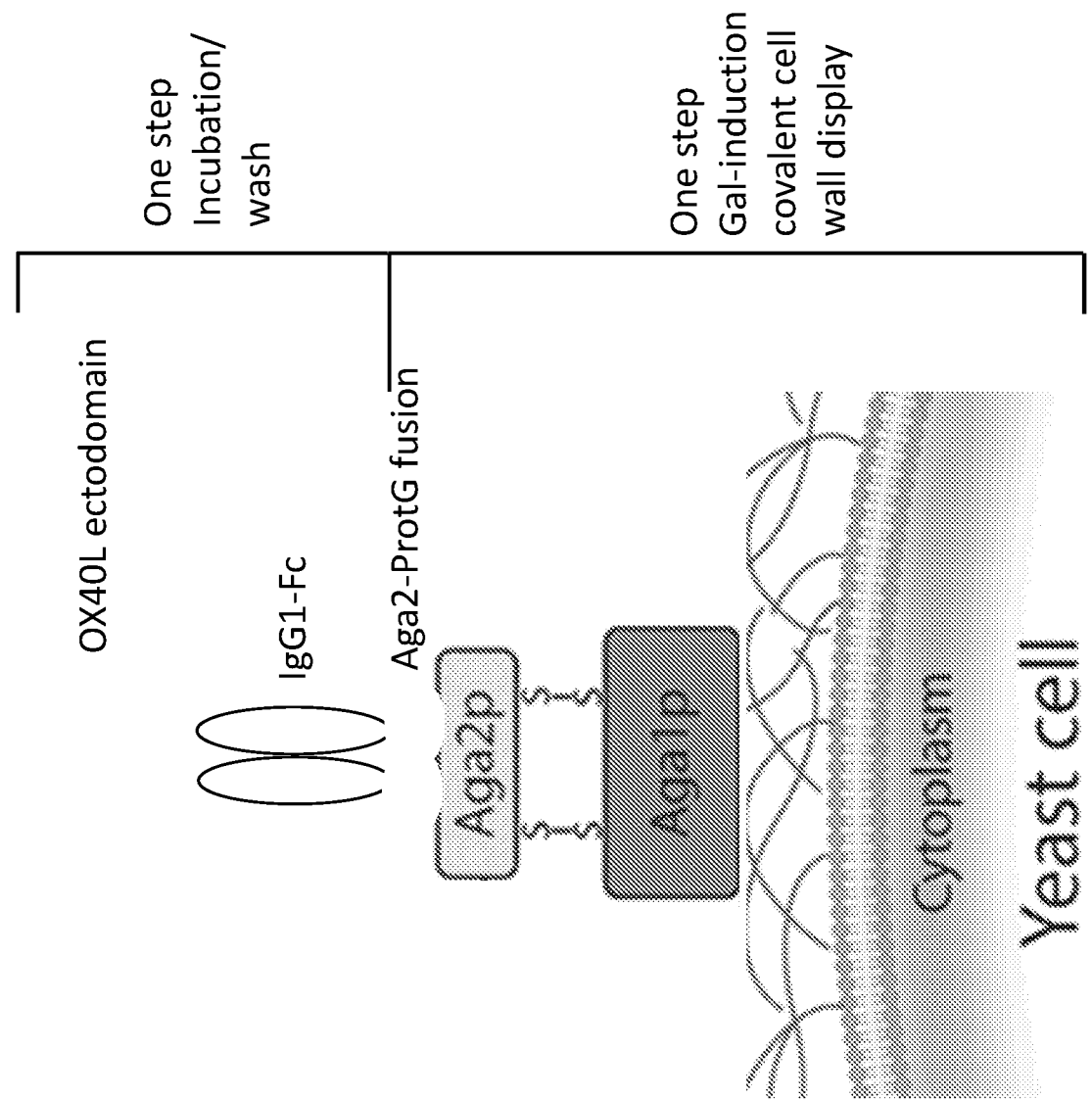
Figure 6B:
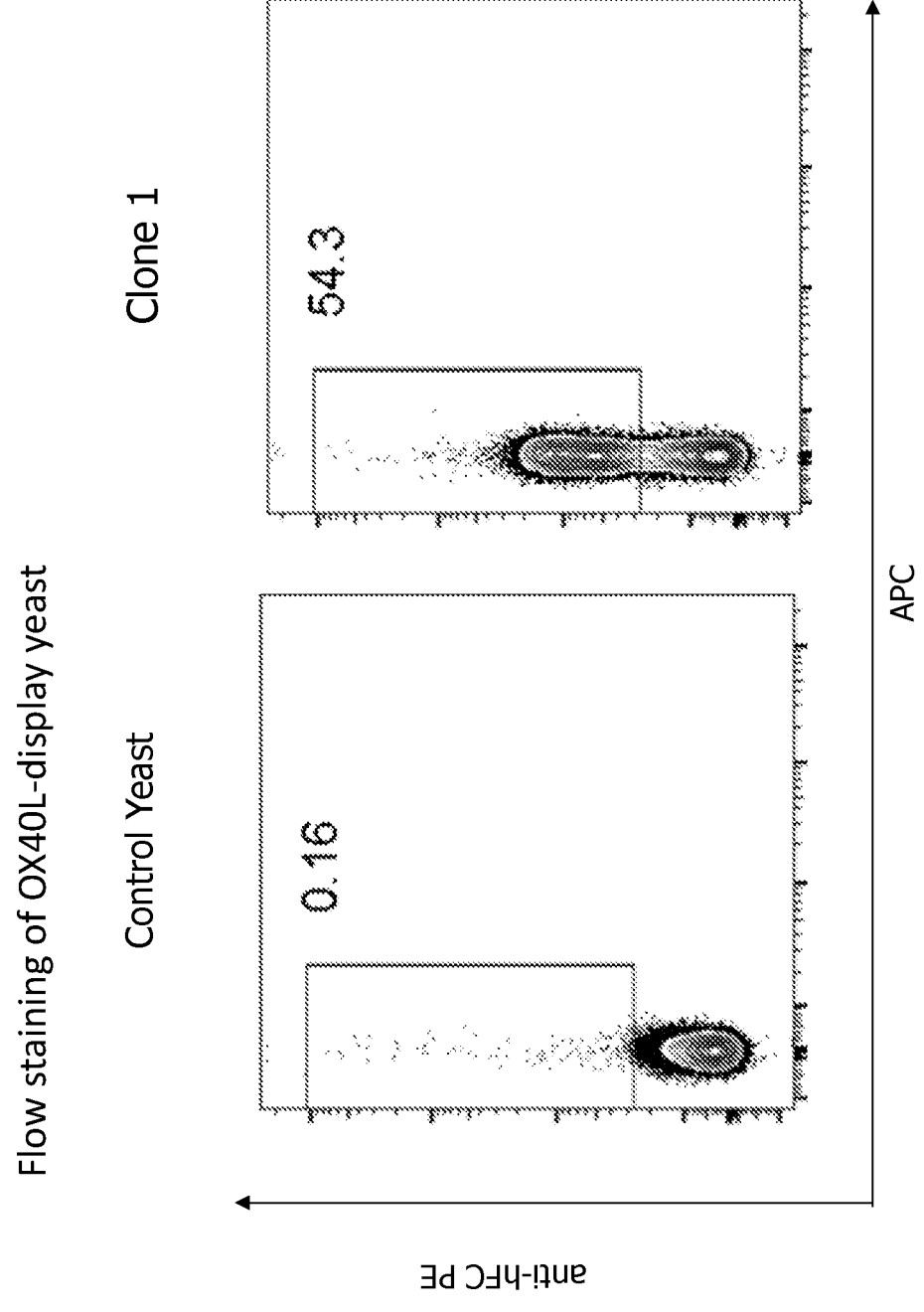
Figure 6E:
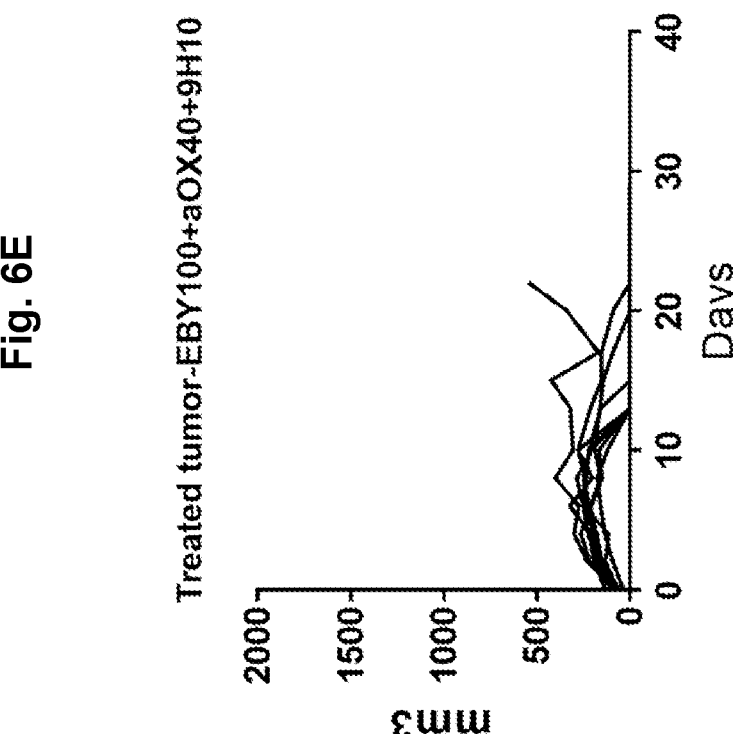
Figure 6D:
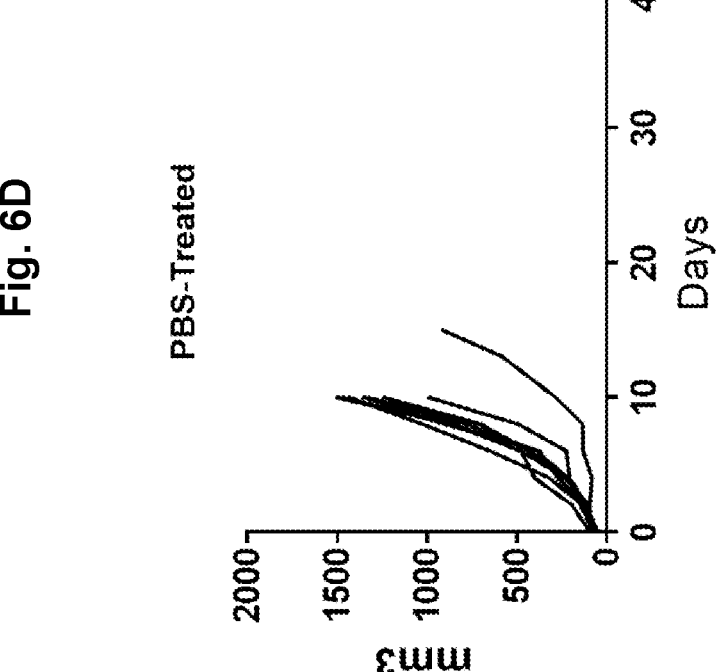
Figure 6G:
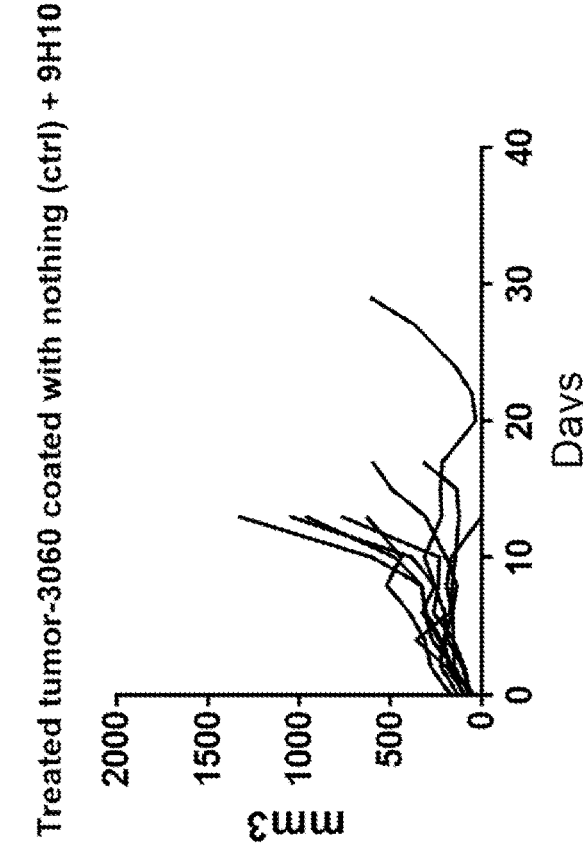
Figure 6F:
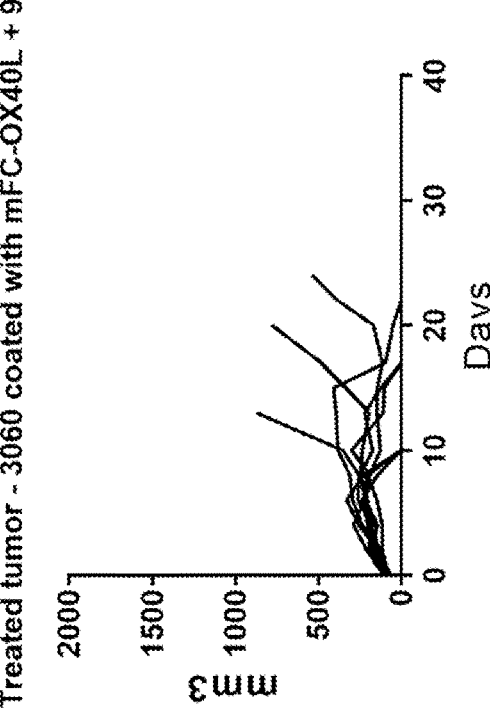
Figures 6H, 6I:
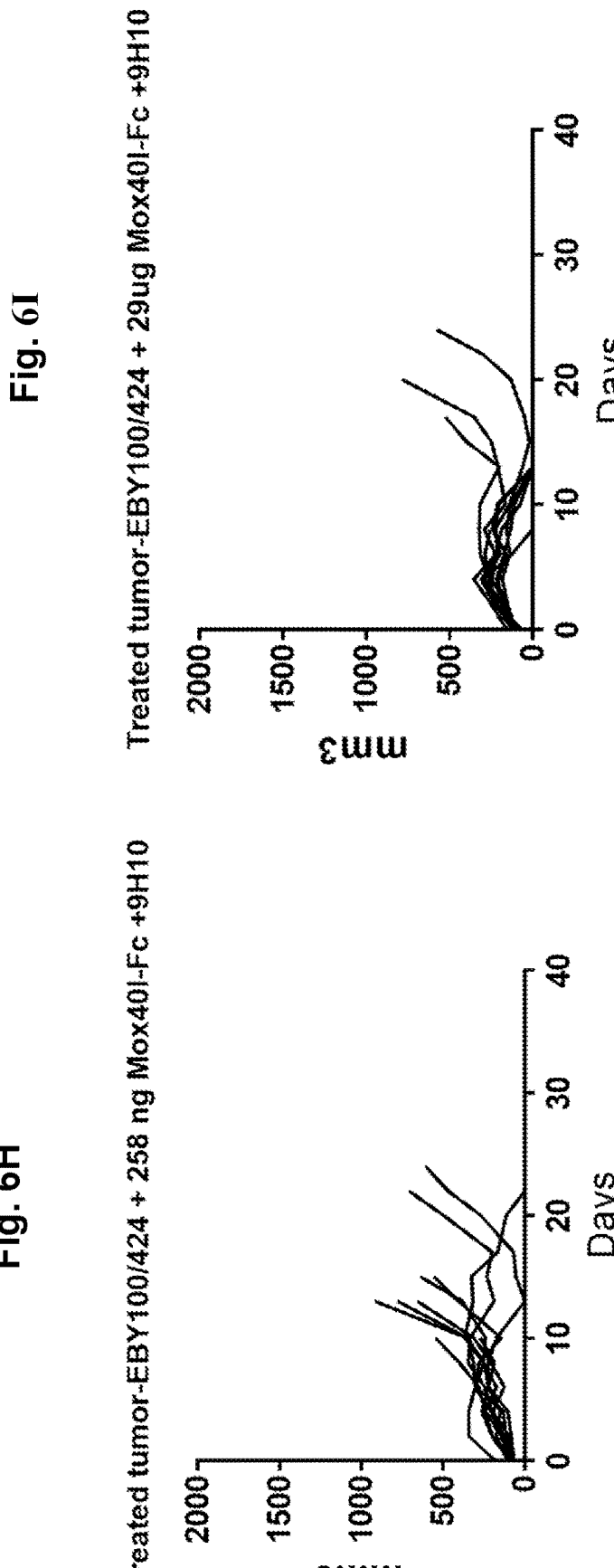
Figure 6L:
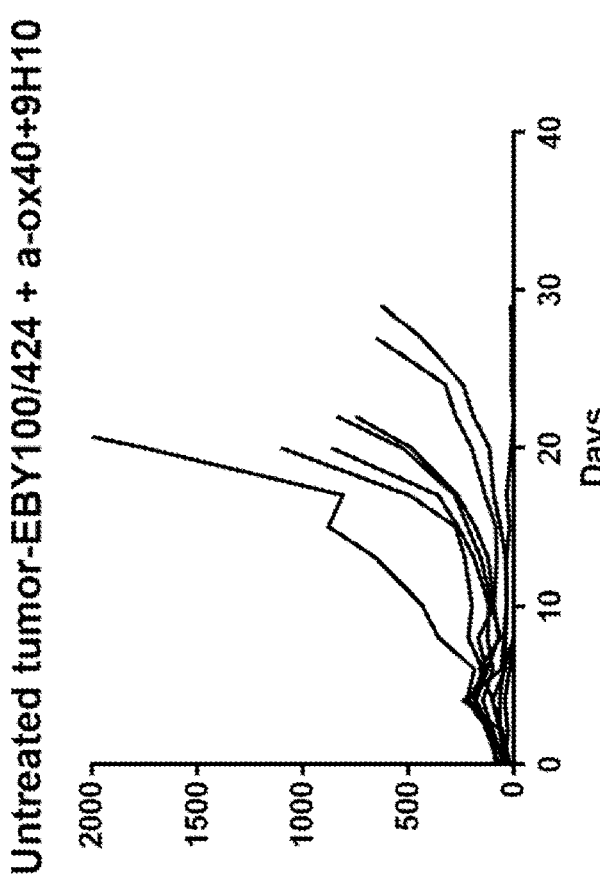
Figure 6K:
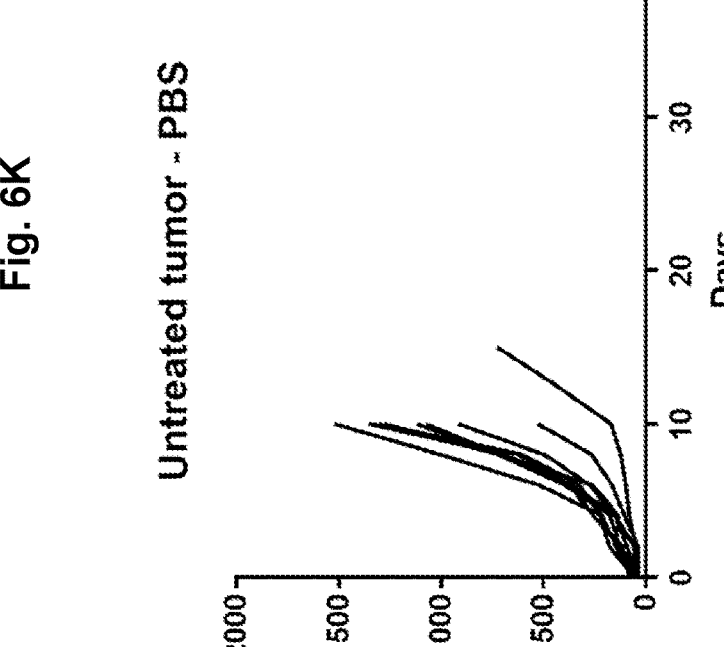
Figures 6M, 6N:
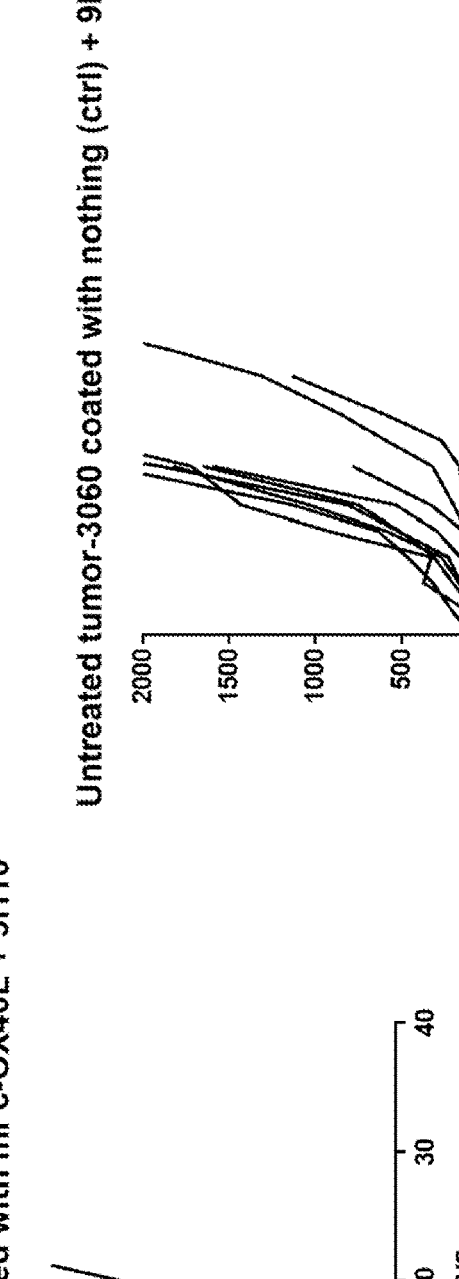

This example shows intratumoral injection of yeast displaying Fc-OX40L. FIGS. 6A-6B: yeast were engineered to express surface displayed protein G, which binds any Fc-containing protein, in this case Fc-OX40L. FIG. 6A is the schematic of the strain; FIG. 6B is the flow cytometric analysis showing that ~54% of yeast cells have detectable Fc-OX40L following coating and washing of protein G-expressing yeast. FIG. 6C, shows the intratumoral injection regimen and treatment groups; assay was performed as in Example 1 for FIGS. 1A-1H except that specific concentrations of treatment components varied as shown. Effects of the treatment on tumor growth and survival for treated (FIGS. 6D-6J) and untreated (FIGS. 6K-6Q) tumors are shown. For both FIGS. 6D-6I and 6K-6P the spider plots show tumor growth for individual mice and Kaplan-Meier curves (FIGS. 6J and 6Q) show survival. Statistics by log-rank, **p<0.01 for indicated comparisons. EBY100, parental yeast strain; 424, empty yeast expression plasmid; Mox40L-Fc, murine OX40L fused to IgG1 Fc.

Example 7

This example shows N803 can replace αOX40 in the B16F10 intratumoral injection assay. Female C57BL/6 mice were intradermally implanted with 130,000 B16F10 tumor cells in the right flank. When the tumors were 7-8 mm in diameter the mice were treated 3 times (every other day) with αOX40 agonistic antibody or N803, αCTLA4 antibody, and yeast null lysate in the amounts shown. Tumor growth of injected (primary) tumors was monitored for 38 days (FIG. 7A) or 68 days (FIG. 7B).

Example 8

Figure 8A:
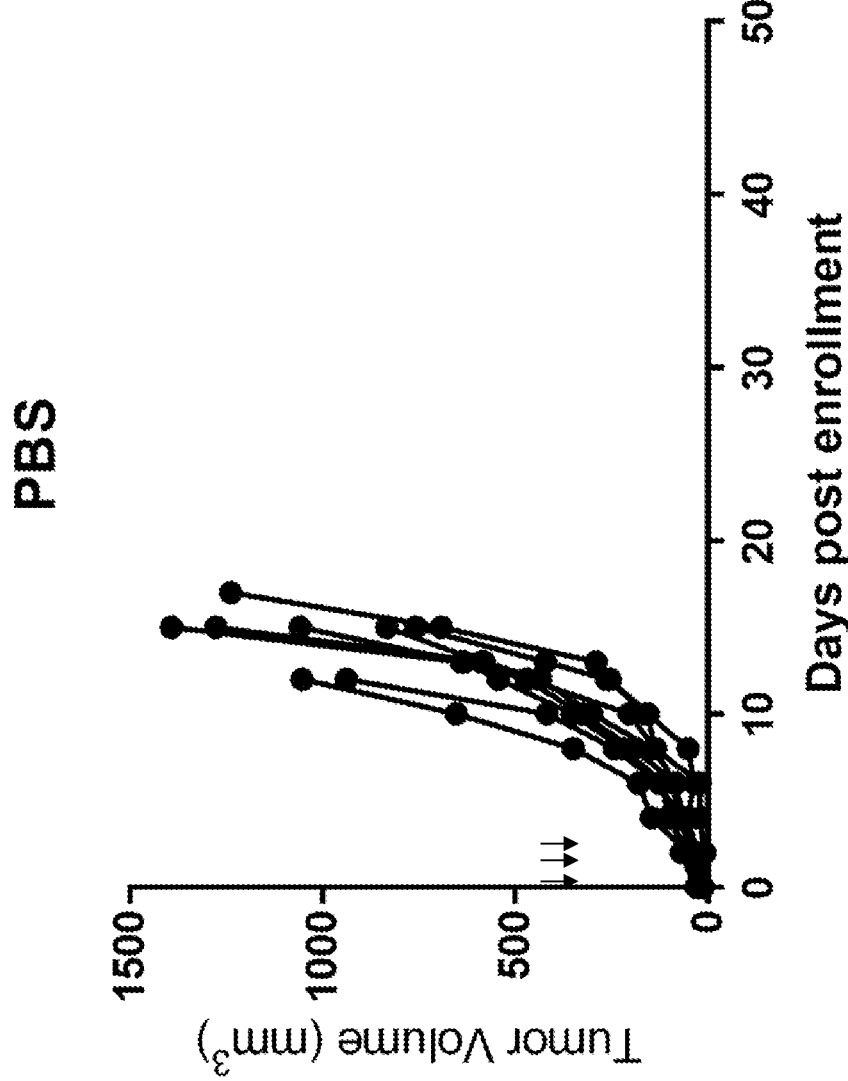
FIGS. 8A, 8B, 8C, 8D, 8E, 8F, 8G, 8H, 8I, 8J, and 8K shows MC38 tumor growth reduction following αPDL1/αOX40/yeast i.t. therapy.
Figures 8B, 8C:
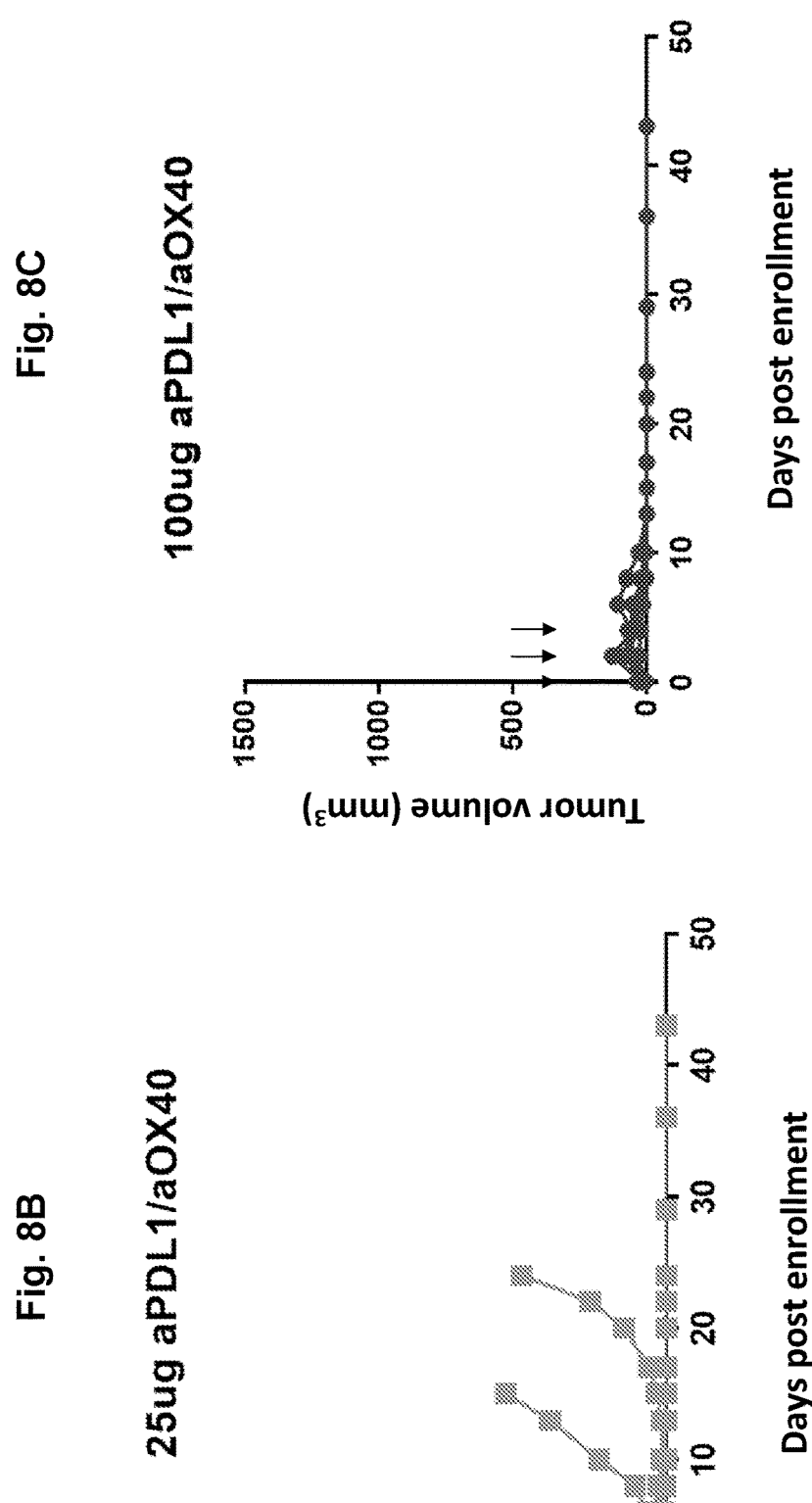
Figure 8E:
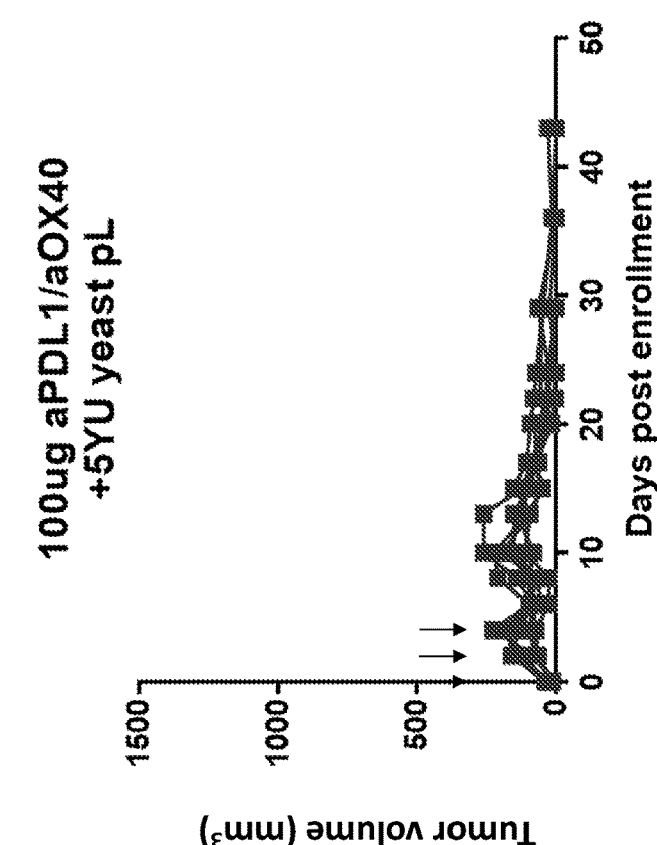
Figure 8D:
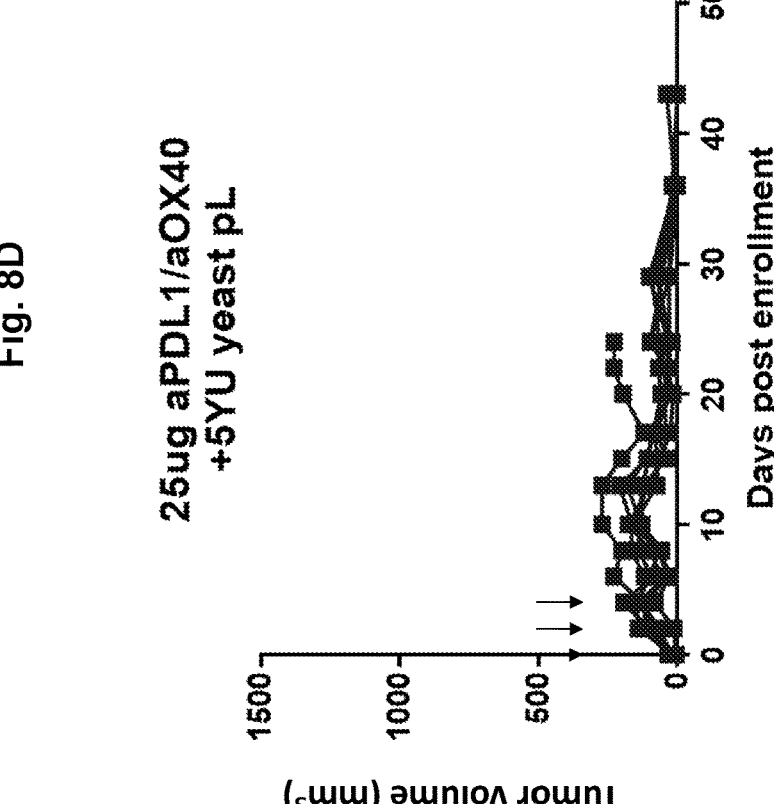
Figure 8F:
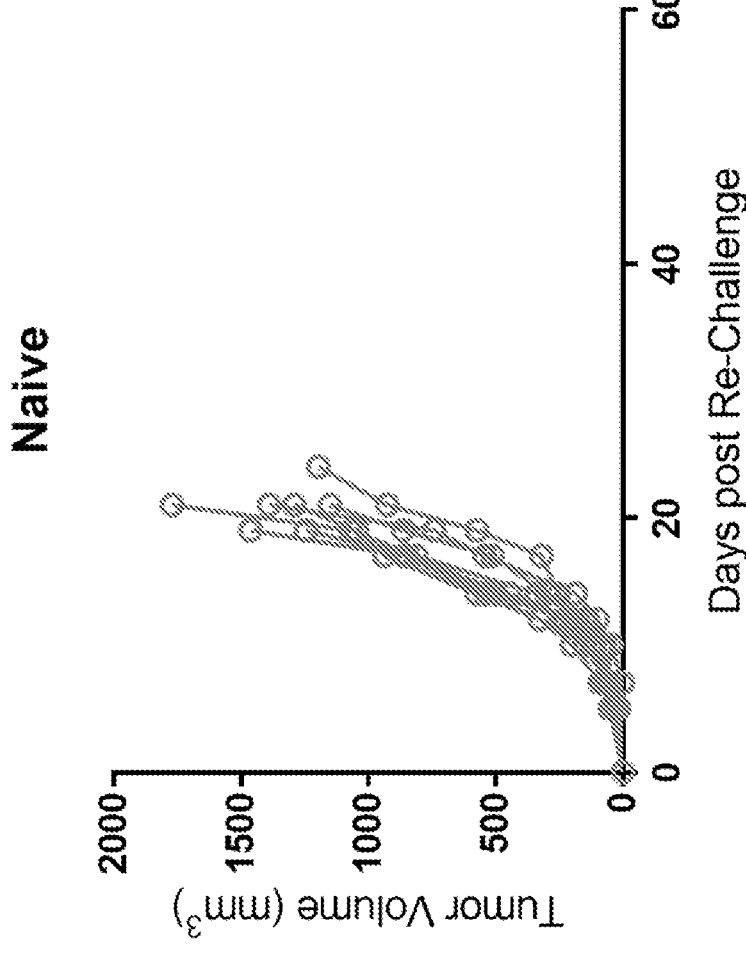
Figure 8H:
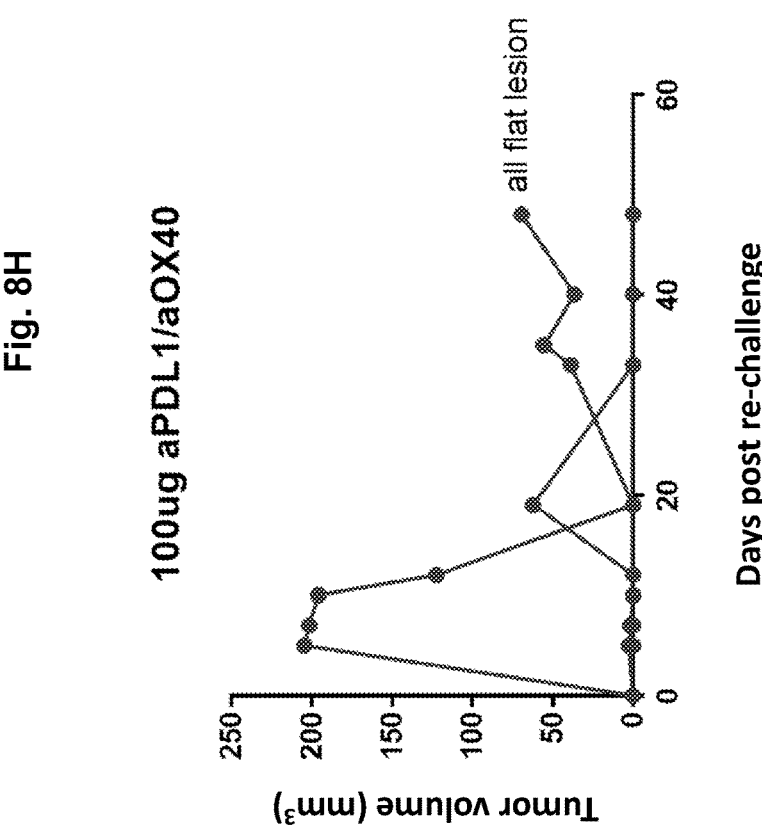
Figure 8G:
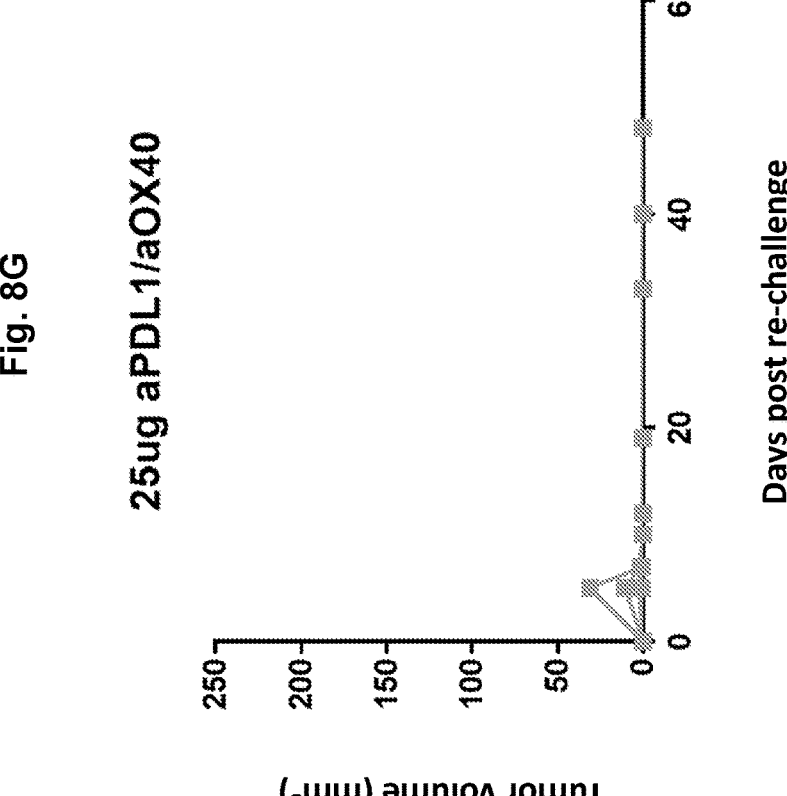
Figure 8J:
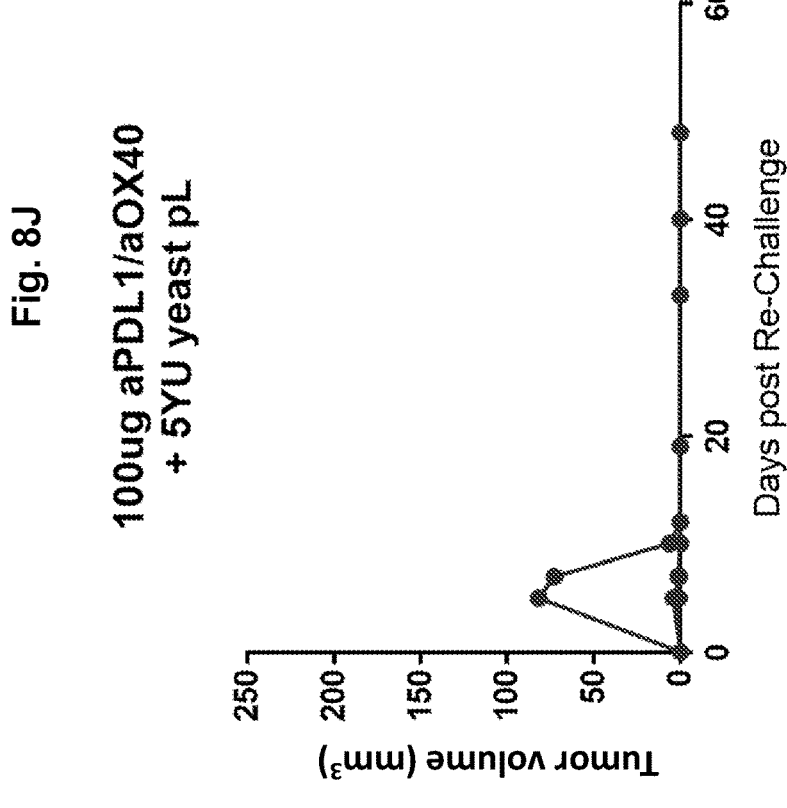
Figure 8I:
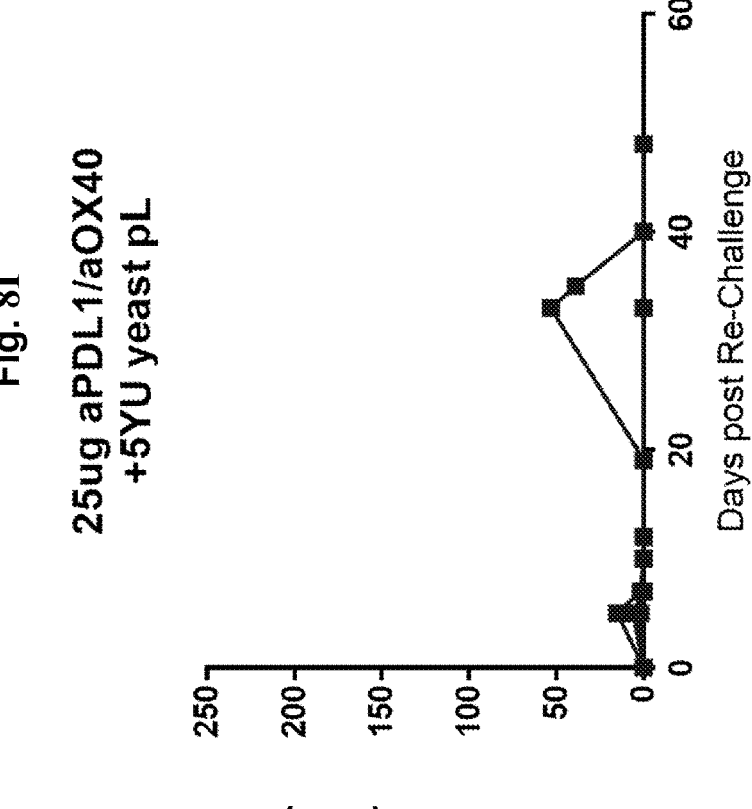
Figure 8K:
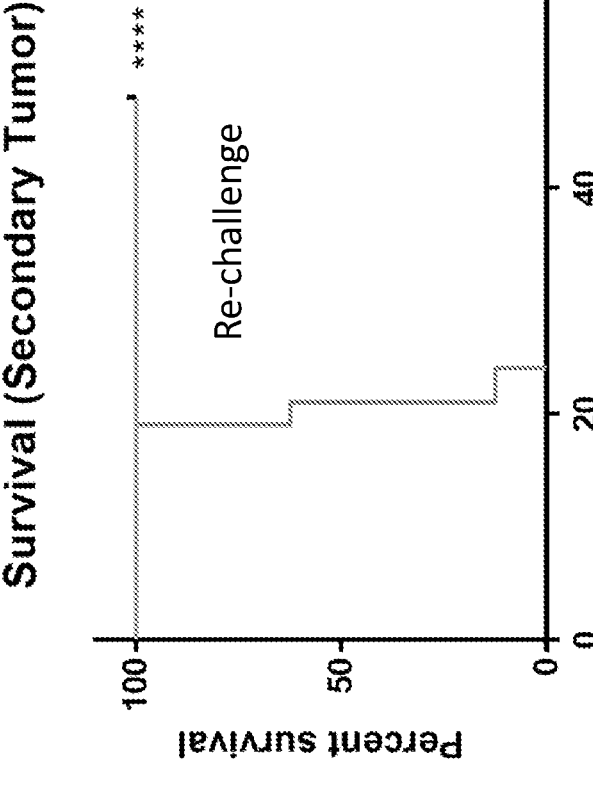

This example shows MC38 tumor growth reduction following αPDL1/αOX40/yeast intratumoral injection (i.t.) therapy. Female C57BL/6 mice were intradermally implanted with 300,000 MC38 tumor cells on the right flank. When the tumors were ~3-4 mm in diameter the mice were treated 3 times (every other day) with 25 μg αOX40 agonistic antibody and 25 or 100 μg of αPD-L1 antibody plus or minus 5 YU of yeast null lysate. (FIGS. 8A-8E) Primary tumor growth was monitored for 42 days. On day 45, complete responders were re-challenged intradermally on the contralateral (left) flank with 300,000 MC38 tumor cells and tumor volume (FIGS. 8f-8J) and survival (FIG. 8K) were monitored for 48 additional days. W303a pL, pressure homogenized yeast null lysate.

Example 9

Figure 9B:
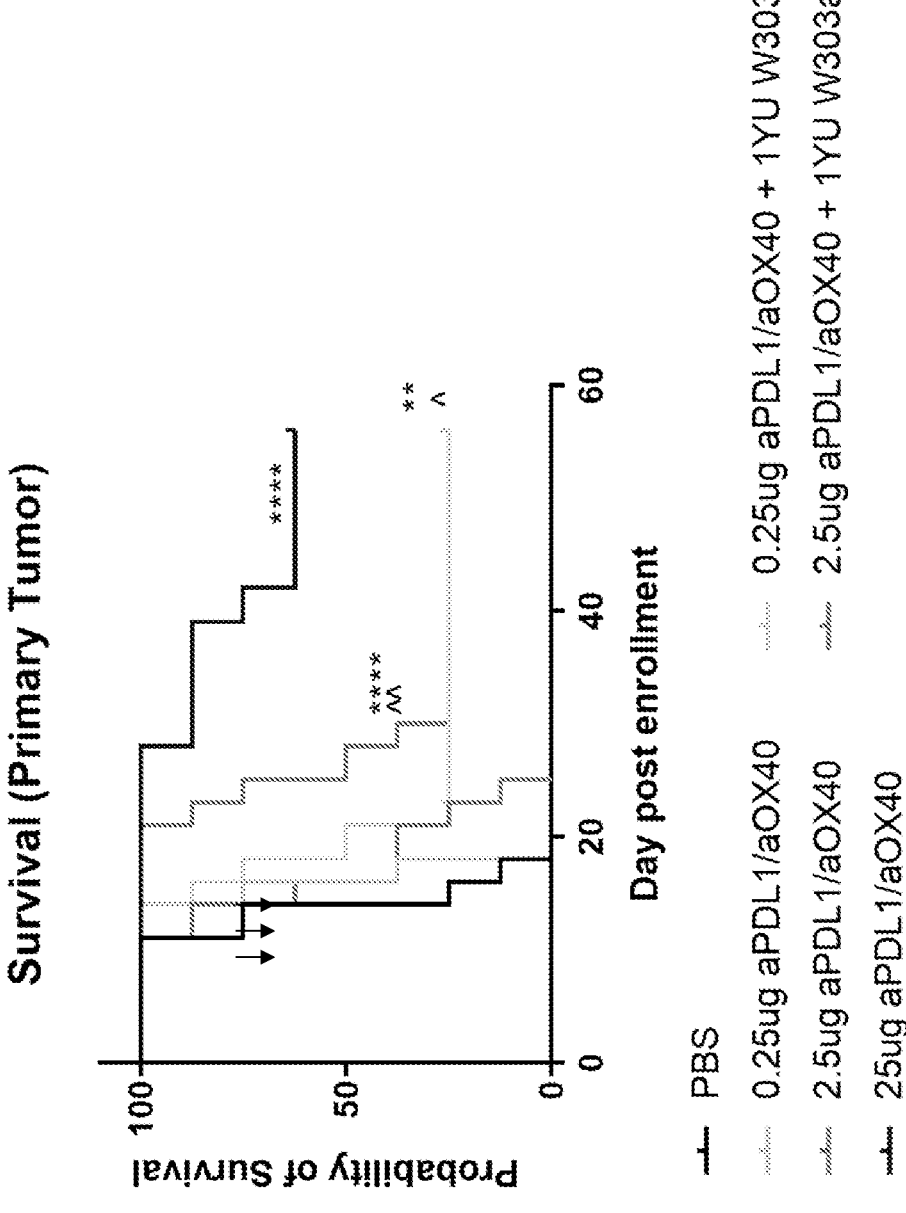

This example shows titration of anti-PDL1/anti-OX40 antibodies for intratumoral therapy of MC38 tumors. Female C57BL/6 mice were intradermally implanted with 300,000 MC38 tumor cells on the right flank. When the tumors were ~3-7 mm in diameter the mice were treated 3 times (every other day) with αOX40 agonistic antibody and αPD-L1 antibody (0.25 to 25 μg range) plus 1 YU of yeast null lysate (FIG. 9A). Survival was monitored for 48 days, showing a significant contribution of yeast lysate to the treatment effect (FIG. 9B). W303a, yeast null; pL=pressure lysate. Statistics: Mantel-Cox test * compared to PBS; A comparison to group with same dose of antibodies but lacking yeast pL.

Example 10

Figure 10B:
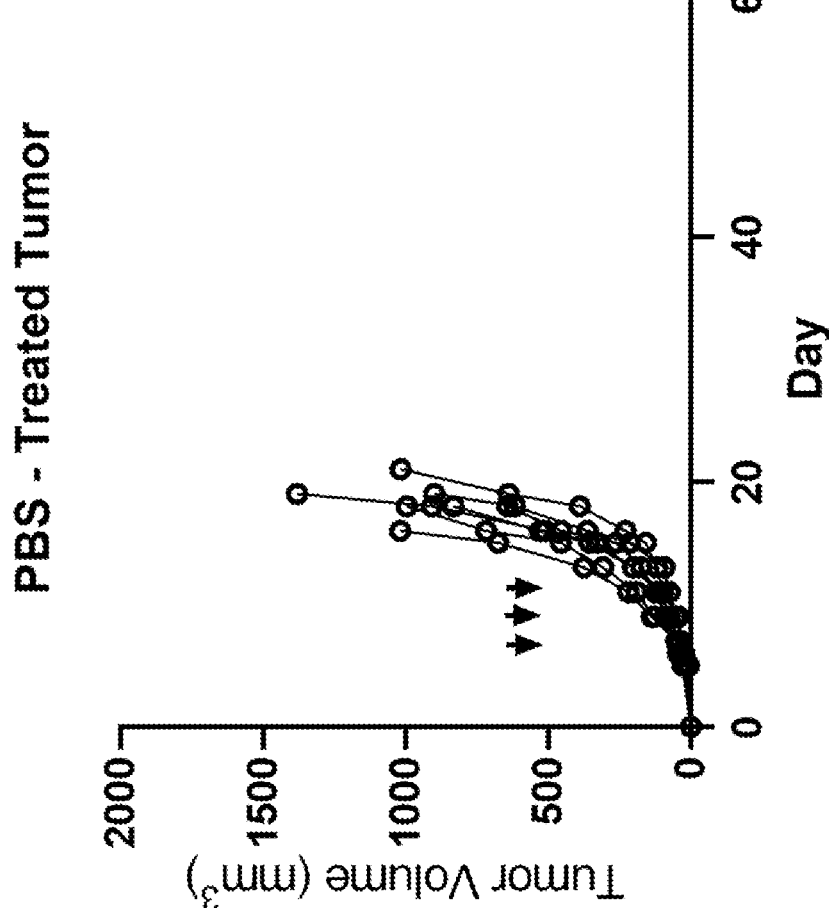
Figure 10D:
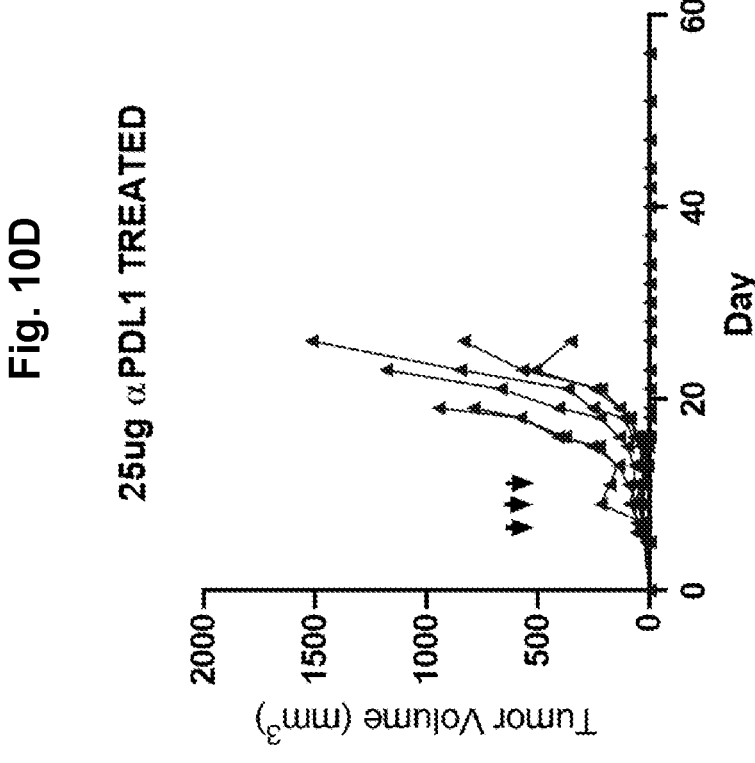
Figure 10C:
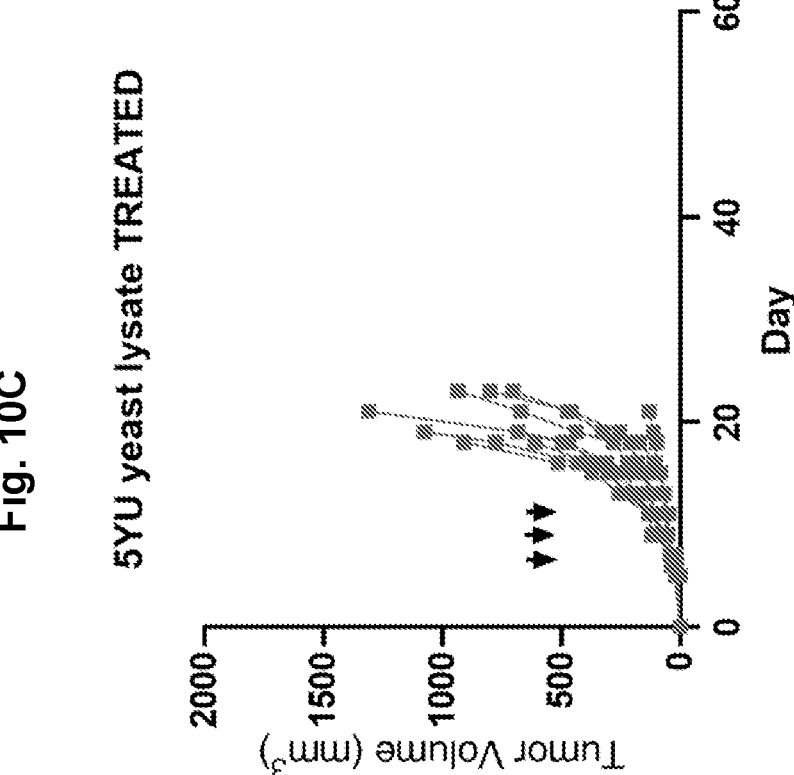
Figure 10G:
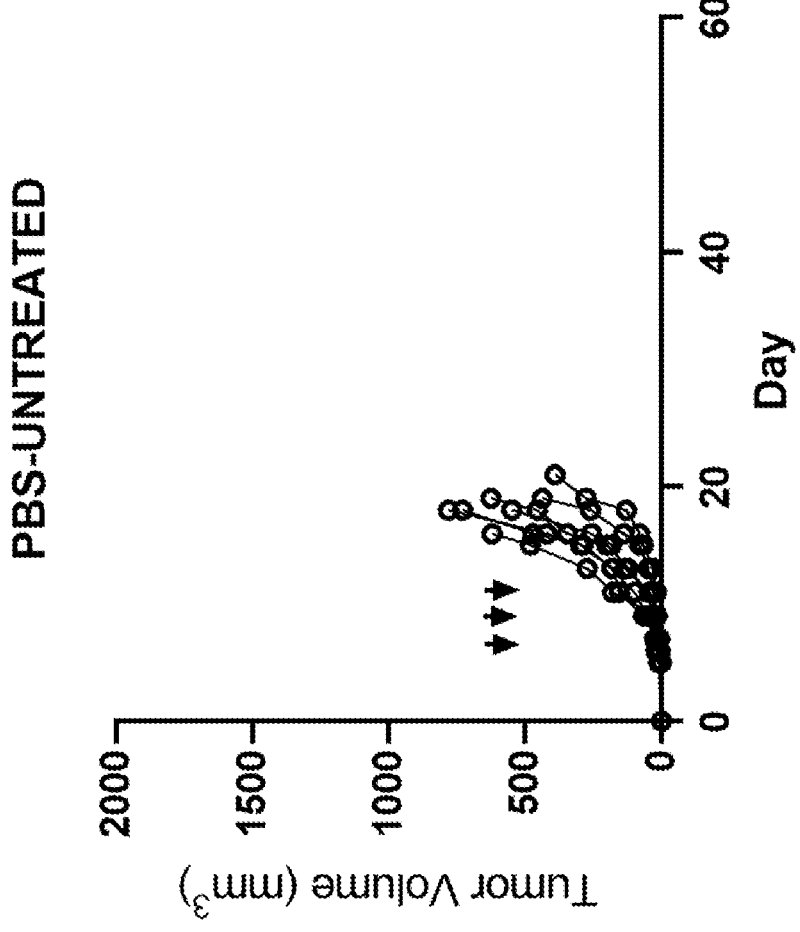
Figure 10I:
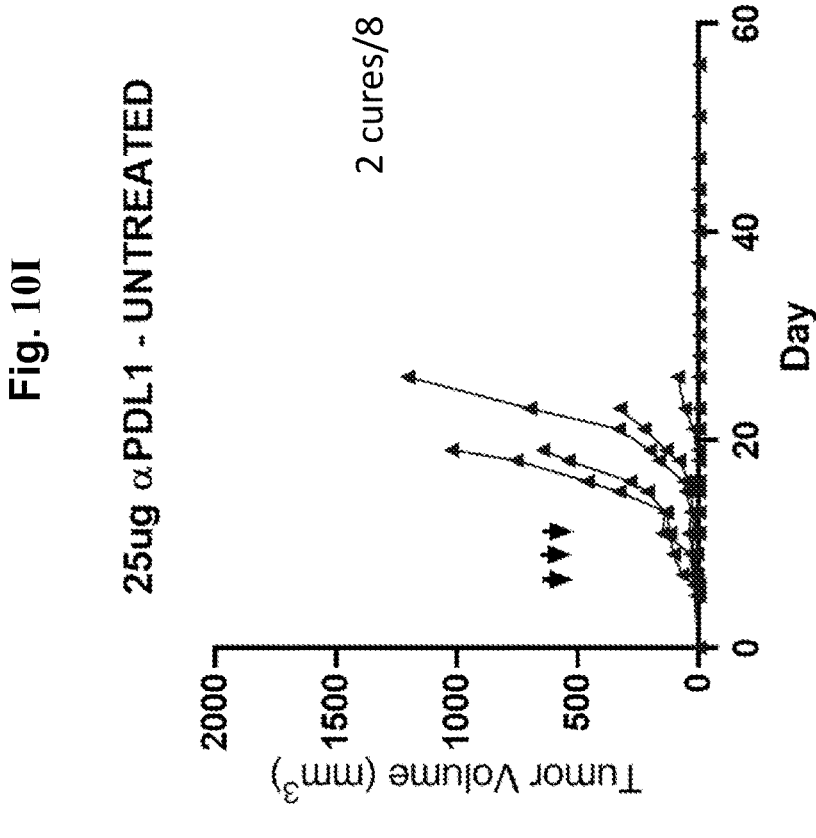
Figure 10H:
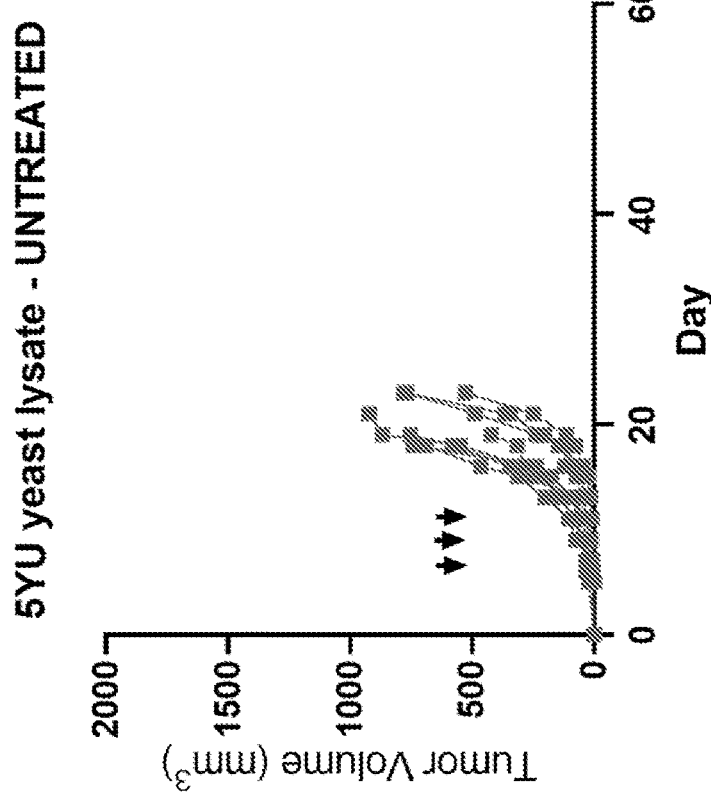
Figures 10J, 10K:
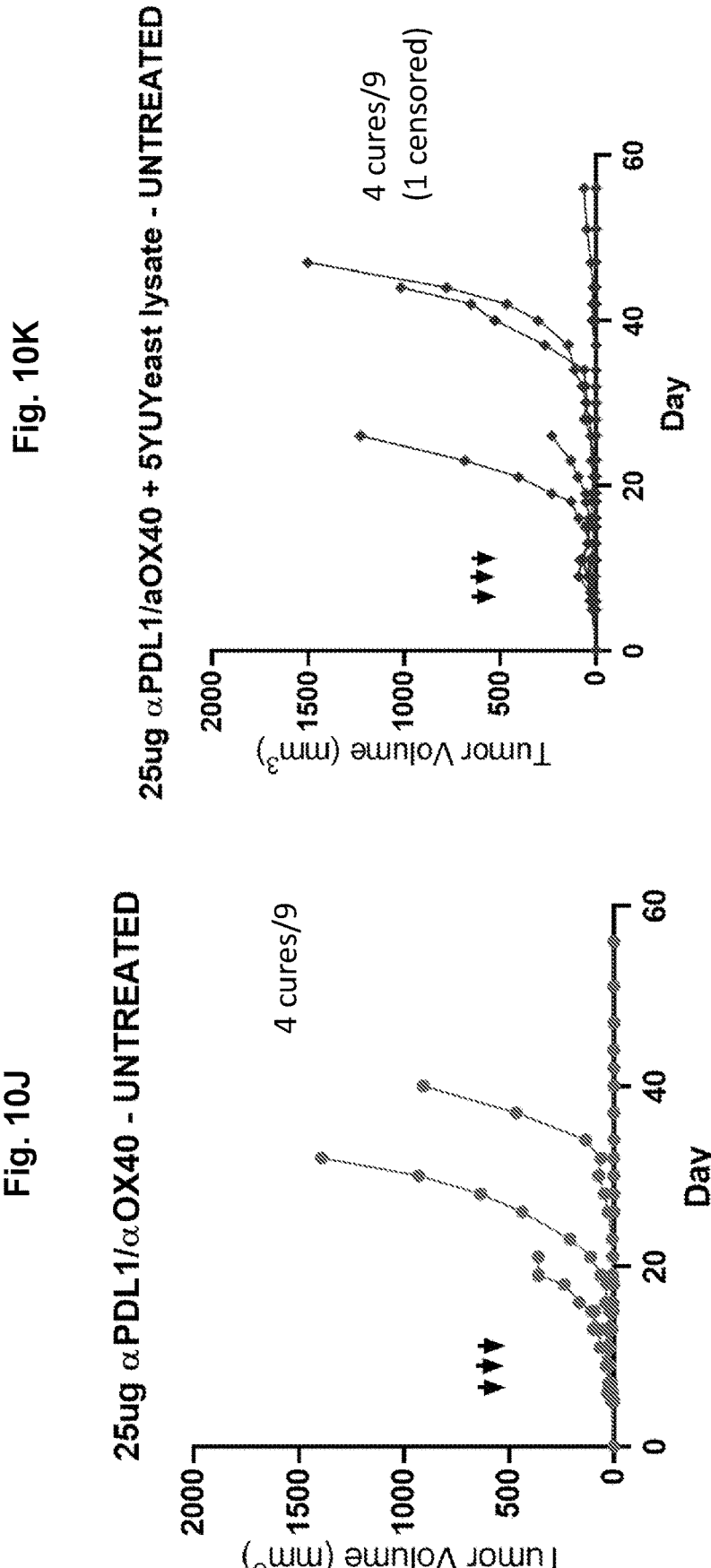
Figure 10L:
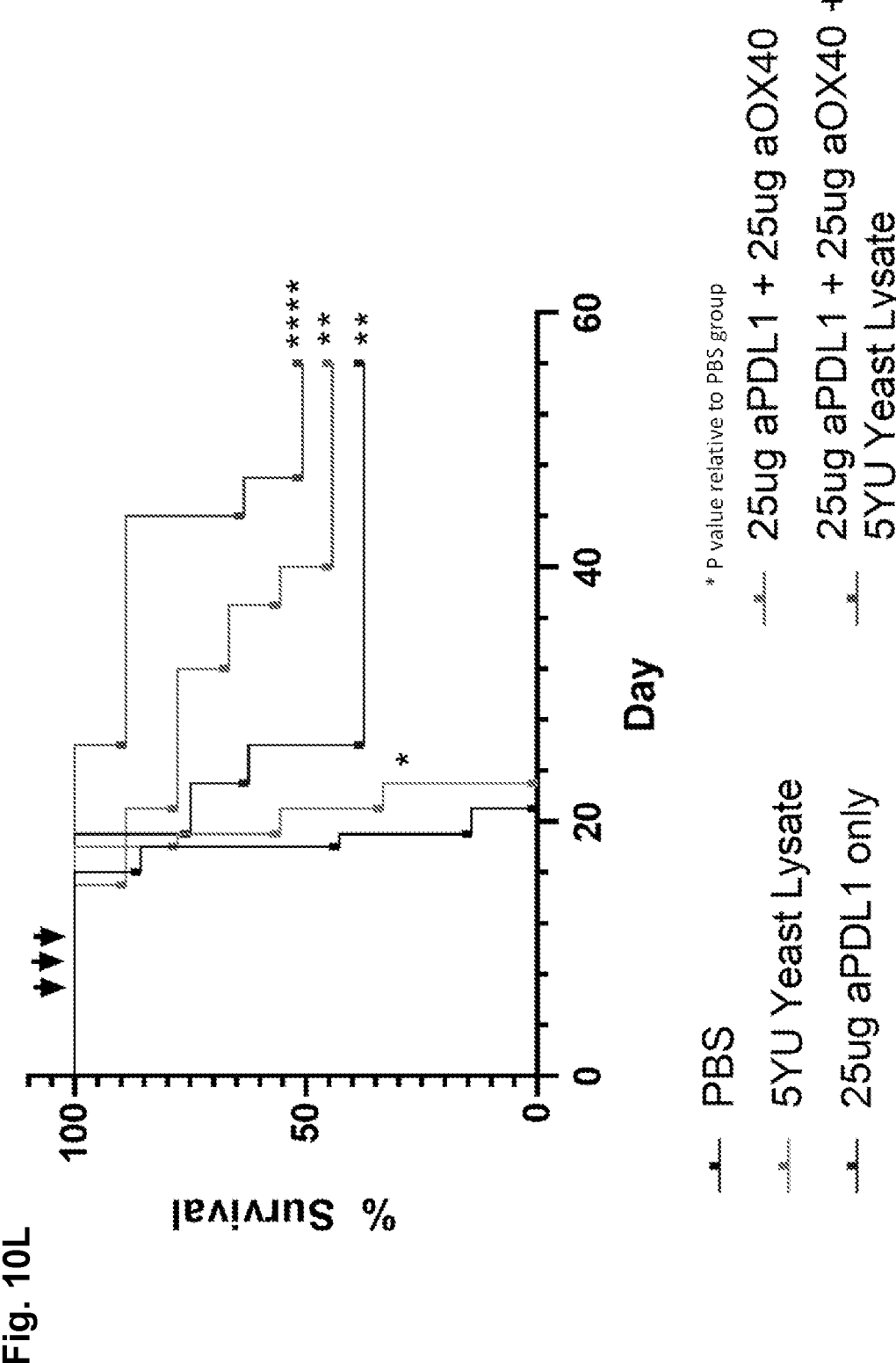

This example shows strong therapeutic effect of αPDL1/αOX40+Yeast Lysate intratumoral therapy in a bilateral MC38 implantation model. Female C57BL/6 mice were intradermally implanted with 300,000 MC38 tumor cells on the right flank (day 0) and on the left flank (day 2). On day 7 one tumor per mouse was treated 3 times (every other day) with 25 μg each of αOX40 agonistic antibody and αPD-L1 antibody plus 5 YU of yeast null lysate (FIG. 10A). Growth impairments for (FIGS. 10B-10F) treated and (FIGS. 10G-10K) untreated tumors are shown, with cure rates indicated. (FIG. 10L) Kaplan-Meier curves showing overall survival to day 58 post challenge (collective data, treated and untreated tumors). Death events (sacrifice) were recorded when a single tumor reached 1000 mm$^3$ or the combined treated and untreated tumor volume reached 1500 mm$^3$. Statistics by Mantel-Cox test for treatment groups relative to PBS: , P<0.01; **, P<0.0001.

Example 11

Figure 11A:
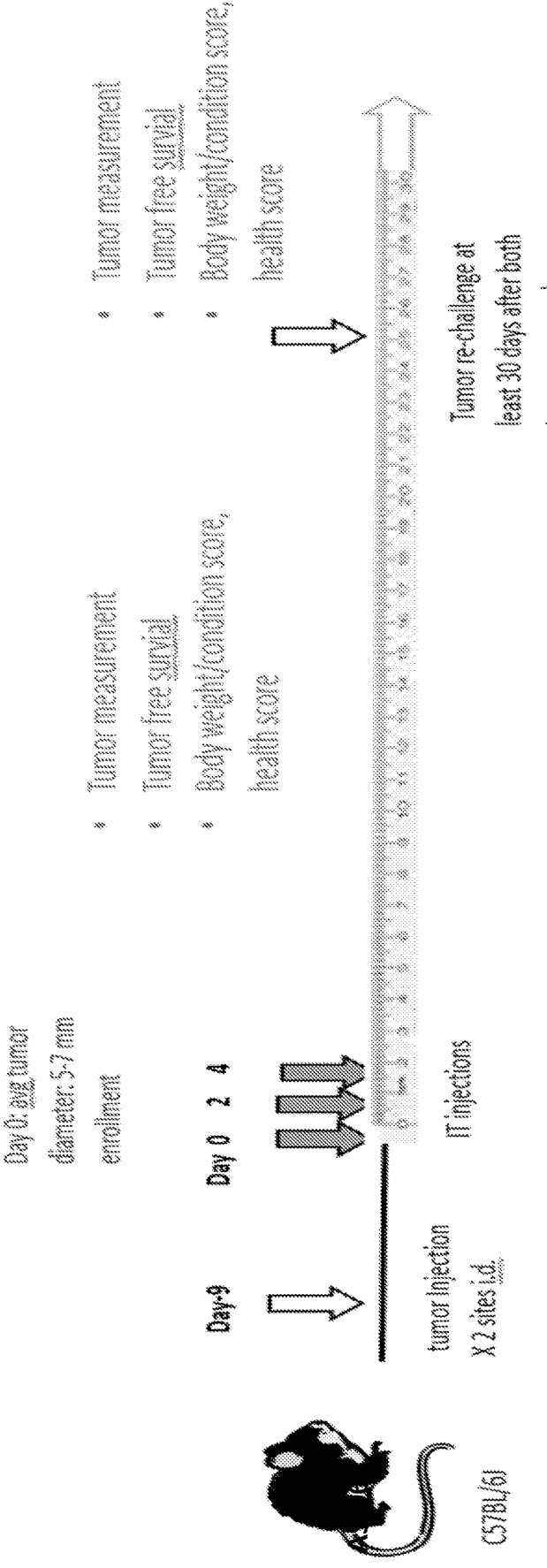
Figure 12F:
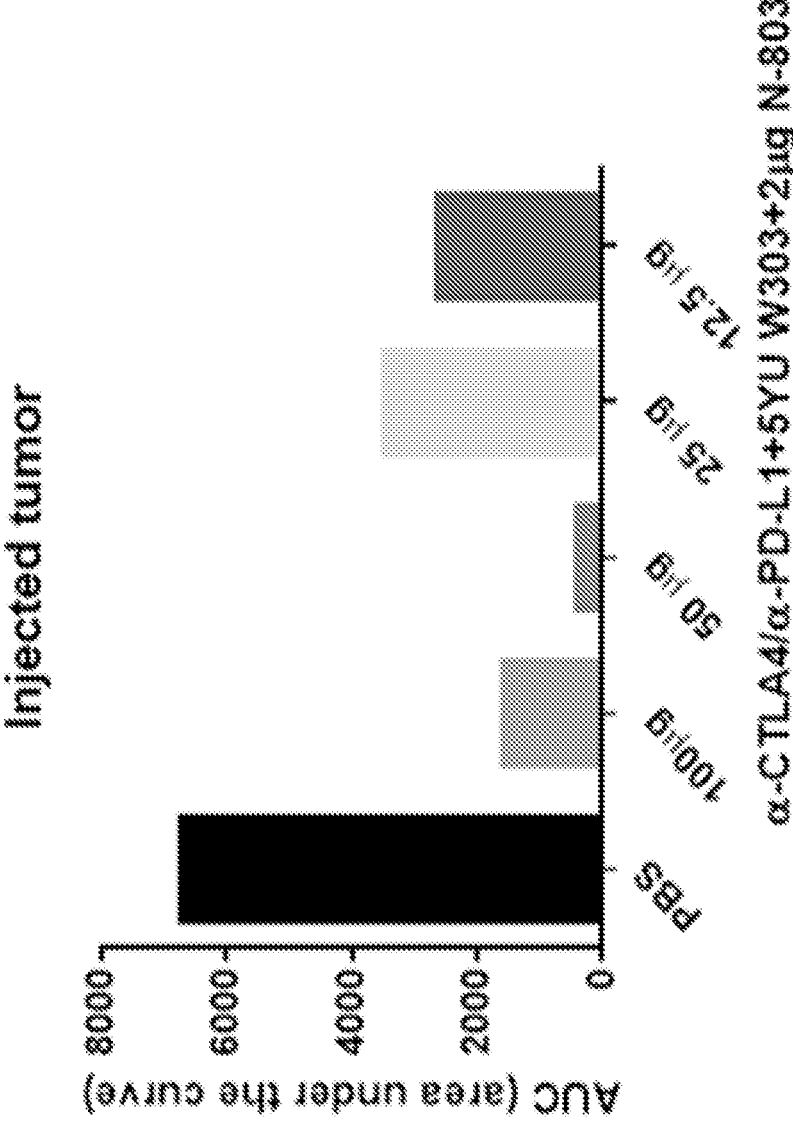
Figure 12E:
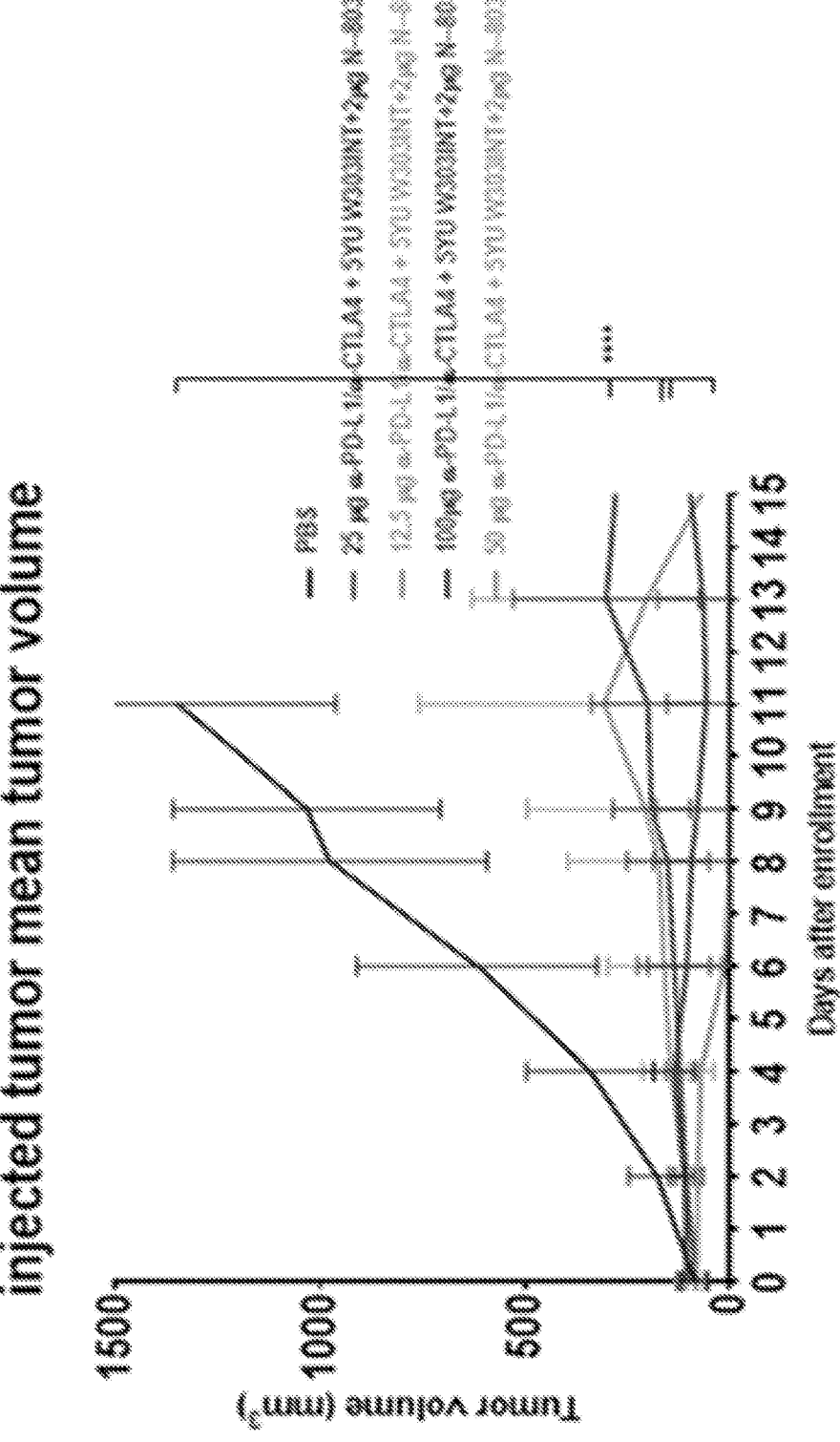
Figure 13E:
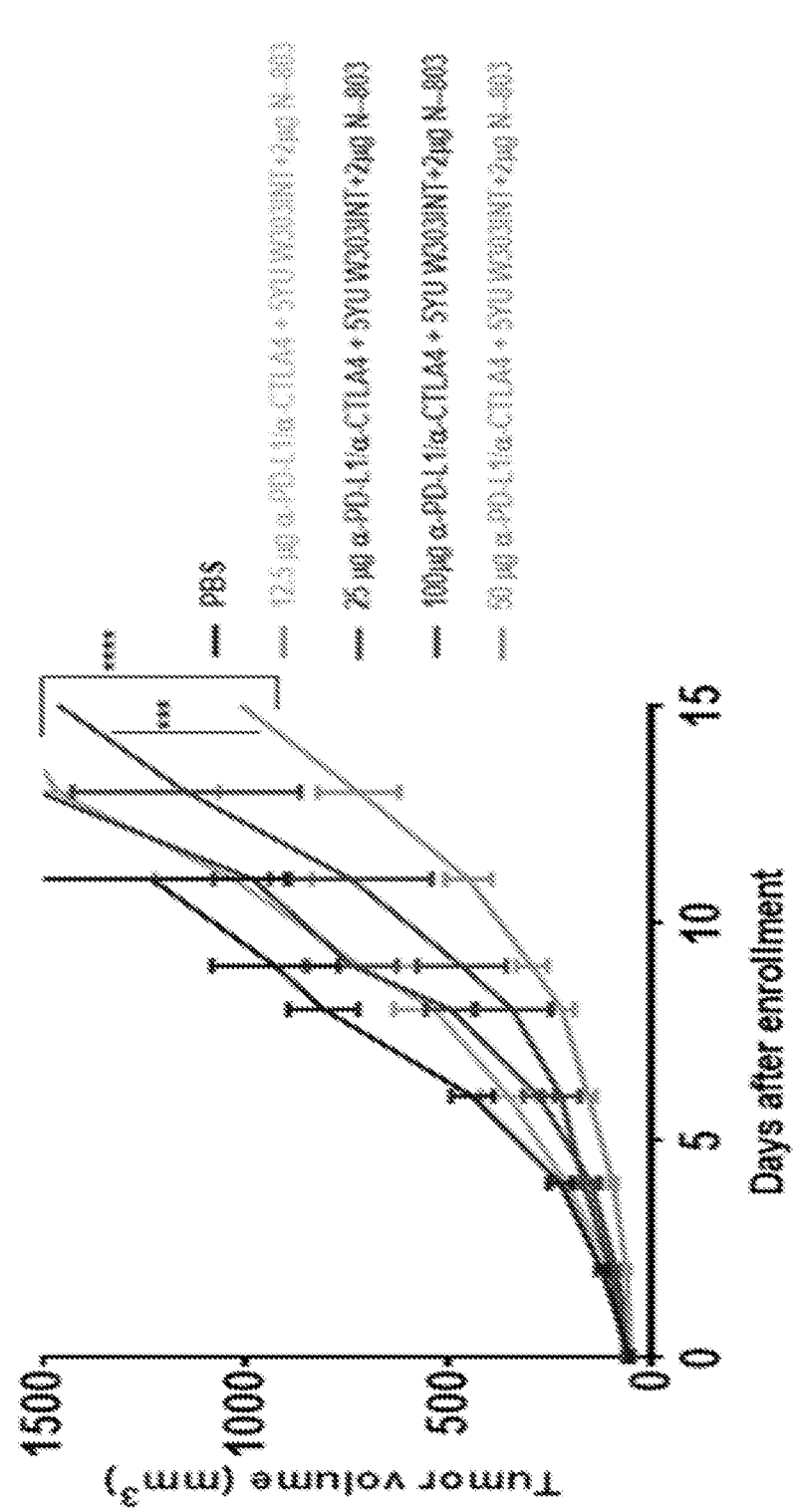
Figure 13F:
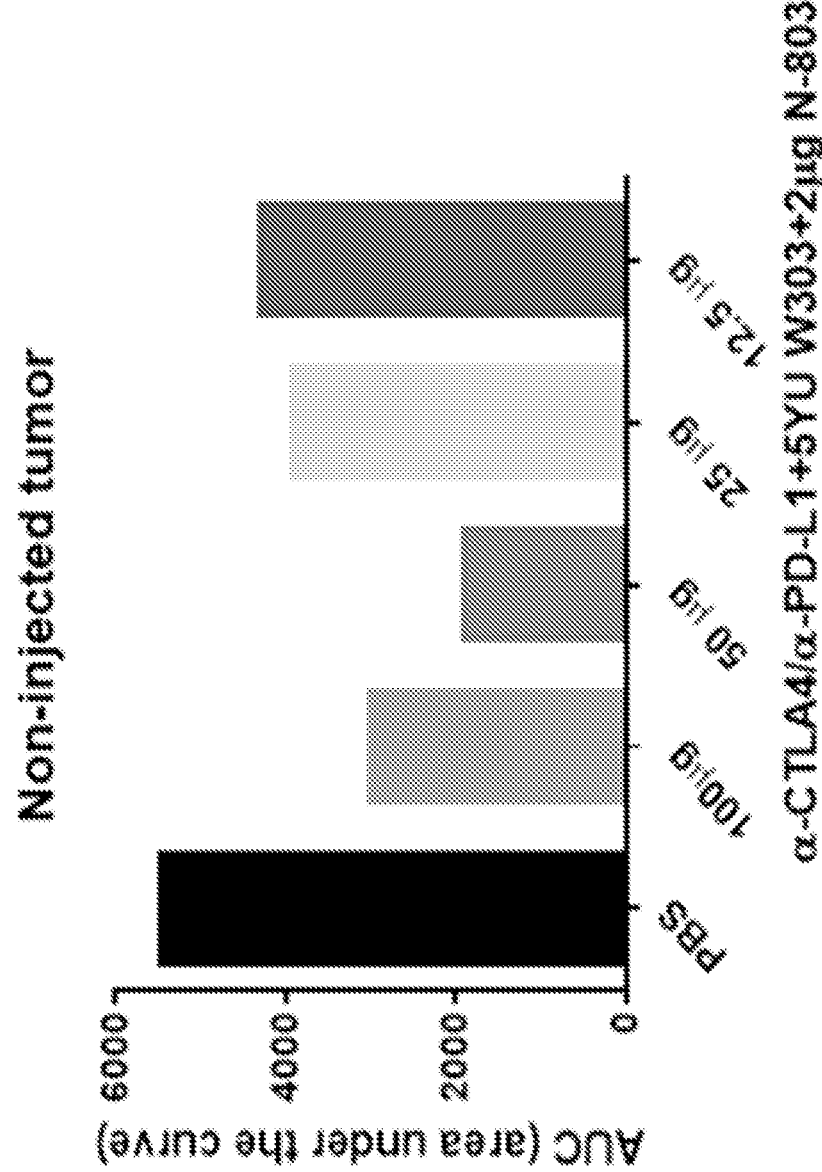
Figure 14A:
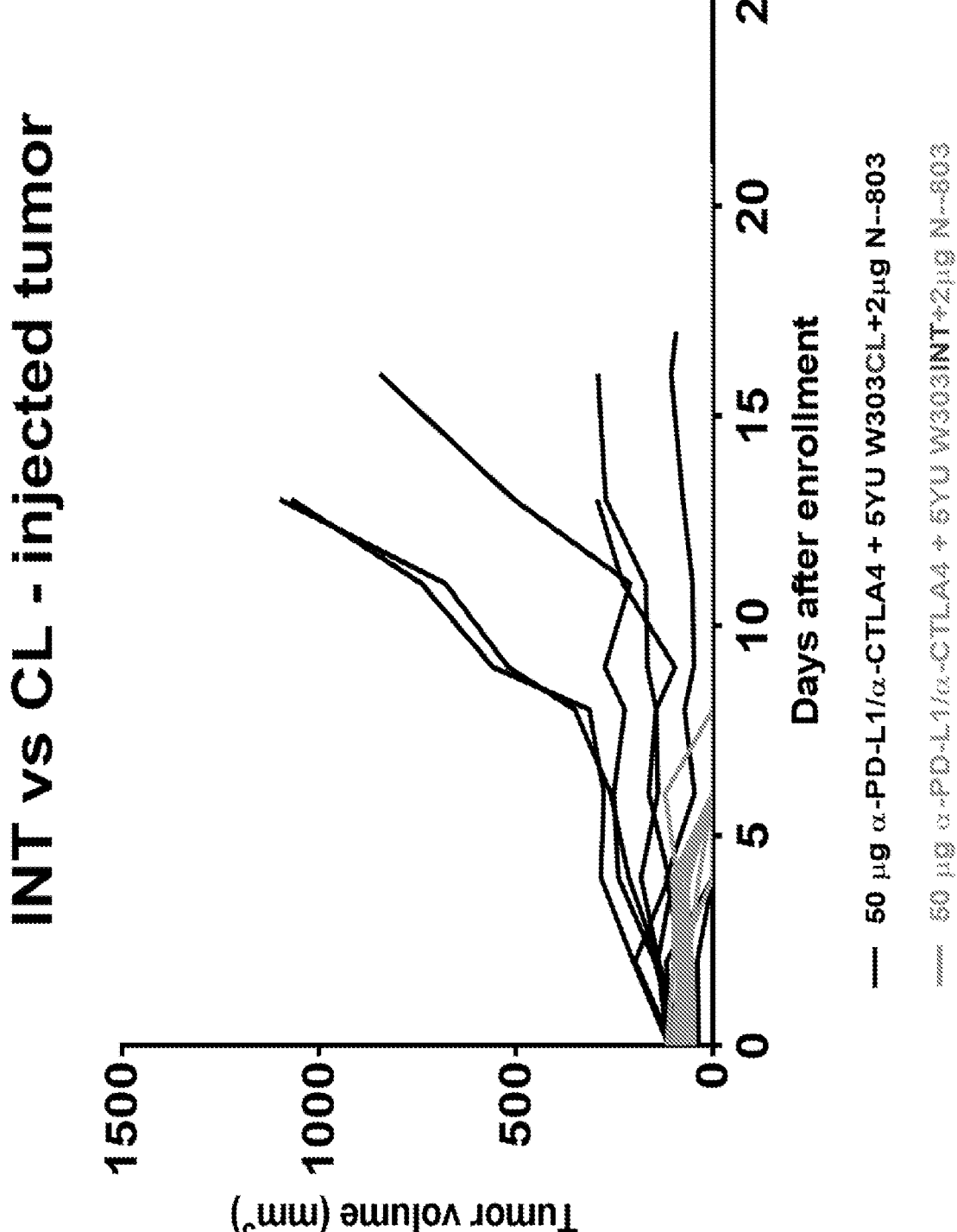
FIGS. 14A, 14B, 14C and 14D show a comparison of intact yeast (INT) and cleared lysate (CL: (INT yeast was pressured lysed, centrifuged and filtered)) yeast formulations in a 2-tumor B16.F10 melanoma mouse model.
Figure 14B:
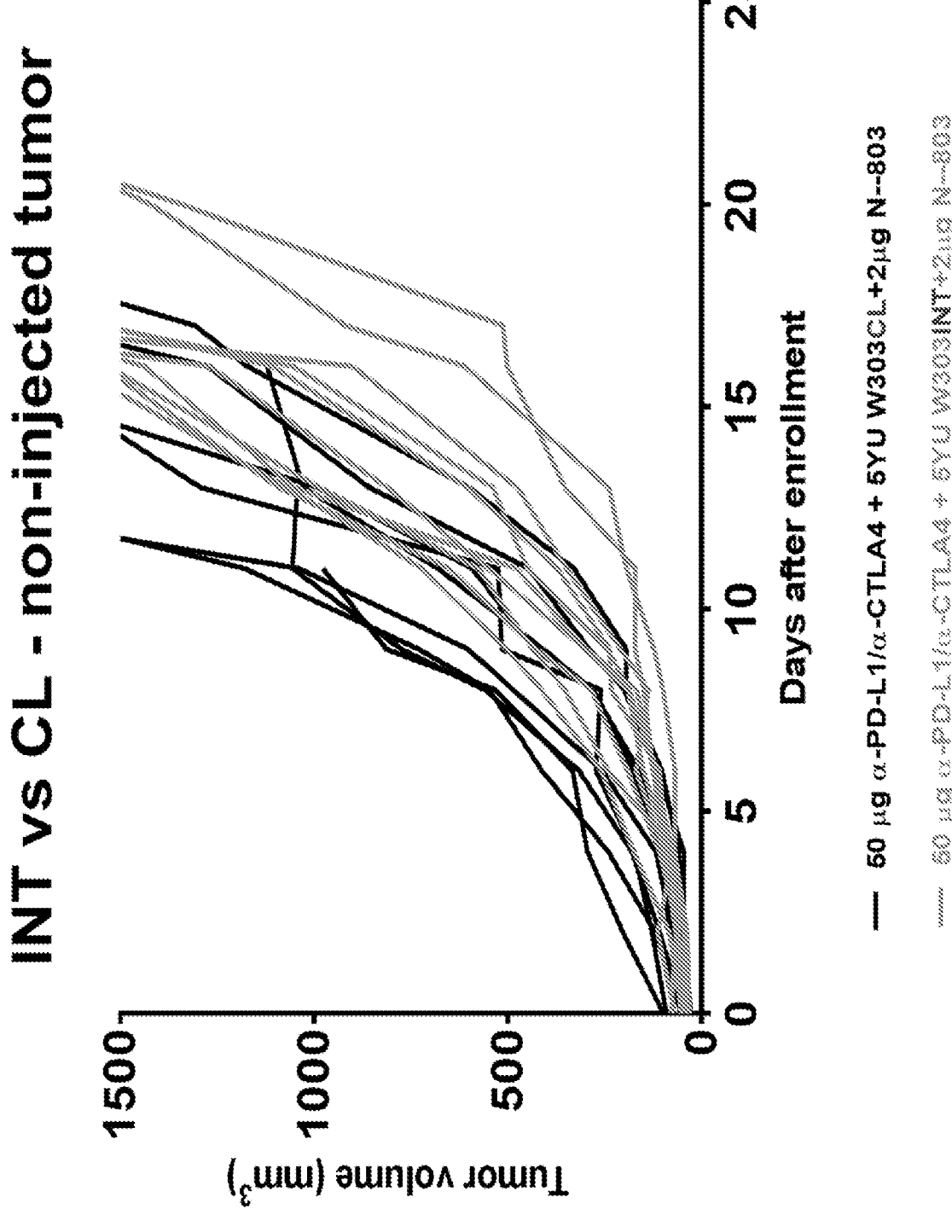
Figure 14C:
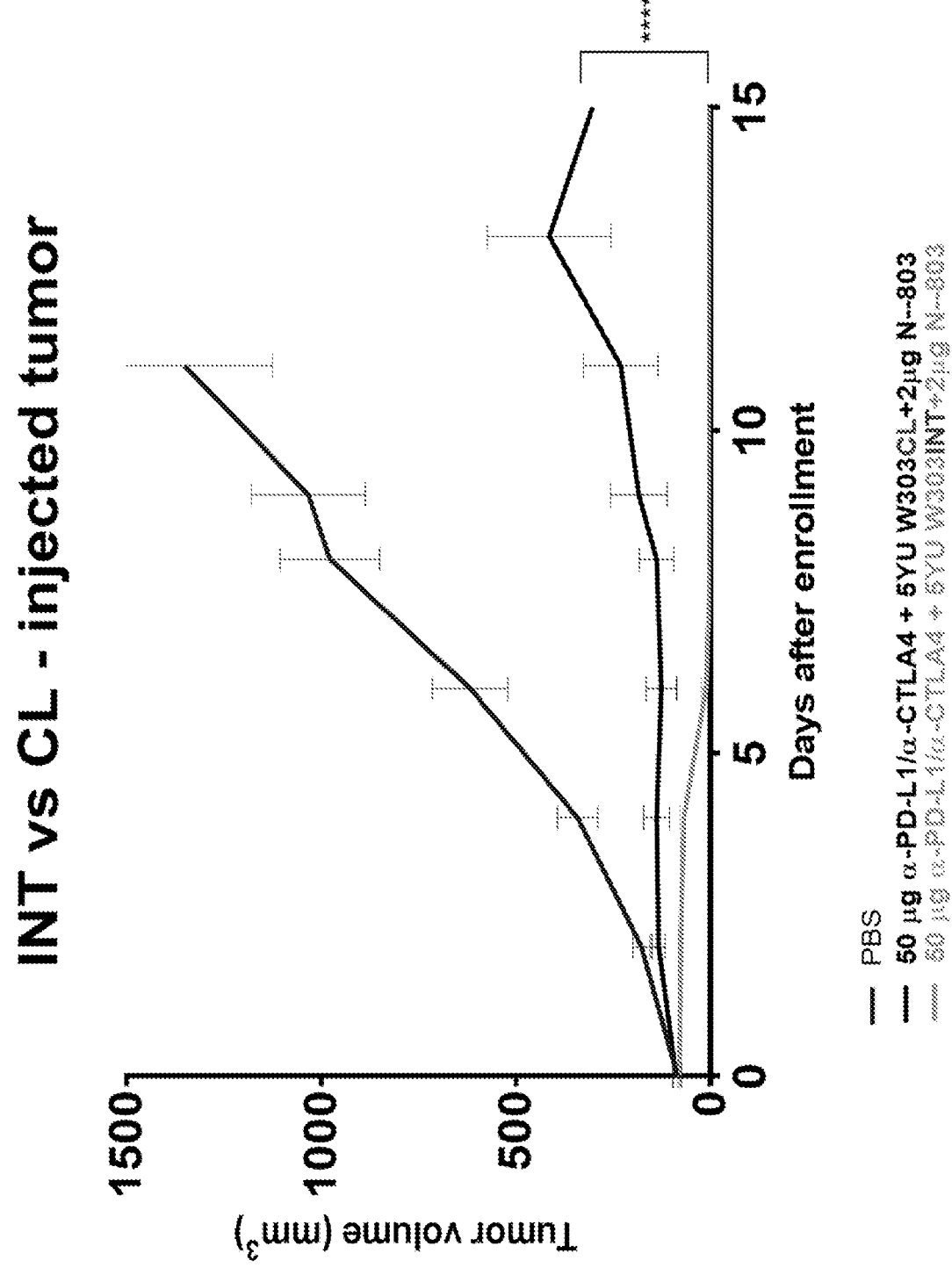
Figure 14D:
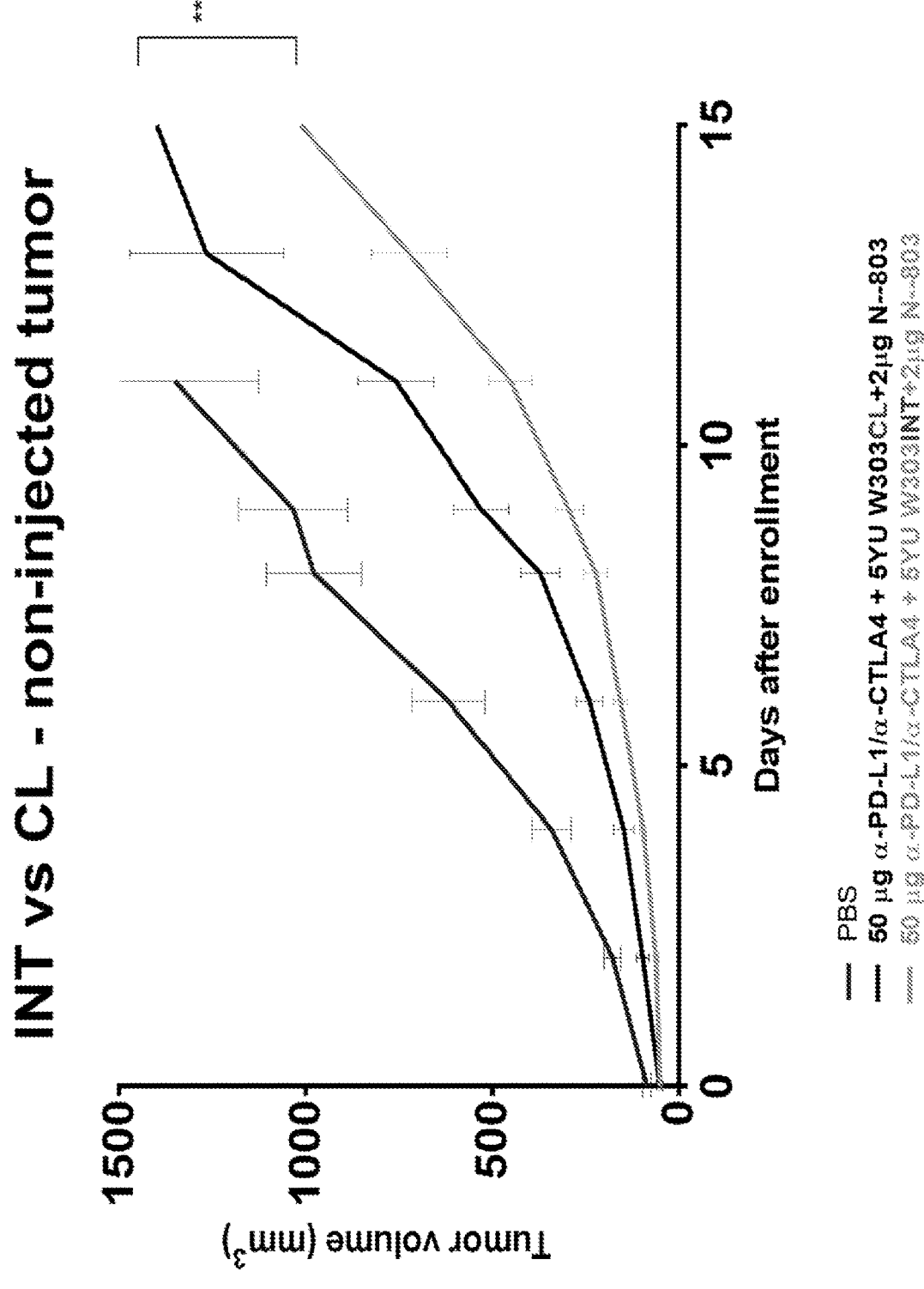

This example shows the evaluation of anti-CTLA4, anti-PD-L1, N-803 and Yeast (W303) in a two-tumor IT B16.F10 mouse model. FIG. 11A shows a schematic of the IT injection regimen and FIG. 11B shows the treatment groups and specific amounts of the various treatment components. The assay was generally performed as in Example 1. As shown in FIGS. 12A-12F, tumors that were injected with 50 ug of anti-CTLA4/anti-PD-L1/N-803/Yeast were eliminated (see FIG. 12A, 50 ug injected tumor graph). As shown in FIGS. 13A-13F, IT injection of anti-CTLA4/anti-PD-L1/N-803/Yeast delayed the tumor growth of no-injected distal tumors. Overall, the results in FIGS. 12A-12F and 13A-13F show that anti-CTLA4, anti-PD-L1, N-803 and Yeast (W303) administered via IT injection results in significant reduction in the growth of both injected and non-injected tumors.

Example 12

This example shows the efficacy comparison of intact yeast (INT) versus cleared lysate (CL) yeast (i.e., CL yeast are INT yeast that were pressure lysed, centrifuged and filtered) using the two-tumor B16.F10 mouse melanoma model as in Example 11. As seen in FIGS. 14A-14D, INT yeast formulations are more effective in reducing tumor growth in both injected and non-injected tumors than the CL yeast formulations when combined with N-803 and checkpoint inhibitors.

Example 13

Figures 15A, 15B:
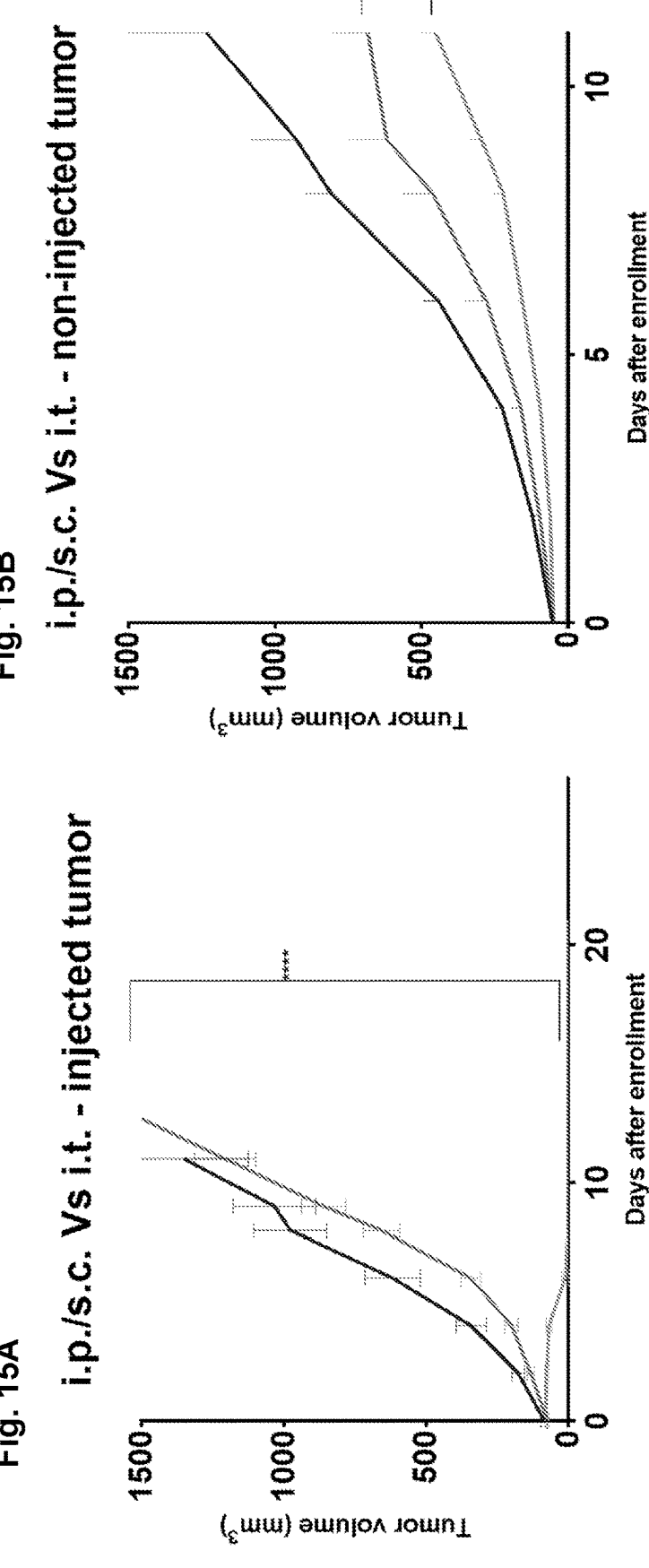
FIGS. 15A, 15B and 15C shows a comparison of IT (also referred to as "i.t.") injection on tumor growth inhibition compared to intraperitoneal (IP or i.p.) and/or subcutaneous (SC or s.c.) injection administration routes. PBS (control-top line); 50 μg α-PD-L1/α-CTLA (i.p.)+5YU W303INT (s.c.)+2 μg N-803 (s.c.) (middle line); and 50 μg α-PD-L1/α-CTLA+5YU W303INT+2 μg N-803 (i.t.).
Figure 15C:
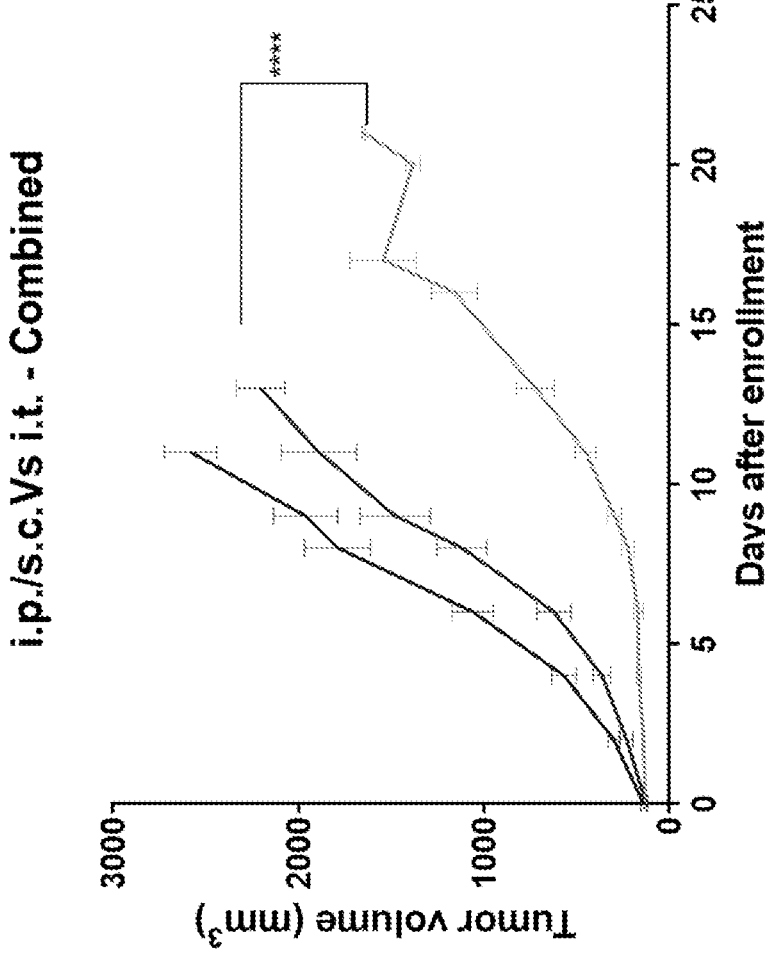
Figure 16:
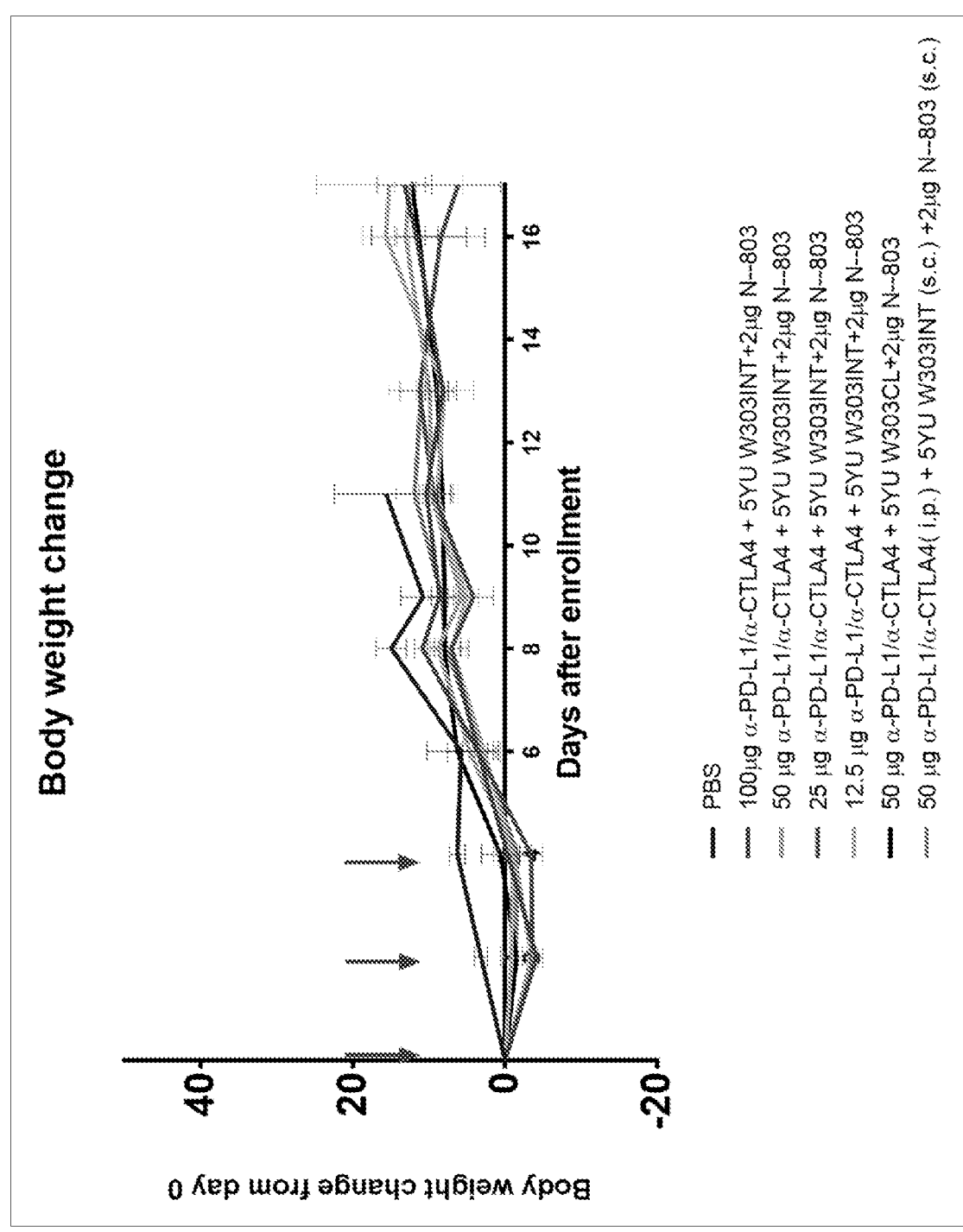
FIG. 16 shows the results of IT or IP/SC injection of anti-CTLA4/anti-PD-L1/N-803/Yeast on mouse body weight.

This example shows the evolution of IT and IP/SC immunotherapy administration of anti-CTLA4/anti-PD-L1/N-803/Yeast in a two-tumor B16.F10 melanoma model as discussed in Example 11 (specifically Group 3 and Group 7 described in FIG. 11B). As shown in FIGS. 15A-15C, IT injection provides better tumor growth inhibition than IP/SC administration routes. Further, FIG. 16 demonstrates that IT or IP/SC injection of anti-CTLA4/anti-PD-L1/N-803/Yeast does not impact mouse body weight.

Example 14

Figure 17:
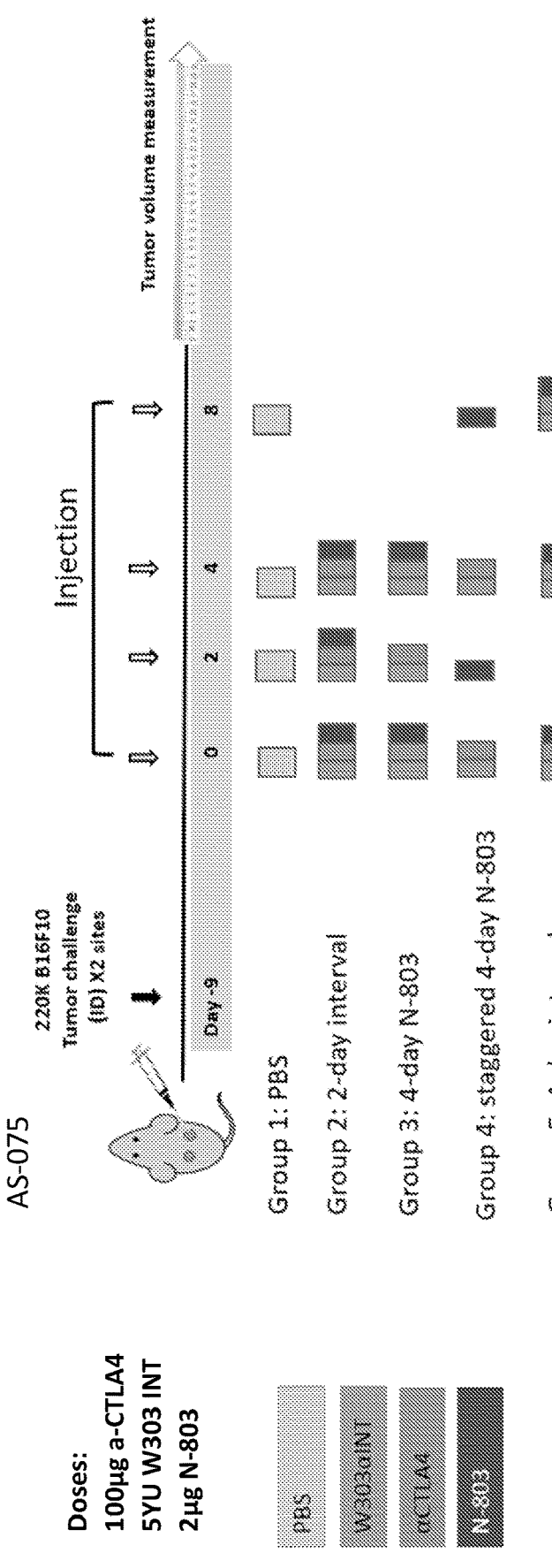
FIG. 17 shows the experimental schematic for evaluation of an N-803 dose schedule in combination IT therapy in a 2-tumor B16.F10 melanoma mouse model.
Figure 18:
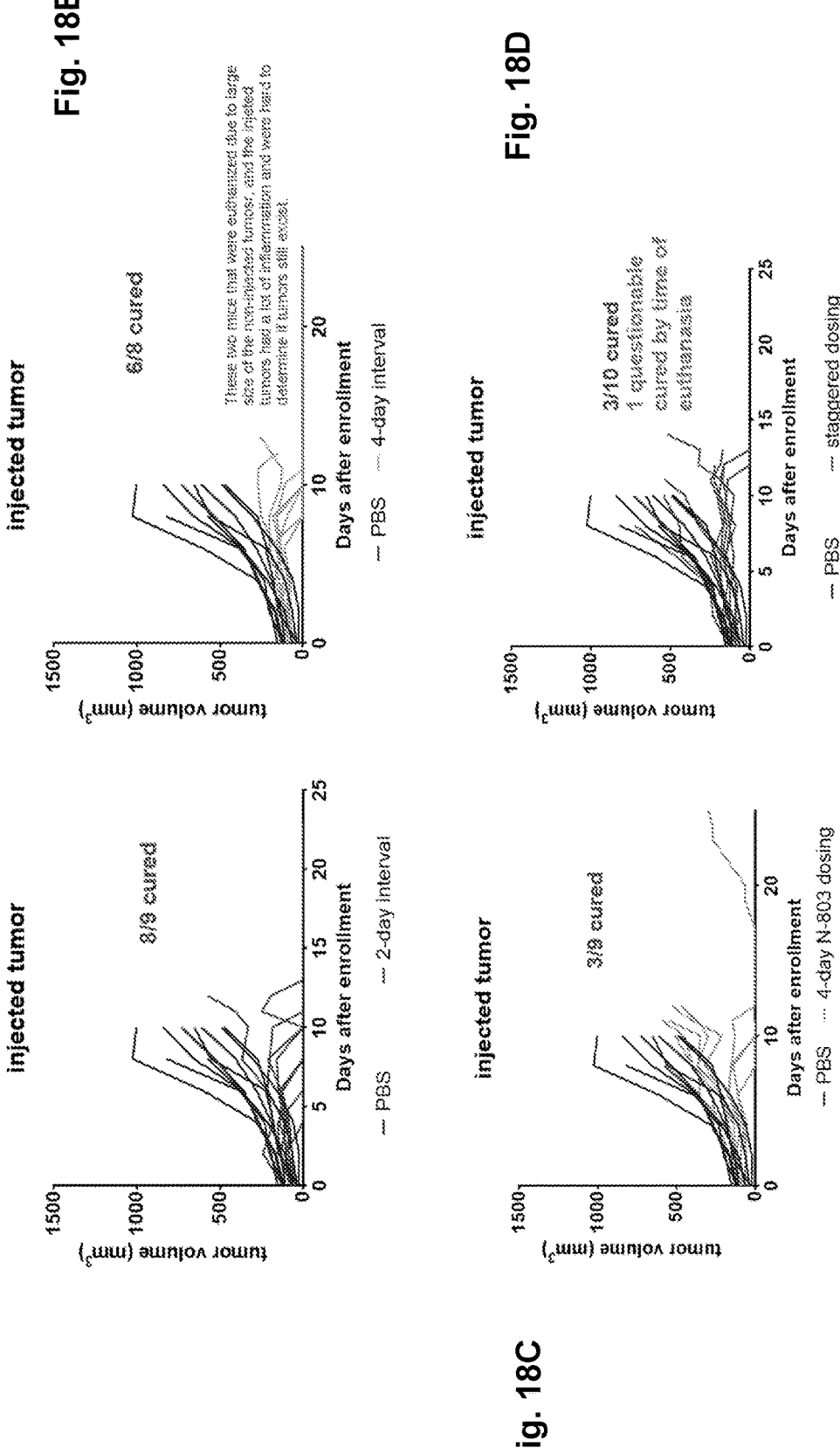
FIGS. 18A, 18B, 18C and 18D show the results of the simultaneous injection of N-803 with anti-CTL4/Yeast given 3 times every 2 days on the inhibition of tumor growth of injected tumor(s).
Figure 19:
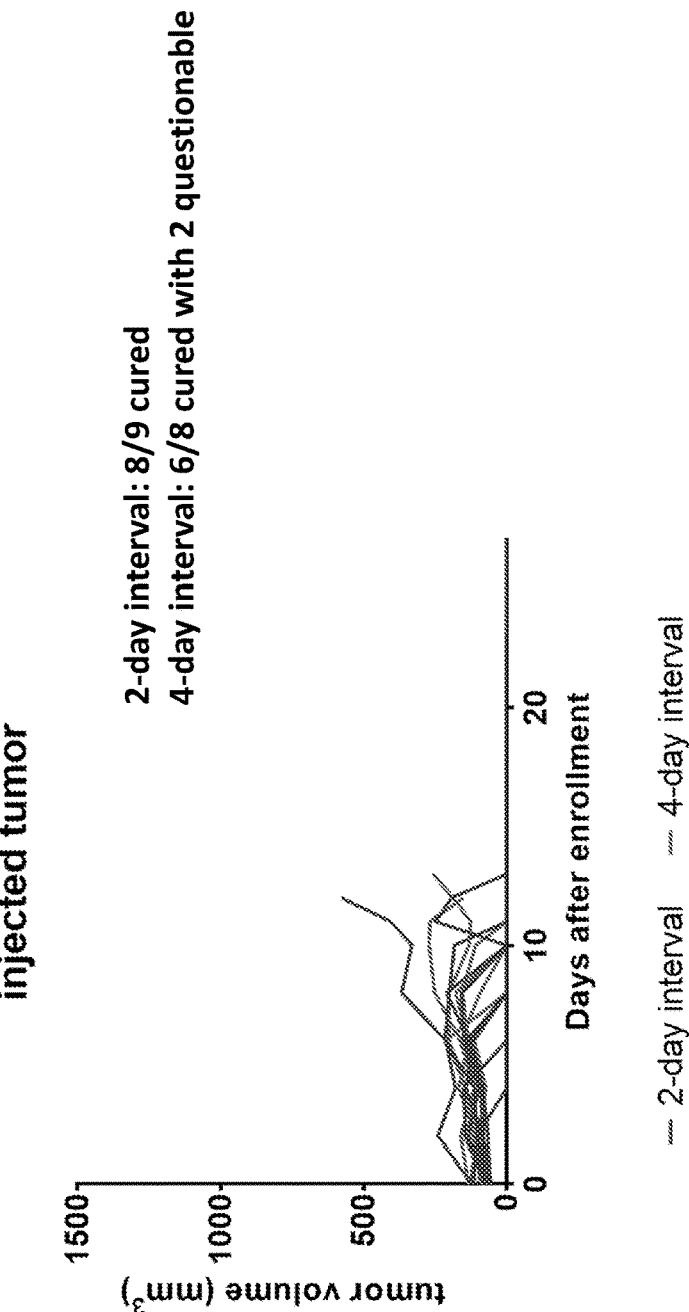
FIG. 19 shows the comparison of 2-day and 4-day N-803 dose interval on the growth of injected tumor(s).
Figures 20A, 20B, 20C, 20D:
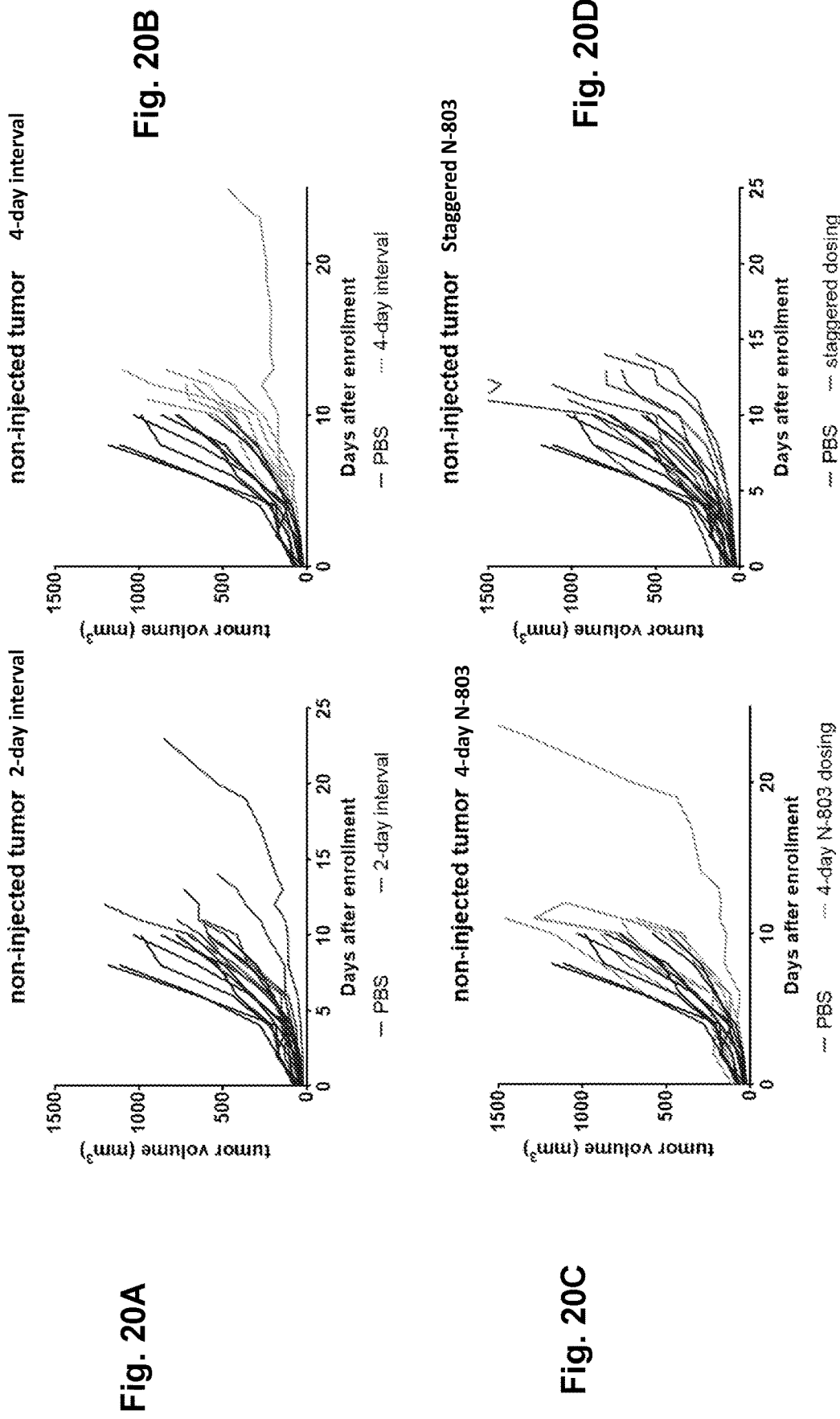
FIGS. 20A, 20B, 20C and 20D show the results of the simultaneous injection of N-803 with anti-CTL4/Yeast given 3 times every 2 days on the inhibition of tumor growth of non-injected tumor(s).
Figures 21A, 21B:
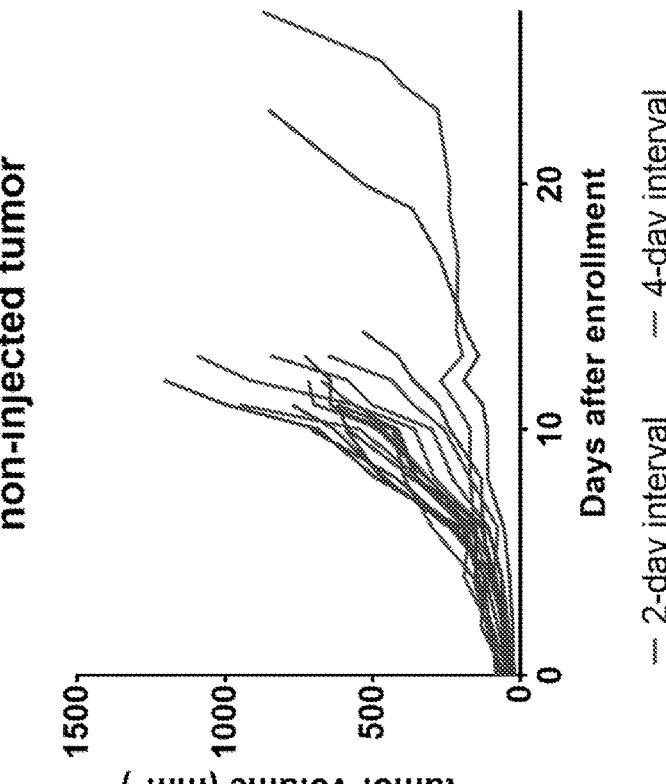
FIGS. 21A and 21B shows a comparison of 2-day and 4-day N-803 dose interval on the growth of non-injected tumor(s).

The purpose of this example was to determine the most effective dosing schedule of N803 with administered as an intra tumor injection with anti-CTL4 and intact Yeast (W303a). FIG. 17 shows the 803 dose schedule in combination IT therapy in a two-tumor B16.F10 melanoma model. As shown in FIGS. 18A-18D, simultaneous injection of N-803 with anti-CTLA4/Yeast given three times every 2 days effectively inhibits tumor growth of injected tumors. FIG. 19 shows a comparison of 2-day and 4-day N-803 dose interval on growth of the injected tumor with 2-day showing 8/9 cured and the 4-day with 6/8 cured with 2 questionable. As shown in FIGS. 20A-20D simultaneous injection of N-803 with anti-CTLA4/Yeast given three times every 2 days effectively inhibits tumor growth of non-injected tumors. FIGS. 21A-21B show the comparison of 2-day and 4-day N-803 dose interval on the growth of non-injected tumors.

Example 15

Figures 22A, 22B:
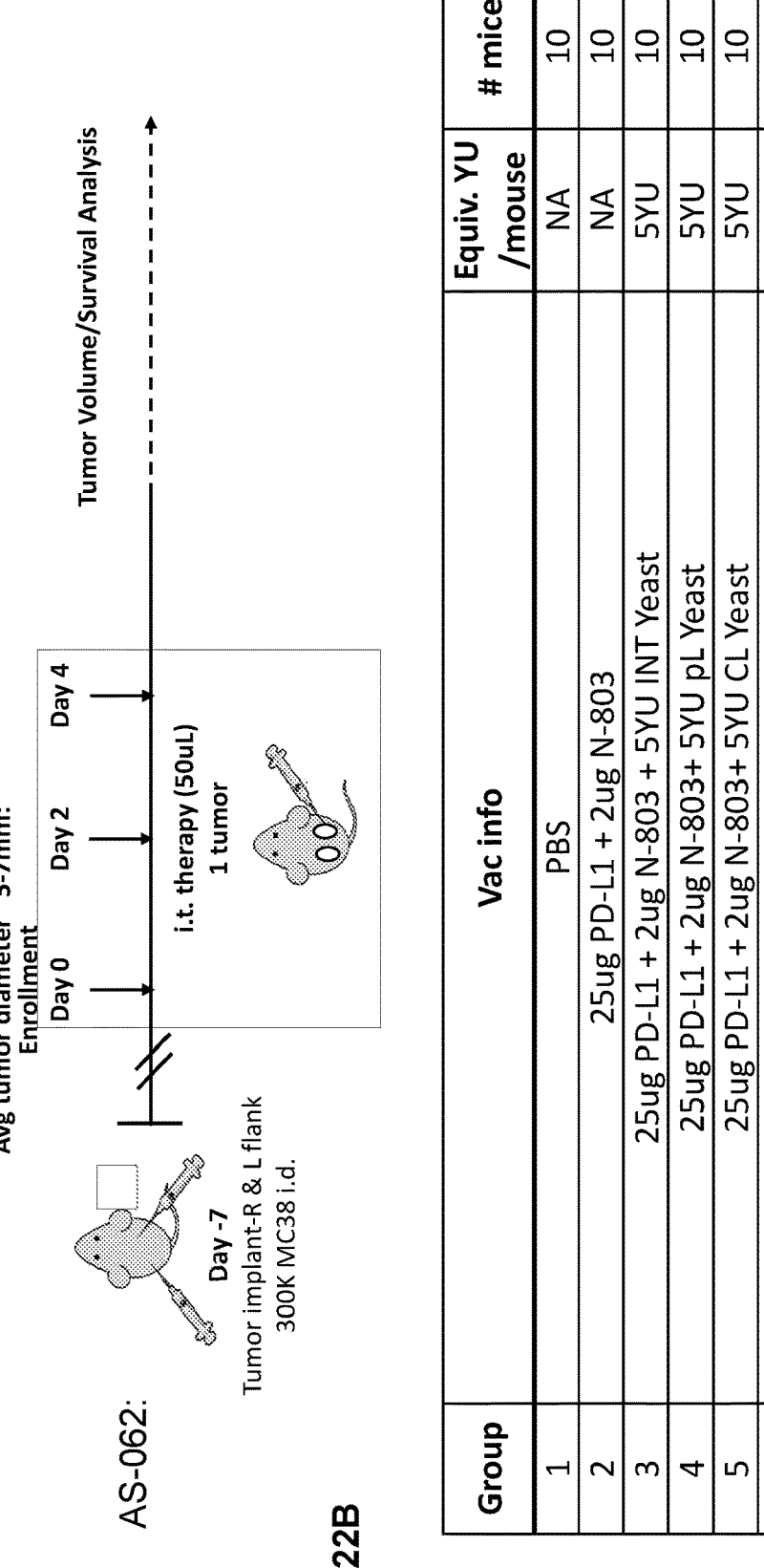
FIG. 22A shows the experimental schematic assay for evaluating N-803/anti-PD-L1+Yeast INT or CL formulations injected IT in a 2-tumor MC38 colorectal cancer model.
FIG. 22B shows a chart of the amounts and formulations ("vac info") used for each assay group.
Figures 23A, 23B:
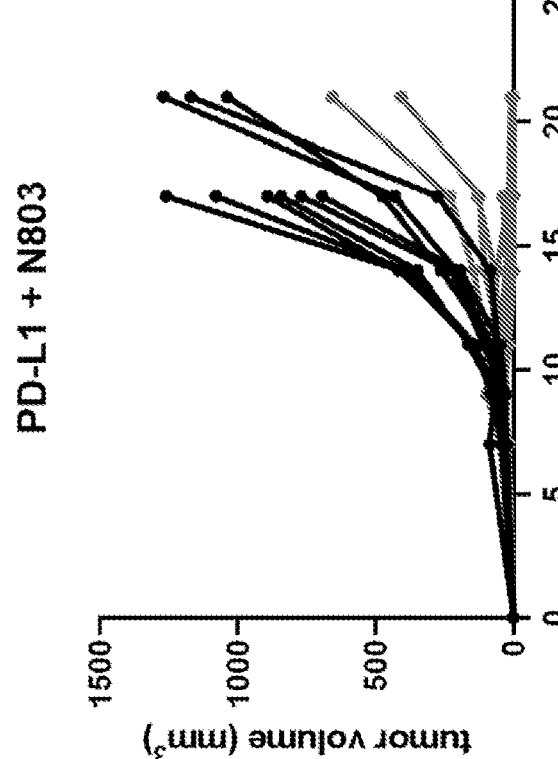
FIGS. 23A, 23B, 23C, 23D, and 23E show the results on the growth delay of injected tumors using the assay and the formulations shown in FIGS. 22A and 22B.
Figures 23C, 23D:
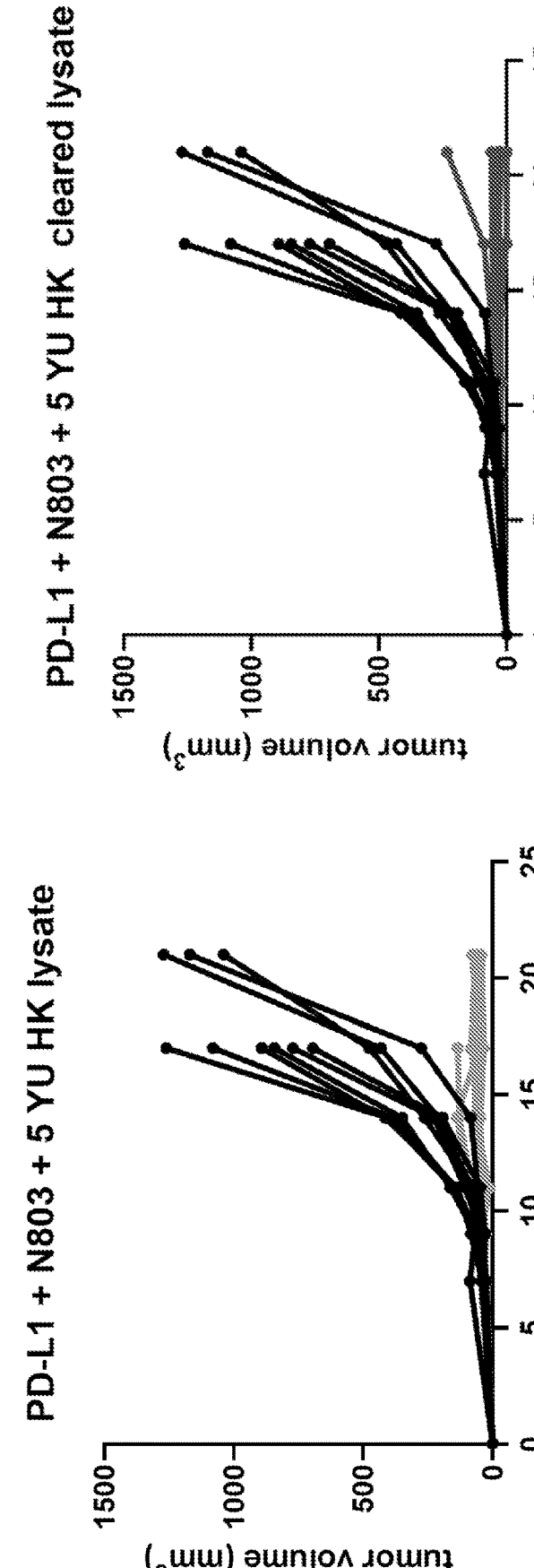
Figure 23E:
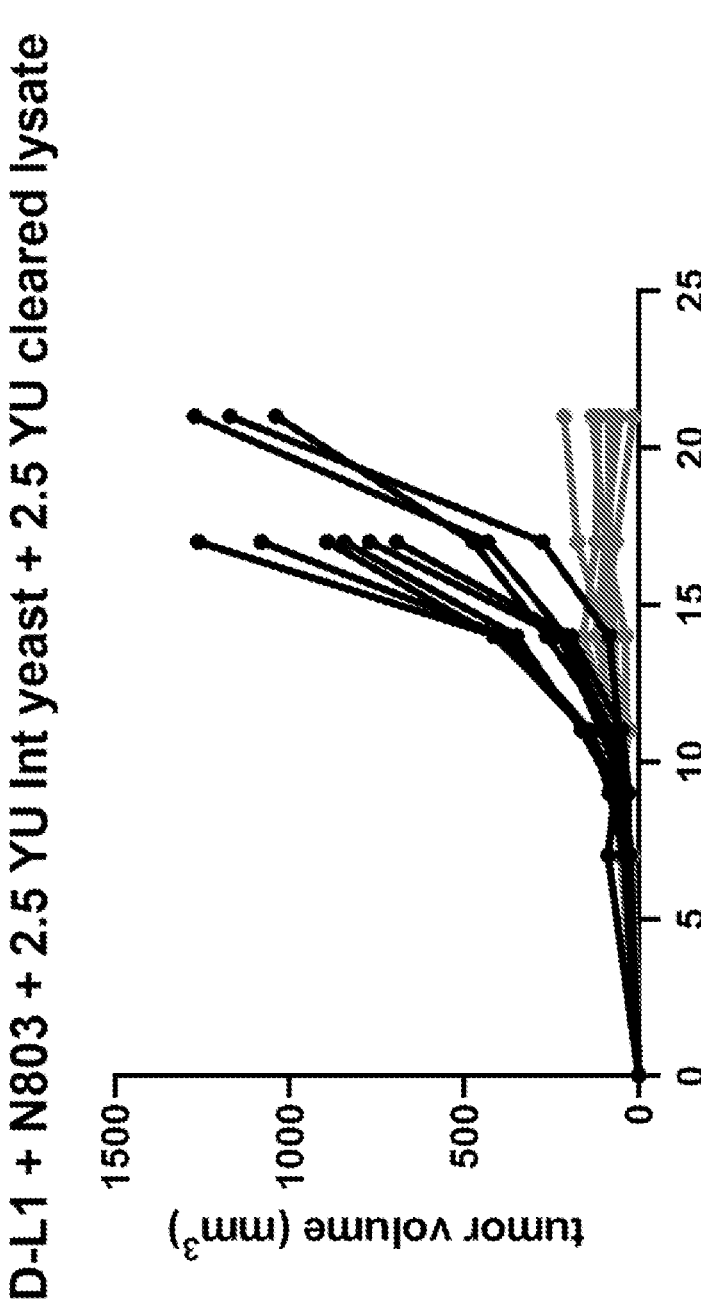
Figures 24A, 24B:
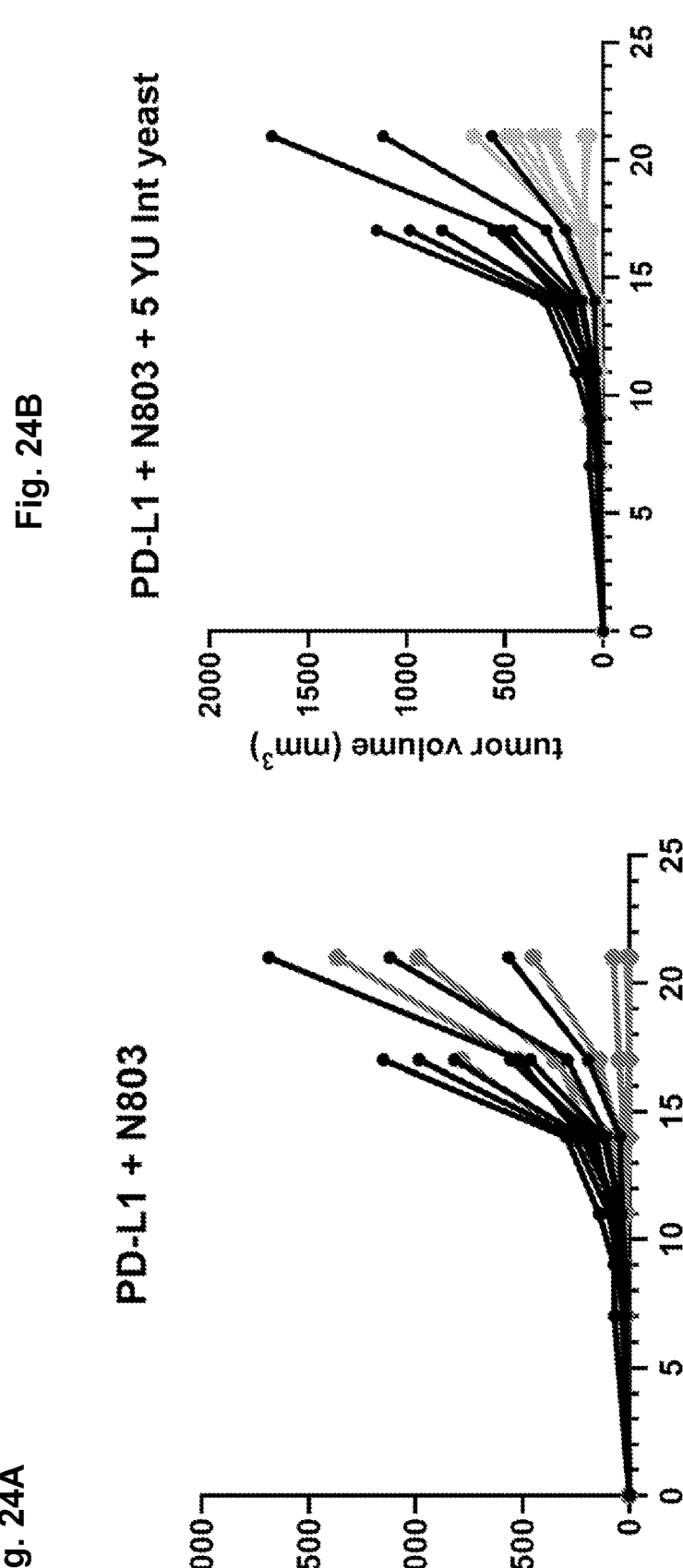
Figures 24C, 24D:
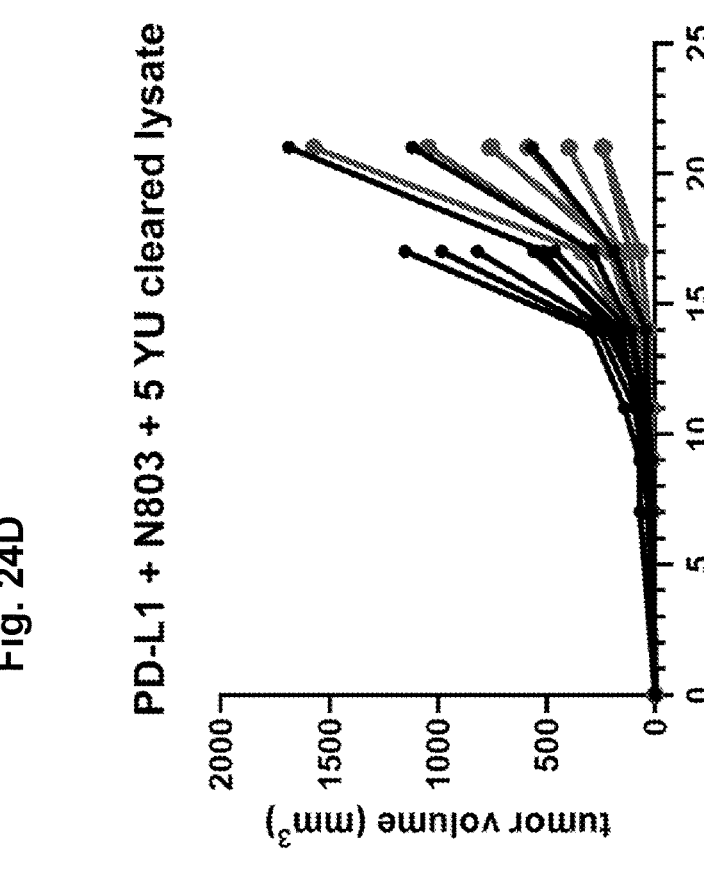
Figure 24E:
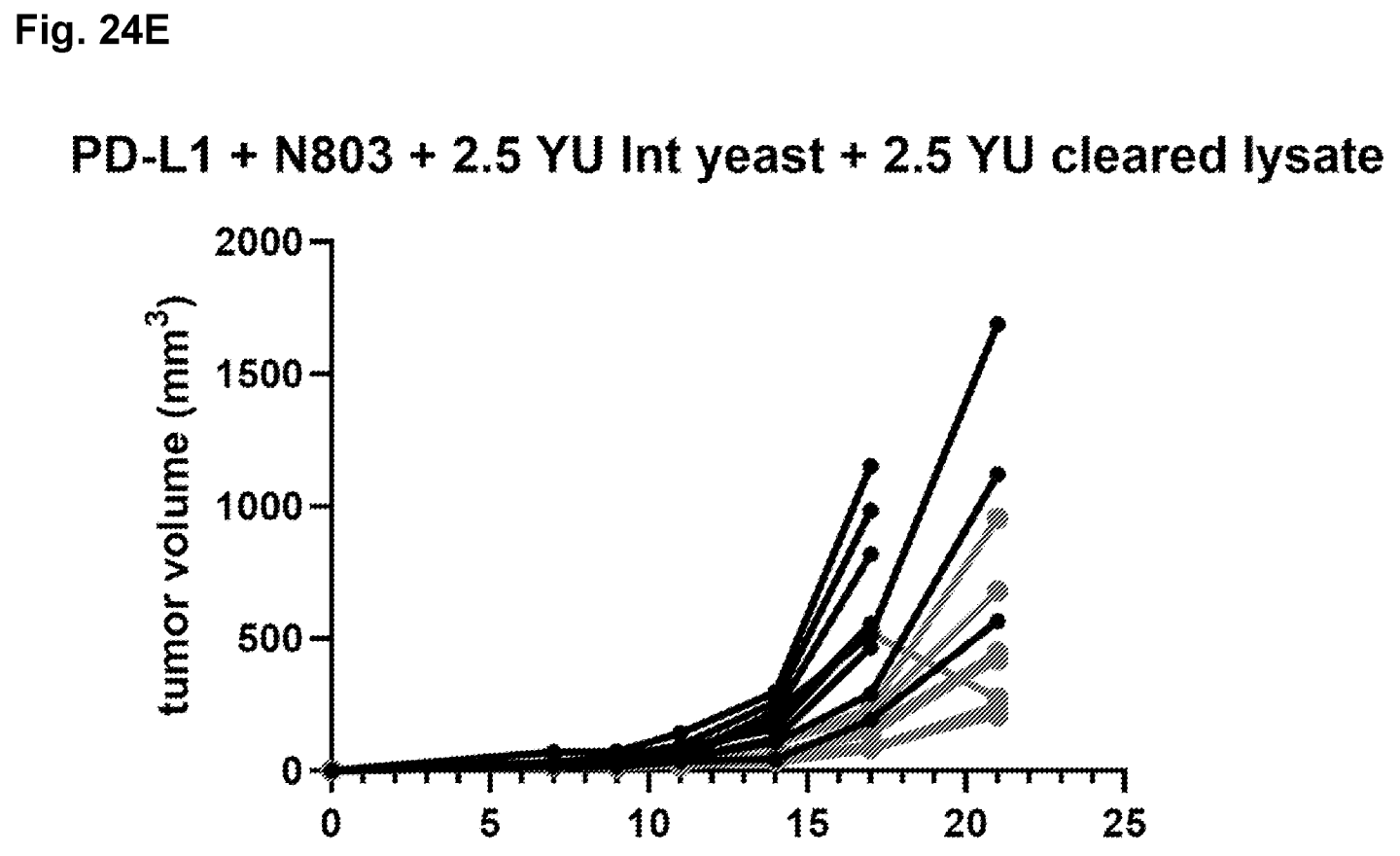

This example shows the evaluation of N-803/anti-PD-L1 plus Yeast INT or Yeast CL formulations injected IT in a two-tumor MC38 colorectal cancer model. FIG. 22A shows a schematic of the IT injection regimen and FIG. 22B shows the treatment groups and specific amounts (in the Vac info) of the various treatment components along with the equivalent Y.U. amounts of the yeast. AS shown in FIGS. 23A-23E, in combination with anti-PDL1/N-803, Yeast lysates (CL) are the most effective yeast formulation for delaying growth of the injected tumor. As shown in FIGS. 24A-24A, in combination with anti-PDL1/N-803, INT Yeast are the most effective yeast formulation for delaying growth of the non-injected tumor.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A composition for injection into a solid tumor, wherein the composition comprises effective amounts of a yeast and/or a lysate thereof, a checkpoint inhibitor selected from the group consisting of an anti-CTLA-4 antibody and an anti-PDL1 antibody, and an immunostimulatory protein selected from the group consisting of an Ox40 receptor agonist and nogapendkin-alfa-inbakicept (NAI; N-803).

2. The composition of claim 1, wherein the yeast is *Saccharomyces cerevisiae*.

3. The composition of claim 1, wherein the yeast is genetically engineered to express a tumor associated antigen, tumor specific antigen, or a neoepitope.

4. The composition of claim 1, wherein the Ox40 receptor agonist is a monoclonal antibody or a receptor ligand.

5. The composition of claim 1, wherein the tumor is a mucosal tumor, melanoma, a lung tumor or a colorectal tumor.

6. The composition of claim 1, wherein the tumor is metastatic.

7. The composition of claim 1, wherein the yeast is genetically engineered to express protein G on the surface of the yeast.

8. The composition of claim 7, wherein the Ox40 receptor agonist is an Fc-agonist fusion protein, and wherein the Fc-agonist fusion protein is bound to the yeast prior to administration.

9. A method of treating a solid tumor, the method comprising intratumoral injection of an effective amount of a composition comprising a yeast and/or a lysate thereof, a checkpoint inhibitor selected from the group consisting of an anti-CTLA-4 antibody and an anti-PDL1 antibody, and an immunostimulatory protein selected from the group consisting of an Ox40 receptor agonist and nogapendkin-alfa-inbakicept (NAI; N-803).

10. The method of claim 9, wherein the yeast is *Saccharomyces cerevisiae*.

11. The method of claim 9, wherein the yeast is genetically engineered to express a tumor associated antigen, tumor specific antigen, or a neoepitope.

12. The method of claim 9, wherein the Ox40 receptor agonist is a monoclonal antibody or a receptor ligand.

13. The method of claim 9, wherein the tumor is a mucosal tumor, melanoma, a lung tumor or a colorectal tumor.

14. The method of claim 9, wherein the tumor is metastatic.

15. The method of claim 9, wherein the yeast is genetically engineered to express protein G on the surface of the yeast.

16. The method of claim 15, wherein the Ox40 receptor agonist is an Fc-agonist fusion protein, and wherein the Fc-agonist fusion protein is bound to the yeast prior to administration.

\* \* \* \* \*